United States Patent
Inukai et al.

(10) Patent No.: US 10,676,462 B2
(45) Date of Patent: Jun. 9, 2020

(54) QUINOLINE DERIVATIVE

(71) Applicant: ONO PHARMACEUTICAL CO., LTD., Osaka (JP)

(72) Inventors: Takayuki Inukai, Osaka (JP); Jun Takeuchi, Osaka (JP); Tomoko Yasuhiro, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/540,306

(22) Filed: Aug. 14, 2019

(65) Prior Publication Data

US 2020/0002313 A1    Jan. 2, 2020

Related U.S. Application Data

(63) Continuation of application No. 16/237,275, filed on Dec. 31, 2018, now Pat. No. 10,501,442, which is a continuation of application No. 15/975,999, filed on May 10, 2018, now Pat. No. 10,208,022, which is a continuation of application No. 15/373,091, filed on Dec. 8, 2016, now Pat. No. 9,994,549, which is a continuation of application No. 14/906,993, filed as application No. PCT/JP2014/069419 on Jul. 23, 2014, now Pat. No. 9,573,935.

(30) Foreign Application Priority Data

Jul. 24, 2013 (JP) .................................. 2013-153350

(51) Int. Cl.
   *C07D 401/14* (2006.01)
   *C07D 215/54* (2006.01)
   *C07D 401/12* (2006.01)

(52) U.S. Cl.
   CPC ......... *C07D 401/14* (2013.01); *C07D 215/54* (2013.01); *C07D 401/12* (2013.01)

(58) Field of Classification Search
   None
   See application file for complete search history.

(56) References Cited

U.S. PATENT DOCUMENTS

| | | | |
|---|---|---|---|
| 9,562,060 B2 | 2/2017 | Cheng et al. |
| 9,573,935 B2 | 2/2017 | Inukai et al. |
| 9,994,549 B2 | 6/2018 | Inukai et al. |
| 2002/0048610 A1 | 4/2002 | Cima et al. |
| 2007/0060613 A1 | 3/2007 | Kim |
| 2008/0312232 A1 | 12/2008 | Kim et al. |
| 2009/0274693 A1 | 11/2009 | Gilmer et al. |
| 2009/0306103 A1 | 12/2009 | Boyer et al. |
| 2011/0053931 A1 | 3/2011 | Gaudino et al. |
| 2011/0092503 A1 | 4/2011 | Ullrich et al. |
| 2011/0118252 A1 | 5/2011 | Kim et al. |
| 2012/0070413 A1 | 3/2012 | Kim et al. |
| 2013/0142790 A1 | 6/2013 | Gilmer et al. |
| 2013/0150363 A1 | 6/2013 | Gilmer et al. |
| 2014/0018365 A1 | 1/2014 | Schultz-Fademrecht et al. |
| 2014/0206679 A1 | 7/2014 | Cheng et al. |
| 2014/0275077 A1 | 9/2014 | Dandu et al. |
| 2016/0168121 A1 | 6/2016 | Inukai et al. |
| 2017/0088542 A1 | 3/2017 | Inukai et al. |

FOREIGN PATENT DOCUMENTS

| | | |
|---|---|---|
| CN | 101528702 A | 9/2009 |
| CN | 102083824 A | 6/2011 |
| CN | 103124729 A | 5/2013 |
| JP | 2003-519698 A | 6/2003 |
| JP | 2008-539275 A | 11/2008 |
| JP | 2009-537632 A | 10/2009 |
| JP | 2009-539878 A | 11/2009 |
| JP | 2010-178651 A | 8/2010 |
| JP | 2011-517689 A | 6/2011 |

(Continued)

OTHER PUBLICATIONS

Registry (STN) [online], Jan. 16, 2001, RN 314026-41-0, [retrieval date Aug. 6, 2014], Total 1 page.

V. A. Korshunov; "Axl-dependent signalling: a clinical update", 2012 Biochemical Society, Clinical Science (2012) vol. 122, pp. 361-368.

C. Gjerdrum et al., "Axl is an essential epithelial-to-mesenchymal transition-induced regulator of breast cancer metastasis and patient survival", Proceedings of the National Academy of Sciences of the United States of America, Jan. 19, 2010, vol. 107, No. 3, pp. 1124-1129.

(Continued)

*Primary Examiner* — Brian J Davis
(74) *Attorney, Agent, or Firm* — Sughrue Mion, PLLC

(57) ABSTRACT

A compound represented by general formula (I) has a strong Axl inhibitory activity by introducing a distinctive bicyclic structure in which a saturated carbon ring is fused to a pyridone ring, and can be a therapeutic agent for Axl-related diseases, for example, cancer such as acute myeloid leukemia, melanoma, breast cancer, pancreatic cancer, and glioma, kidney diseases, immune system diseases, and circulatory system diseases (I)

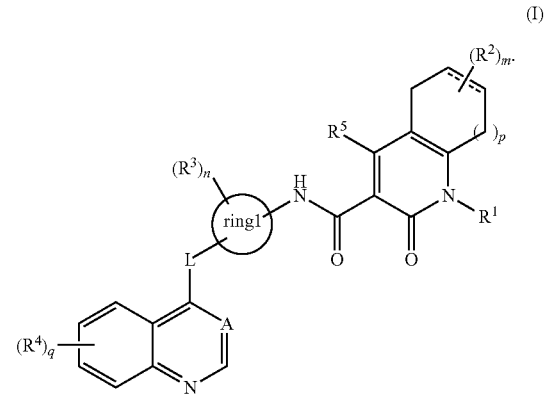

3 Claims, No Drawings

(56) References Cited

FOREIGN PATENT DOCUMENTS

| JP | 2014-533287 A | 12/2014 |
|---|---|---|
| WO | 2006116713 A1 | 11/2006 |
| WO | 2007/033196 A1 | 3/2007 |
| WO | 2007146824 A2 | 12/2007 |
| WO | 2008/048375 A1 | 4/2008 |
| WO | 2009/140549 A1 | 11/2009 |
| WO | 2009137429 A1 | 11/2009 |
| WO | 2010/039248 A1 | 4/2010 |
| WO | 2012011548 A1 | 1/2012 |
| WO | 2012028332 A1 | 3/2012 |
| WO | 2012080729 A2 | 6/2012 |
| WO | 2013074633 A1 | 5/2013 |
| WO | 2015/012298 A1 | 1/2015 |
| WO | 2015012298 A1 | 1/2015 |

OTHER PUBLICATIONS

Il-Kyoo Park et al., "Inhibition of the receptor tyrosine kinase Axl impedes activation of the FLT3 internal tandem duplication in human acute myeloid leukemia: implications for Axl as a potential therapeutic target", Blood Journal, Mar. 14, 2013, vol. 121, No. 11, Total 11 pages.
International Searching Authority, Search Report dated Aug. 19, 2014, issued in International Application No. PCT/JP2014/069419.
International Searching Authority, Written Opinion dated Aug. 19, 2014, issued in International Application No. PCT/JP2014/069419.
State Intellectual Property Office of the People's Republic of China, Communication dated Nov. 2, 2016 issued in Chinese Patent Application No. 201480041780.2.
European Intellectual Property Office, Communication dated Dec. 6, 2016 issued in European Application No. 14828976.2.
Search Report dated Feb. 9, 2016, issued by the International Searching Authority in International Application No. PCT/JP2015/086050 (PCT/ISA/210).
Written Opinion dated Feb. 9, 2016, issued by the International Searching Authority in International Application No. PCT/JP2015/086050 (PCT/ISA/237).
Zhang, et al.; "Discovery of novel type II c-Met inhibitors based on BMS-777607", European Journal of Medicinal Chemistry, vol. 80, Apr. 2014, 13 pages total.
Lovering, et al.; "Identification of Type-II Inhibitors Using Kinase Structures", Chemical Biology and Drug Design, vol. 80, No. 5, Jun. 2012, 8 pages total.
U.S. Appl. No. 15/539,530, filed Jun. 23, 2017.
Extended European Search Report dated Nov. 15, 2017, issued by the European Patent Office in European Application No. 15873185.1.
Samit K Bhattacharya et al: "Identification of novel series of pyrazole and indole-urea based DFG-out PYK2 inhibitors", Bioorganic & Medicinal Chemistry Letters, vol. 22, No. 24, Dec. 1, 2012, XP05509390, pp. 7523-7529, (7 pages total).
Allen G et al: "Identification of small molecule inhibitors of proline-rich tyrosine kinase 2 (Pyk2) with osteogenic activity in osteoblast cells", Bioorganic & Medicinal Chemistry Letters, vol. 19, No. 17, Sep. 1, 2009, XP026458526, pp. 4924-4928, (5 pages total).
Communication dated Feb. 27, 2018, issued by the USPTO in co-pending U.S. Appl. No. 15/539,530.
Carla V Rothlin et al. "TAM receptor signaling and autoimmune disease", Current Opinion in Immunology, vol. 22 2010, (pp. 740-746).
Rachel M.A. Linger et al. "TAM Receptor Tyrosine Kinases: Biologic Functions, Signaling, and Potential Therapeutic Targeting in Human Cancer", Advances in Cancer Research, 2008, (pp. 35-83).
Anette Fiebeler et al. "Growth Arrest Specific Protein 6/Axl Signaling in Human Inflammatory Renal Diseases" American Journal of Kidney Disease, vol. 43, No. 2, Feb. 2004, (pp. 286-295).
Carla V. Rothlin et al. "TAM Receptor Signaling in Immune Homeostasis" American review of Immunology, vol. 33, Jan. 14, 2015, (pp. 355-391).
Zhihui Wang et al. "Mathematical modeling in cancer drug discovery" Drug Discovery Today, vol. 19, No. 2, Feb. 2014, (pp. 145-150).
Udaya Kiran Marelli et al. "Tumor targeting via integrin ligands" Frontiers in Oncology, vol. 3, Article 222, Aug. 30, 2013, (pp. 1-12).
T. Fujimori et al. "The Axl receptor tyrosine kinase is a discriminator of macrophage function in the inflamed lung" Mucosal Immunology, vol. 8, No. 5, Sep. 2015, (pp. 1021-1030).
Anna Zagórska et al. Diversification of TAM receptor tyrosine kinase function Nature Immunology vol. 15, No. 10, Oct. 2014, (pp. 920-930).
Brooke M. VandenBrink et al. "Evaluation of CYP2C8 Inhibition in Vitro: Utility of Montelukast as a Selective CYP2C8 Probe Substrate" The American Society for Pharmacology and Experimental Therapeutics, vol. 31, No. 9, 2011, (p. 1546-1554).
Xiaoliang Wu et al. "AXL kinase as a novel target for cancer therapy" Oncotarget, vol. 5, No. 20, Oct. 16, 2014, (pp. 9546-9563).
Berge et al., "Pharmaceutical Salts", Journal of Pharmaceutical Sciences, vol. 66, No. 1, Jan. 1977, pp. 1-19, 19 pages total.
Kawaguchi et al., "Drug and crystal polymorphism", Journal of Human Environmental Engineering, vol. 4, No. 2, 2002, pp. 310-317, 10 pages total.
"Specifications and Test Methods of New Pharmaceuticals", PFSB / ELD Notification, No. 568, 2001, 25 pages total.
Ooshima, "Crystallization of Polymorphs and Pseudo-polymorphs and Its Control", Pharm Stage, vol. 6, No. 10, 2007, pp. 48-53, 9 pages total.
Takata, "API form screening and selection in drug discovery stage", Pharm Stage, vol. 6, No. 10, 2007, pp. 20-25, 10 pages total.
Yamano, "Approach to Crystal Polymorph in Process Research of New Drug", Synthetic Organic Chemistry, vol. 65, No. 9, 2007, pp. 907-913, 11 pages total.
Byrn et al., "Pharmaceutical Solids: A Strategic Approach to Regulatory Considerations", Pharmaceutical Research, vol. 12, No. 7, 1995, pp. 945-954, 10 pages total.
International Search Report dated Mar. 20, 2018 issued by the International Searching Authority in International Application No. PCT/JP2018/002250 (PCT/ISA/210).
"BG8324 Enhances Immune Checkpoint Inhibitor Efficacy in Preclinical Cancer Models" BerGenBio AS, Sep. 21, 2015 (url: https://www.bergenbio.com/bgb324-enhances-immune-checkpoint-inhibitor-efficacy-in-preclinical-cancer-models/ [retrieved Feb. 12, 2020] (Year: 2015) (1 page).
Gro Gausdal et al. "Abstract B014: BGB324, a selective small molecule inhibitor of the receptor tyrosine kinase AXL, enhances immune checkpoint inhibitor efficacy" Cancer Immunology Research, CRI-CIMT-EATI-AACR Inaugural International Cancer Immunotherapy Conference: Translating Science into Survival, Sep. 16-19, 2015, (pp. 1-4).

QUINOLINE DERIVATIVE

CROSS-REFERENCE TO RELATED PATENT APPLICATIONS

This application is a Continuation of U.S. application Ser. No. 16/237,275 filed Dec. 31, 2018, which is a Continuation of U.S. application Ser. No. 15/975,999 filed May 10, 2018, now U.S. Pat. No. 10,208,022, issued Feb. 19, 2019, which is a Continuation of U.S. application Ser. No. 15/373,091 filed Dec. 8, 2016, now U.S. Pat. No. 9,994,549, issued Jun. 12, 2018, which is a Continuation of U.S. application Ser. No. 14/906,993 filed Jan. 22, 2016, now U.S. Pat. No. 9,573,935, issued Feb. 21, 2017, which is a National Stage application under 35 U.S.C. § 371 of International Application No. PCT/JP2014/069419, filed on Jul. 23, 2014, and claims the benefit of Japanese Application No. 2013-153350, filed on Jul. 24, 2013 in the Japanese Patent Office, the disclosures of which are incorporated herein by reference in their entireties.

TECHNICAL FIELD

The present invention relates to a compound represented by general formula (I):

(I)

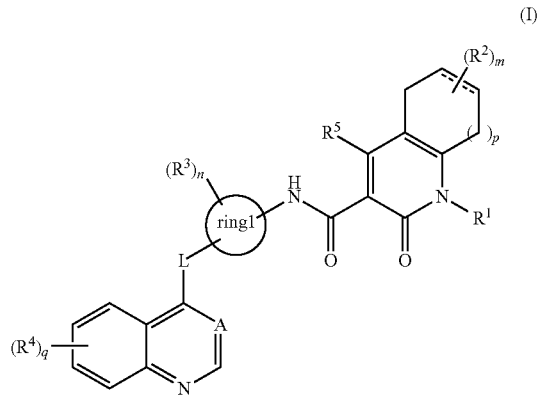

(wherein all of the symbols have the same meanings as given below), a salt thereof, a solvate thereof, an N-oxide thereof, or a prodrug thereof (hereinafter, also abbreviated as the compound of the present invention).

BACKGROUND ART

Axl (also known as: UFO, ARK, Tyrol) is a receptor tyrosine kinase belonging to a TAM family (Axl, Mer and Tyro3) cloned from tumor cells. Gas6 (growth-arrest-specific protein 6) cloned as a gene specifically expressed at the time of cell proliferation arrest is known as a ligand for Axl. Axl activated by binding of Gas6 transfers a signal via phosphorylation. Since the signal activates an Erk1/2 pathway or a PI3K/Akt pathway, the activation of Axl is known to be involved in pathologic conditions of cancers, immune system diseases, circulatory system diseases, and the like (see, Non-Patent Literature 1).

In particular, the relation between Axl and various types of cancers is well known. For example, it is known that the expression of Axl is involved in metastasis and prognosis of breast cancer (see, Non-Patent Literature 2), and that Axl is involved in the pathologic conditions of acute myeloid leukemia (AML) (see Non-Patent Literature 3). Therefore, it is considered that compounds which inhibit the activation of Axl are useful for treatment of various type of cancers, immune system diseases, and circulatory system diseases.

By the way, as prior art of the compound of the present invention, a compound represented by general formula (A):

(A)

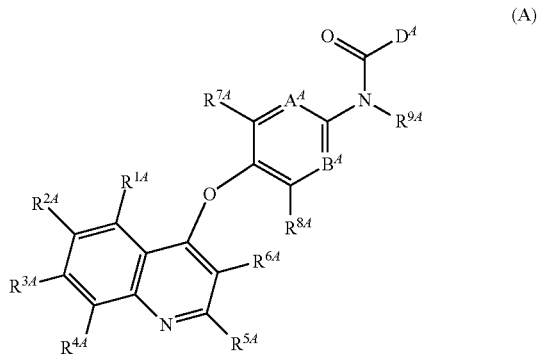

(wherein $A^A$ represents $C-R^{10A}$ and N; $B^A$ represents $C-R^{11A}$ and N; $D^A$ represents heterocycles of the following general formulae, and the like.

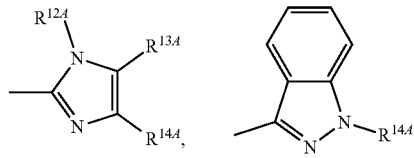

(wherein $R^{1A}$, $R^{4A}$ and $R^{8A}$ are independently —H, —F, —Cl, —Br, —I, —OH, —NH$_2$, —OCH$_3$, —OC$_2$H$_5$, or the like; $R^{2A}$ and $R^{3A}$ are independently —$R^{88A}$ or the like; $R^{5A}$ and $R^{6A}$ may be the same as each other or different from each other, and represent —H, —F, —Cl, —Br, —I, —CN, —NO$_2$, —CH$_3$, or the like; $R^{7A}$; $R^{8A}$, $R^{10A}$, and $R^{11A}$ may be the same as each other or different from each other, and represent —H, —F, —Cl, —Br, —I, —CN, —NO$_2$, —CH$_3$, or the like; $R^{9A}$ represents —H or the like; $R^{12A}$ represents —CN, phenyl, or the like; $R^{13A}$ represents —H, —F, —Cl, —Br, —I, —CN, —NO$_2$, —CH$_3$, or the like; $R^{14A}$ represents —H, —F, —Cl, —Br, —I, —NO$_2$, —CN, or the like (where the definitions of the groups are excerpted)) is known to be an Axl inhibitor (see, Non-Patent Literature 1).

Furthermore, a compound represented by general formula (B):

(B)

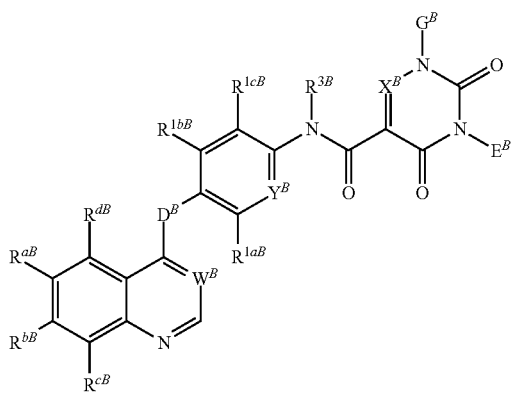

(wherein $E^B$ and $G^B$ are independently a hydrogen atom, a C1-6 alkyl group optionally substituted with one to six $R^{19B}$, a C6-11 aryl group optionally substituted with one to six $R^{19B}$ or the like; $X^B$ represents N or C—$R^{4B}$; $Y^B$ represents N or C—$R^{1dB}$; $D^B$ represents —O—, —S—, —NH— or the like; $W^B$ represents CH or N; $R^{aB}$, $R^{bB}$, $R^{cB}$, $R^{dB}$, $R^{1aB}$, $R^{1cB}$, $R^{1dB}$ and $R^{4B}$ independently represent a hydrogen atom, —$OR^{110B}$ or the like; $R^{19B}$ represents a halogen atom, —CN, or the like; and $R^{110B}$ represents a hydrogen atom, a C1-6 alkyl group optionally substituted with one to six $R^{129B}$ (where the definitions of the groups are excerpted)) is known to be an Axl inhibitor (see Patent Literature 2).

On the other hand, a compound having a quinoline skeleton and represented by the following general formula (C):

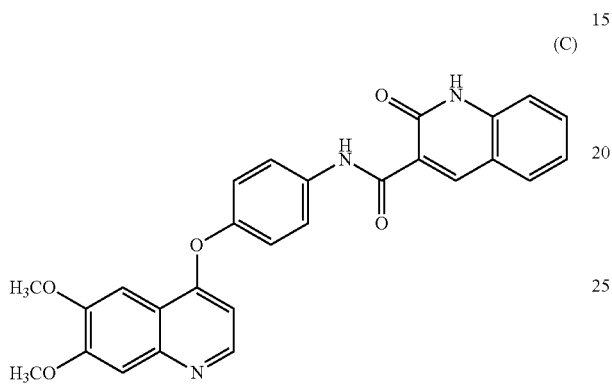

is known to have an ASK1 inhibitory activity, and be an agent for preventing and/or treating amyotrophic lateral sclerosis (ALS) (see Patent Literature 3).

Furthermore, a compound represented by general formula (D):

(wherein $R^D$ represents

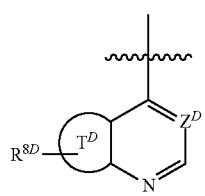

or the like; $T^D$ represents phenyl or the like; $Z^D$ represents N or $CR^{7D}$; $W^D$ represents a substituted or unsubstituted phenyl, substituted or unsubstituted 6-membered nitrogen-containing heteroaryl or the like; $X^D$ represents O, S, S(=O), or the like; $Y^D$ represents —$NR^{aD}C(=O)$—$(CR^{3D}R^{4D})_p$— or the like; $R^{aD}$ represents, a hydrogen atom, an alkyl group, or the like; and $R^{1D}$ represents

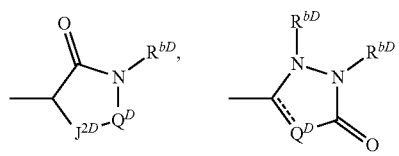

or the like; $J^{2D}$ represents O or $CR^{4aD}R^{4aD}$; $Q^D$ represents 1- to 5-membered saturated or partially unsaturated alkyl chain or the like; $R^{1D}$ represents optionally substituted phenyl or may be fused to optionally substituted 5- to 6-membered heterocycle; $R^{3D}$ and $R^{4D}$ each independently represents a hydrogen atom, an alkyl group, an aryl group, or the like; $R^{4aD}$ is absent or represents a hydrogen atom, a halogen atom, or the like (where the definitions of the groups are excerpted)) is known to be a c-Met inhibitor (see Patent Literature 4).

Furthermore, a compound represented by general formula (E):

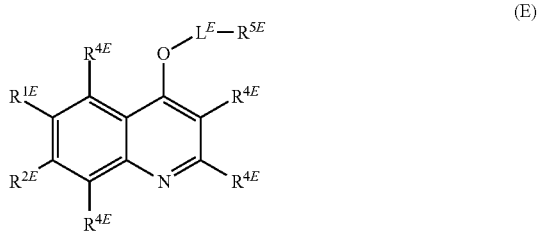

(wherein $R^{1E}$, $R^{2E}$ and $R^{4E}$ independently represent H, F, Cl, Br, I, CN, $OR^{10E}$, C1-C12 alkyl, or the like; $L^E$ represents a C3-C12 carbon ring, C6-C20 aryl, or the like; $R^{5E}$ represents —$C(=Y^E)R^{13E}$, —$C(=Y^E)R^{10E}R^{13E}$, —$NR^{10E}C(=Y^E)R^{13E}$, or the like; $R^{10E}$ represents H, C1-C12 alkyl, a C3-C12 carbon ring, a C2-C20 heterocycle, or the like; $R^{13E}$ represents H, C1-C6 alkyl, or the like; and $Y^E$ represents O or S (where the definitions of the groups are excerpted)) is known to be a c-Met inhibitor (see Patent Literature 5).

However, any of the prior art literatures neither mention nor suggest that a quinoline derivative as a compound of the present invention, having a bicyclic structure in which a saturated carbon ring is fused to a pyridone ring, represented by the following structural formula.

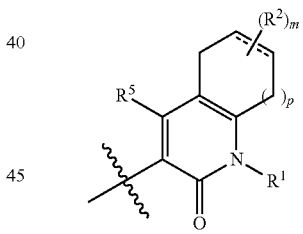

has a significant Axl inhibitory activity.

PRIOR ART LITERATURES

Patent Literatures

[Patent Literature 1] WO2012/028332
[Patent Literature 2] WO2013/074633
[Patent Literature 3] WO2012/011548
[Patent Literature 4] WO2006/116713
[Patent Literature 5] WO2007/146824

Non-Patent Literatures

[Non-Patent Literature 1] Clinical Science, Vol. 122, p. 361-368, 2012
[Non-Patent Literature 2] Proceedings of the national academy of sciences of the United States of America, Vol. 107, No. 3, p. 1124-1129, 2010

[Non-Patent Literature 3] Blood, Vol. 121, p. 2064-2073, 2013

SUMMARY OF INVENTION

Technical Problem

A problem to be solved by the present invention is to find a compound having an Axl inhibitory activity, which is useful for treatment of cancer such as AML, and to provide the compound as pharmaceuticals whose side effects are reduced.

Solution to Problem

In order to solve the above-mentioned problem, the inventors of the present invention have keenly studied to find a compound strongly inhibiting Axl. As a result, surprisingly, the inventors have found that a bicyclic structure, in which a saturated carbon ring is fused to a pyridone ring, represented by the following structural formula:

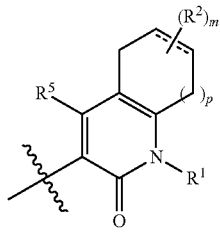

improves the Axl inhibitory activity, and have completed the present invention.

That is to say, the present invention relates to:
[1] a compound represented by general formula (I)

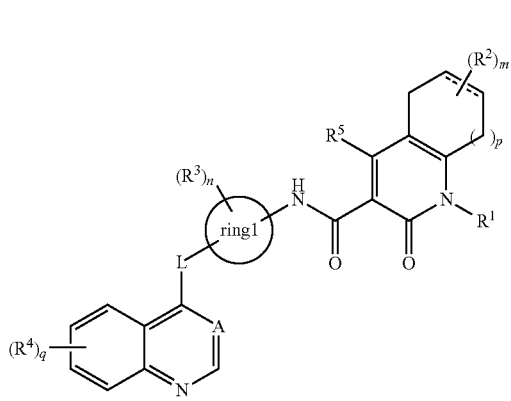

[wherein $R^1$ represents (1) a C1-8 alkyl group optionally substituted with one to five $R^{11}$, (2) a C3-7 carbon ring optionally substituted with one to five $R^{12}$, or (3) a 4- to 7-membered heterocycle optionally substituted with one to five $R^{13}$, wherein when the C1-8 alkyl group represented by $R^1$ is a branched alkyl group, the C1-3 alkyl group branched from the same carbon atom, together with the carbon atom bound thereto, optionally forms a saturated C3-7 carbon ring,
$R^2$ represents (1) a C1-4 alkyl group, (2) a halogen atom, (3) a C1-4 haloalkyl group, (4) an oxo group, (5) an —$OR^{21}$ group, or (6) an =$NR^{22}$ group, $R^3$ represents (1) a C1-4 alkyl group, (2) a halogen atom, or (3) a C1-4 haloalkyl group,
$R^4$ represents (1) a C1-4 alkoxy group, (2) a C1-4 haloalkyl group, (3) an —$OR^{41}$ group, (4) a C1-4 alkyl group, (5) a C2-4 alkenyloxy group, or (6) a C2-4 alkynyloxy group,
$R^5$ represents (1) a hydrogen atom, (2) a C1-4 alkyl group, (3) a halogen atom, (4) a C1-4 haloalkyl group, or (5) an —$OR^{21}$ group,
$R^{11}$ represents (1) an —$OR^{101}$ group, (2) an $SO_2R^{102}$ group, (3) an $NR^{103}R^{104}$ group, or (4) a C3-7 carbon ring optionally substituted with one to three halogen atoms,
$R^{12}$ represents (1) a C1-8 alkyl group optionally substituted with a hydroxyl group, or (2) a halogen atom,
$R^{13}$ represents (1) a C1-8 alkyl group optionally substituted with a hydroxyl group, or (2) a halogen atom,
$R^{21}$ represents (1) a hydrogen atom, or (2) a C1-4 alkyl group,
$R^{22}$ represents (1) a hydroxyl group, or (2) C1-4 alkoxy group,
$R^{41}$ represents
  (1) a hydrogen atom;
  (2) a C1-8 alkyl group substituted with one to two substituents selected from the group consisting of (a) 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group;
  (3) a C2-8 alkenyl group substituted with one to two substituents selected from the group consisting of (a) 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group; or
  (4) a C2-8 alkynyl group substituted with one to two substituents selected from the group consisting of (a) 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group,
$R^{101}$ represents (1) a hydrogen atom, or (2) a C1-4 alkyl group,
$R^{102}$ represents (1) a hydrogen atom, or (2) a C1-4 alkyl group,
$R^{103}$ and $R^{104}$ each independently represents (1) a hydrogen atom, or (2) a C1-4 alkyl group,
$R^{401}$ and $R^{402}$ each independently represents (1) a hydrogen atom, or (2) a C1-4 alkyl group,
$R^{403}$ represents (1) a hydrogen atom, or (2) a C1-4 alkyl group,
A represents (1) CH, or (2) a nitrogen atom,
L represents (1) —O—, (2) —NH—, (3) —C(O)—, (4) —$CR^6R^7$—, (5) —S—, (6) —S(O)—, or (7) —S(O)$_2$—, $R^6$ and $R^7$ each independently represents (1) a hydrogen atom, (2) a halogen atom, (3) a C1-4 alkyl group, (4) a hydroxyl group, or (5) $NH_2$,
ring1 represents a 5- to 7-membered cyclic group,
~~~~~~ represents a single bond or a double bond,
m is an integer from 0 to 5,
n is an integer from 0 to 5,
p is an integer from 0 to 2,
q is an integer from 0 to 4,
when m is two or more, a plurality of $R^2$ may be the same as or different from each other, and when two of $R^2$ represent a C1-3 alkyl group and are on the same carbon atom, the $R^2$, together with a carbon atom bound thereto, may form a saturated C3-7 carbon ring, when n is two or more, a plurality of $R^3$ may be the same as or different from each other, and when q is two or more, a plurality of $R^4$ may be the same as or different from each other], a salt thereof, a solvate thereof, an N-oxide thereof, or a prodrug thereof,

[2] the compound according to the above-mentioned [1], wherein m is one or more, and one of two $R^2$ is necessarily an oxo group,

[3] the compound according to the above-mentioned [1] or [2], wherein the ring1 is benzene or pyridine,

[4] the compound according to any one of the above-mentioned [1] to [3], wherein L is (1) —O—, (2) —NH—, or (3) —C(O)—, [5] the compound according the above-mentioned [1], which is represented by general formula (I-1)

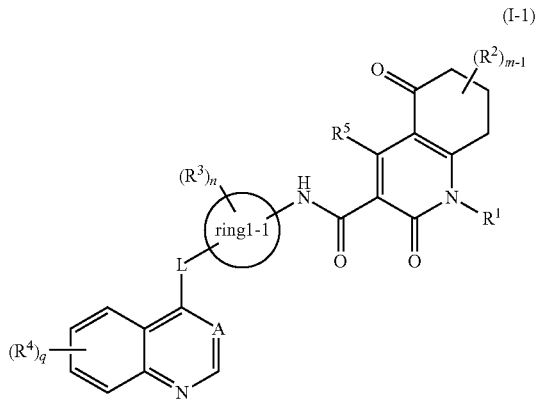

(I-1)

[wherein $R^{2-1}$ represents (1) a C1-4 alkyl group, (2) a halogen atom, (3) a C1-4 haloalkyl group, (4) an —$OR^{21}$ group, or (5) an =$NR^{22}$ group, m-1 is an integer from 0 to 4, $L^1$ is (1) —O—, (2) —NH—, or (3) —C(O)—, ring1-1 represents benzene or pyridine, when m-1 is two or more, a plurality of $R^{2-1}$ may be the same as or different from each other, and when two of $R^{2-1}$ represent a C1-3 alkyl group and are on the same carbon atom, the $R^{2-1}$, together with a carbon atom bound thereto, may form a saturated C3-7 carbon ring, and other symbols have the same meanings as defined in the above-mentioned,

[6] the compound according to any one of the above-mentioned [1] to [5], which is: (1) N-{5-[(6,7-dimethoxy-4-quinolinyl)oxy]-2-pyridinyl}-2,5-dioxo-1-phenyl-1,2,5,6,7,8-hexahydro-3-quinolinecarboxamide, (2) N-{5-[(6,7-dimethoxy-4-quinolinyl)oxy]-2-pyridinyl}-7,7-dimethyl-2,5-dioxo-1-phenyl-1,2,5,6,7,8-hexahydro-3-quinolinecarboxamide, (3) N-{5-[(6,7-dimethoxy-4-quinolinyl)oxy]-2-pyridinyl}-1-(2,2-dimethylpropyl)-2,5-dioxo-1,2,5,6,7,8-hexahydro-3-quinolinecarboxamide, (4) N-[5-({7-[3-(4-morpholinyl)propoxy]-4-quinolinyl}oxy)-2-pyridinyl]-2,5-dioxo-1-phenyl-1,2,5,6,7,8-hexahydro-3-quinolinecarboxamide, (5) N-{4-[(6,7-dimethoxy-4-quinolinyl)oxy]-3-fluorophenyl}-2,5-dioxo-1-phenyl-1,2,5,6,7,8-hexahydro-3-quinolinecarboxamide, (6) N-{4-[(6,7-dimethoxy-4-quinolinyl)oxy]phenyl}-2,5-dioxo-1-phenyl-1,2,5,6,7,8-hexahydro-3-quinolinecarboxamide, (7) N-{5-[(6,7-dimethoxy-4-quinolinyl)oxy]-2-pyridinyl}-1-(4-fluorophenyl)-2,5-dioxo-1,2,5,6,7,8-hexahydro-3-quinolinecarboxamide, (8) N-{5-[(6,7-dimethoxy-4-quinolinyl)oxy]-2-pyridinyl}-1-(3-fluorophenyl)-2,5-dioxo-1,2,5,6,7,8-hexahydro-3-quinolinecarboxamide, (9) N-{5-[(6,7-dimethoxy-4-quinolinyl)oxy]-2-pyridinyl}-1-(2-fluorophenyl)-2,5-dioxo-1,2,5,6,7,8-hexahydro-3-quinolinecarboxamide, (10) N-{5-[(6,7-dimethoxy-4-quinazolinyl)oxy]-2-pyridinyl}-2,5-dioxo-1-phenyl-1,2,5,6,7,8-hexahydro-3-quinolinecarboxamide, (11) N-{5-[(6,7-dimethoxy-4-quinazolinyl)oxy]-2-pyridinyl}-1-(4-fluorophenyl)-2,5-dioxo-1,2,5,6,7,8-hexahydro-3-quinolinecarboxamide, (12) N-{5-[(6,7-dimethoxy-4-quinolinyl)oxy]-2-pyridinyl}-1-[(2S)-1-hydroxy-3-methyl-2-butanyl]-2,5-dioxo-1,2,5,6,7,8-hexahydro-3-quinolinecarboxamide, (13) N-{4-[(6,7-dimethoxy-4-quinolinyl)oxy]-3-fluorophenyl}-1-(3-fluorophenyl)-2,5-dioxo-1,2,5,6,7,8-hexahydro-3-quinolinecarboxamide, (14) N-{5-[(6,7-dimethoxy-4-quinolinyl)oxy]-2-pyridinyl}-6,6-dimethyl-2,5-dioxo-1-phenyl-1,2,5,6,7,8-hexahydro-3-quinolinecarboxamide, (15) N-[5-({6-methoxy-7-[3-(4-morpholinyl)propoxy]-4-quinolinyl}oxy)-2-pyridinyl]-2,5-dioxo-1-phenyl-1,2,5,6,7,8-hexahydro-3-quinolinecarboxamide, (16) N-(5-{[7-(3-hydroxy-3-methylbutoxy)-6-methoxy-4-quinolinyl]oxy}-2-pyridinyl)-2,5-dioxo-1-phenyl-1,2,5,6,7,8-hexahydro-3-quinolinecarboxamide, or (17) N-[5-({6-methoxy-7-[3-(1-pyrrolidinyl)propoxy]-4-quinolinyl}oxy)-2-pyridinyl]-2,5-dioxo-1-phenyl-1,2,5,6,7,8-hexahydro-3-quinolinecarboxamide,

[7] a pharmaceutical composition containing a compound represented by general formula (I) as defined in the above-mentioned [1], a salt thereof, a solvate thereof, an N-oxide thereof, or a prodrug thereof,

[8] the pharmaceutical composition according to the above-mentioned [7], which is an Axl inhibitor,

[9] the pharmaceutical composition according to the above-mentioned [7], which is an agent for preventing and/or treating an Axl-related disease,

[10] the pharmaceutical composition according to the above-mentioned [9], wherein the Axl-related diseases includes cancer, kidney diseases, immune system diseases, or circulatory system diseases,

[11] the pharmaceutical composition according to the above-mentioned [10], wherein the cancer is acute myeloid leukemia, chronic myeloid leukemia, acute lymphatic leukemia, melanoma, breast cancer, pancreatic cancer, glioma, esophageal adenocarcinoma, large intestine cancer, renal cell carcinoma, thyroid cancer, non-small cell lung cancer, prostate cancer, stomach cancer, liver cancer, uveal malignant melanoma, ovarian cancer, endometrial cancer, lymphoma, head and neck cancer, or sarcoma,

[12] the pharmaceutical composition according to the above-mentioned [7], which is a metastasis suppressing agent for cancer cells,

[13] a method for preventing and/or treating an Axl-related disease, the method including administering an effective amount of a compound represented by general formula (I) as defined in the above-mentioned [1], a salt thereof, a solvate thereof, an N-oxide thereof, or a prodrug thereof, to a mammal,

[14] a compound represented by general formula (I) according to the above-mentioned [1], a salt thereof, a solvate thereof, an N-oxide thereof, or a prodrug, for preventing and/or treating an Axl-related disease, and

[15] use of a compound represented by general formula (I), a salt thereof, a solvate thereof, an N-oxide thereof, or a prodrug, as defined in the above-mentioned [1], to manufacture an agent for preventing and/or treating an Axl-related disease.

Effects of Invention

A compound of the present invention has a strong Axl inhibitory activity, has an Axl-selective inhibitory activity to a specific kinase, and has reduced CYP inhibitory effect, and therefore is useful as a therapeutic drug for acute myeloid leukemia or the like, has less side effect and has little concern about drug interaction.

DESCRIPTION OF EMBODIMENTS

The present invention will be described in detail hereinafter.

In the present invention, a halogen atom denotes a fluorine atom, a chlorine atom, a bromine atom, and an iodine atom.

In the present invention, the C1-8 alkyl group includes a straight or branched C1-8 alkyl group. Examples thereof include methyl, ethyl, propyl, butyl, pentyl, hexyl, heptyl, octyl, isopropyl, isobutyl, sec-butyl, tert-butyl, and an isomer thereof.

In the present invention, the C1-4 alkyl group includes a straight or branched C1-4 alkyl group. Examples thereof include methyl, ethyl, propyl, butyl, isopropyl, isobutyl, sec-butyl, and tert-butyl.

In the present invention, the C1-3 alkyl group includes a straight or branched C1-3 alkyl group. Examples thereof include a methyl group, an ethyl group, a propyl group, and an isopropyl.

In the present invention, the C1-4 haloalkyl group denotes, for example, a fluoromethyl group, a chloromethyl group, a bromomethyl group, an iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group, and a 4-bromobutyl group.

In the present invention, the C2-8 alkenyl group denotes, for example, a vinyl group, a propenyl group, a butenyl group, a pentenyl group, a hexenyl group, a heptenyl group, and a octenyl group, and an isomer thereof, and the like.

In the present invention, the C2-8 alkynyl group denotes, for example, an ethynyl group, a propynyl group, a butynyl group, a pentynyl group, a hexynyl group, a heptynyl group, an octynyl group, and an isomer thereof.

In the present invention, examples of the C1-4 alkoxy group include a methoxy group, an ethoxy group, a propoxy group, an isopropoxy group, a butoxy group, an isobutoxy group, a sec-butoxy group, or a tert-butoxy group.

In the present invention, the C2-4 alkenyloxy group denotes, for example, vinyloxy, propenyloxy, butenyloxy, and an isomer thereof.

In the present invention, the C2-4 alkynyloxy group denotes, for example, ethynyloxy, propynyloxy, butynyloxy, and an isomer thereof.

In the present invention, the C3-7 carbon ring denotes a C3-7 monocyclic carbon ring, and a carbon ring which may be partially or completely saturated, and examples thereof include cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene, or benzene ring.

In the present invention, the C5-7 carbon ring denotes a C5-7 monocyclic carbon ring, and a carbon ring which may be partially or completely saturated, and examples thereof include cyclopentane, cyclohexane, cycloheptane, cyclopentene, cyclohexene, cycloheptene, cyclopentadiene, cyclohexadiene, cycloheptadiene, or benzene ring.

In the present invention, examples of the saturated C3-7 carbon ring include cyclopropane, cyclobutane, cyclopentane, cyclohexane, and cycloheptane.

In the present invention, the 4- to 7-membered heterocycle denotes 4- to 7-membered monocyclic heterocycle, which includes one to five heteroatoms selected from an oxygen atom, a nitrogen atom and a sulfur atom, and a part or all of which is saturated. Example thereof include azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxetan, dihydrofuran, tetrahydrofuran, dihydropyran, tetrahydropyran, dihydrooxepine, tetrahydrooxepine, perhydrooxepine, thietane, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole, (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, or thiadiazepin ring.

In the present invention, the 5- to 7-membered cyclic group denotes C5-7 carbon ring and 5- to 7-membered heterocycle. Herein, the C5-7 carbon ring has the same meaning as defined above, the 5- to 7-membered heterocycle includes 5- to 7-membered unsaturated heterocycle and 5- to 7-membered saturated heterocycle. Examples of 5- to 7-membered heterocycle include pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepin, tetrahydrothiepin, perhydrothiepin, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole, (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepin, tetrahydrothiadiazepin, perhydrothiadiazepin, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepin, oxazole, isoxazole, thiazole, isothiazole, furazan, oxadiazole, oxazine, oxadiazine, oxazepine, oxadiazepine, thiadiazole, thiazine, thiadiazine, thiazepine, or thiadiazepin ring.

In the present invention, the 6-membered cyclic group denotes C6 carbon ring and 6-membered heterocycle. Examples thereof include cyclohexane, cyclohexene, cyclohexadiene, benzene, pyridine, pyrazine, pyrimidine, pyridazine, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, oxathiane, dioxane, and dithiane ring.

In the present invention, "when the C1-8 alkyl group represented by $R^1$ is a branched alkyl group, the C1-3 alkyl group branched from the same carbon atom optionally forms a saturated C3-7 carbon ring together" denotes that in a partial structure of the following general formula (I):

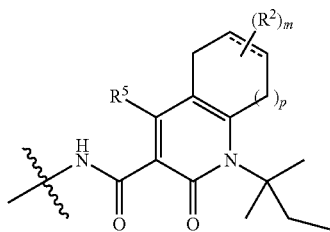

(wherein all of the symbols have the same meanings as defined above), for example, when $R^1$ is a branched alkyl chain as represented in the above-mentioned general formula, the alkyl chain branched from the same carbon atom, together with the carbon atom bound thereto, forms a saturated carbon ring, as shown in the following general formula:

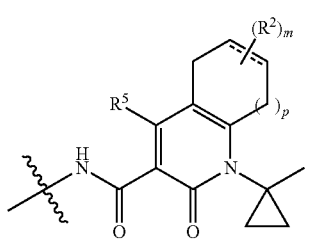

(wherein all of the symbols have the same meanings as defined above).

In the present invention, "when two of $R^2$ represent a C1-3 alkyl group and are on the same carbon atom, the $R^2$, together with a carbon atom bound thereto, may form a saturated C3-7 carbon ring" denotes that in a partial structure of the following general formula (I):

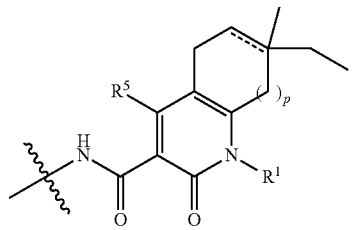

(wherein all of the symbols have the same meanings as defined above), for example, when $R^2$ is an alkyl group as represented in the above-mentioned general formula and are on the same carbon atom, the $R^2$, together with a carbon atom bound thereto, forms a saturated carbon ring, as shown in the following general formula:

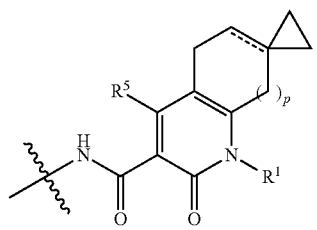

(wherein all of the symbols have the same meanings as defined above).

In the present invention, "when two of $R^{2-1}$ represent a C1-3 alkyl group and are on the same carbon atom, the $R^{2-1}$, together with a carbon atom bound thereto, may form a saturated C3-7 carbon ring" has the same definition as that for $R^2$ in the phrase: "when two of $R^2$ represent a C1-3 alkyl group and are on the same carbon atom, the $R^2$, together with a carbon atom bound thereto, may form a saturated C3-7 carbon ring."

In the present invention, it is preferable that m is one or more, and one of $R^2$ is necessarily an oxo group.

In the present invention, it is preferable that A is CH.

In the present invention, it is preferable that $R^4$ is a C1-4 alkoxy group or an $—OR^{41}$ group.

In the present invention, it is preferable that L is —O—, —NH—, or —C(O)—.

In the present invention, ring1 is preferably a 6-membered cyclic group, and more preferably benzene or pyridine.

In the present invention, it is preferable that the compound represented by general formula (I) is a compound represented by general formula (I-1):

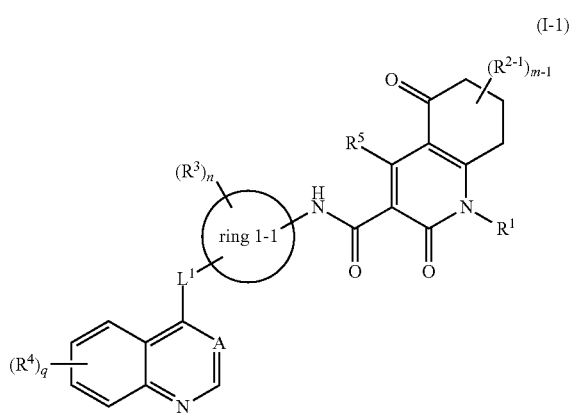

(I-1)

(wherein all of the symbols have the same meanings as defined above).

In the present invention, it is preferable that two binding arms in the ring1 and ring1-1 are bound to a para position.

In the present invention, in general formula (I-1), A is preferably CH, and $R^4$ is preferably a C1-4 alkoxy group or an —$OR^{41}$ group.

In the present invention, preferable compounds preferably include the compounds described in Examples, and the following (1) to (17) are more preferable: (1) N-{5-[(6,7-dimethoxy-4-quinolinyl)oxy]-2-pyridinyl}-2,5-dioxo-1-phenyl-1,2,5,6,7,8-hexahydro-3-quinolinecarboxamide, (2) N-{5-[(6,7-dimethoxy-4-quinolinyl)oxy]-2-pyridinyl}-7,7-dimethyl-2,5-dioxo-1-phenyl-1,2,5,6,7,8-hexahydro-3-quinolinecarboxamide, (3) N-{5-[(6,7-dimethoxy-4-quinolinyl)oxy]-2-pyridinyl}-1-(2,2-dimethylpropyl)-2,5-dioxo-1,2,5,6,7,8-hexahydro-3-quinolinecarboxamide, (4) N-[5-({7-[3-(4-morpholinyl)propoxy]-4-quinolinyl}oxy)-2-pyridinyl]-2,5-dioxo-1-phenyl-1,2,5,6,7,8-hexahydro-3-quinolinecarboxamide, (5) N-{4-[(6,7-dimethoxy-4-quinolinyl)oxy]-3-fluorophenyl}-2,5-dioxo-1-phenyl-1,2,5,6,7,8-hexahydro-3-quinolinecarboxamide, (6) N-{4-[(6,7-dimethoxy-4-quinolinyl)oxy]phenyl}-2,5-dioxo-1-phenyl-1,2,5,6,7,8-hexahydro-3-quinolinecarboxamide, (7) N-{5-[(6,7-dimethoxy-4-quinolinyl)oxy]-2-pyridinyl}-1-(4-fluorophenyl)-2,5-dioxo-1,2,5,6,7,8-hexahydro-3-quinolinecarboxamide, (8) N-{5-[(6,7-dimethoxy-4-quinolinyl)oxy]-2-pyridinyl}-1-(3-fluorophenyl)-2,5-dioxo-1,2,5,6,7,8-hexahydro-3-quinolinecarboxamide, (9) N-{5-[(6,7-dimethoxy-4-quinolinyl)oxy]-2-pyridinyl}-1-(2-fluorophenyl)-2,5-dioxo-1,2,5,6,7,8-hexahydro-3-quinolinecarboxamide, (10) N-{5-[(6,7-dimethoxy-4-quinazolinyl)oxy]-2-pyridinyl}-2,5-dioxo-1-phenyl-1,2,5,6,7,8-hexahydro-3-quinolinecarboxamide, (11) N-{5-[(6,7-dimethoxy-4-quinazolinyl)oxy]-2-pyridinyl}-1-(4-fluorophenyl)-2,5-dioxo-1,2,5,6,7,8-hexahydro-3-quinolinecarboxamide, (12) N-{5-[(6,7-dimethoxy-4-quinolinyl)oxy]-2-pyridinyl}-1-[(2S)-1-hydroxy-3-methyl-2-butanyl]-2,5-dioxo-1,2,5,6,7,8-hexahydro-3-quinolinecarboxamide, (13) N-{4-[(6,7-dimethoxy-4-quinolinyl)oxy]-3-fluorophenyl}-1-(3-fluorophenyl)-2,5-dioxo-1,2,5,6,7,8-hexahydro-3-quinolinecarboxamide, (14) N-{5-[(6,7-dimethoxy-4-quinolinyl)oxy]-2-pyridinyl}-6,6-dimethyl-2,5-dioxo-1-phenyl-1,2,5,6,7,8-hexahydro-3-quinolinecarboxamide, (15) N-[5-({6-methoxy-7-[3-(4-morpholinyl)propoxy]-4-quinolinyl}oxy)-2-pyridinyl]-2,5-dioxo-1-phenyl-1,2,5,6,7,8-hexahydro-3-quinolinecarboxamide, (16) N-(5-{[7-(3-hydroxy-3-methylbutoxy)-6-methoxy-4-quinolinyl]oxy}-2-pyridinyl)-2,5-dioxo-1-phenyl-1,2,5,6,7,8-hexahydro-3-quinolinecarboxamide, (17) N-[5-({6-methoxy-7-[3-(1-pyrrolidinyl)propoxy]-4-quinolinyl}oxy)-2-pyridinyl]-2,5-dioxo-1-phenyl-1,2,5,6,7,8-hexahydro-3-quinolinecarboxamide.

[Isomer]

In the present invention, unless specifically directed, all of the isomers are included. For example, an alkyl group includes straight chain and branched chain groups. In addition, all of geometrical isomers of double bonds, rings, and fused rings (E-, Z-, cis-, trans-isomers), optical isomers by the presence of an asymmetric carbon atom (R-, S-isomer, α-, β-configurations, enantiomers, diastereomers), optical active isomers having optical rotation property (D, L, d, l-isomers), polar isomers according to chromatographic separation (more polar isomer, less polar isomer), equilibrium compound, rotamers, mixtures thereof at any rate, and racemic mixtures are included in the present invention. Furthermore, the present invention also encompasses all isomers by tautomers.

Furthermore, the optical isomer of the present invention is not only limited to an optical isomer having purity of 100%, but also may include other optical isomers having purity of less than 50%.

In the present invention, unless otherwise noted, as apparent to a person skilled in the art, a symbol:

represents binding toward the back side of the plane of the paper (that is to say, the α-configuration), represents binding toward the front side of the plane of the paper (that is to say, the β-configuration), and represents α-configuration, β-configuration or an arbitrary mixture thereof.

The compound represented by general formula (I) is converted into a corresponding salt by the well-known method. A salt is preferably a water-soluble salt. Examples of a suitable salt include salts of an alkali metal (potassium, sodium, and the like), salts of an alkaline earth metal (calcium, magnesium, and the like), ammonium salts, or salts of a pharmaceutically acceptable organic amine (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, and the like), acid addition salts (inorganic acid salts (hydrochloride, hydrobromide, hydroiodide, sulfate, phosphate, nitrate, and the like), organic acid salts (acetate, trifluoro acetate, lactate, tartrate, oxalate, fumarate, maleate, benzoate, citrate, methanesulfonate, ethanesulfonate, benzenesulfonate, toluenesulfonate, isethionate, glucuronate, gluconate, and the like).

The compound represented by general formula (I) and a salt thereof can be also converted into a solvate. It is preferable that the solvate is low-toxic and water-soluble. Examples of a suitable solvate include solvates with water, or an alcoholic solvent (for example, ethanol).

The N-oxide of the compound represented by general formula (I) denotes compounds represented by general formula (I) in which a nitrogen atom is oxidized. Furthermore, the N-oxide of the compound represented by general formula (I) may be salts of alkali (earth) metal salt, ammonium salt, organic amine salt, and acid addition salt mentioned above.

The prodrug of the compound represented by general formula (I) denotes a compound which is converted to a compound represented by general formula (I) by a reaction with an enzyme, stomach acid, and the like, in a living body. Prodrugs of the compound represented by general formula (I) include: compounds in which the hydroxyl group is acylated, alkylated, phosphorylated, or borated, when the compounds represented by general formula (I) have a hydroxyl group (for example, the compounds represented by general formula (I) in which the hydroxyl group is acetylated, palmitoylated, propanoylated, pivaloylated, succinylated, fumarylated, alanylated, or dimethylaminomethylcarbonylated); and compounds in which the carboxyl group is esterified or amidated (for example, compounds represented by general formula (I) in which the carboxyl group is made into ethyl ester, isopropyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methylamide, and the like). These compounds can be produced by well-known methods. Furthermore, the prodrug of the compound represented by general formula (I) may be hydrate or non-hydrate. Furthermore, the prodrug of the compound represented by general formula (I) may be a compound which is changed into the compound represented by general formula (I) under the physiological condition, as described in "Development of Medicaments", vol. 7 "Molecular Design", p. 163-198, published by Hirokawa Shoten in 1990. In addition, the compound represented by general formula (I) may be labeled with an isotope thereof (for example, $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, and the like).

[Process for Producing Compound of the Present Invention]

The compound of the present invention can be produced by the well-known methods, for example, the method described in Comprehensive Organic Transformations: A Guide to Functional Group Preparations, 2nd Edition (Richard C. Larock, John Wiley & Sons Inc, 1999), or methods described in Examples, or the like, with appropriate modification and in combination thereof.

A compound represented by general formula (I) wherein L is an oxygen atom, and $R^2$ is an oxo group, that is, a compound represented by general formula (I-A):

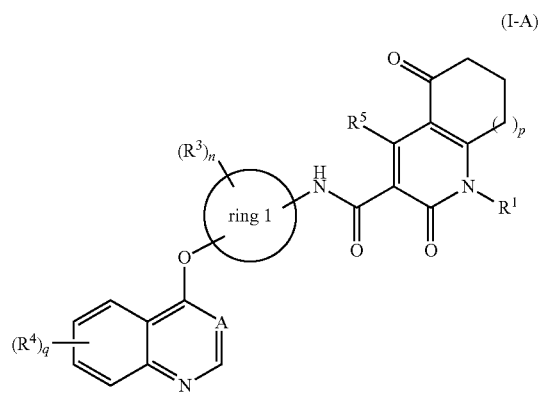

(I-A)

(wherein all of the symbols have the same meanings as defined above) can be produced by the process represented by the following reaction process schemes 1 and 2:

Reaction process scheme 1

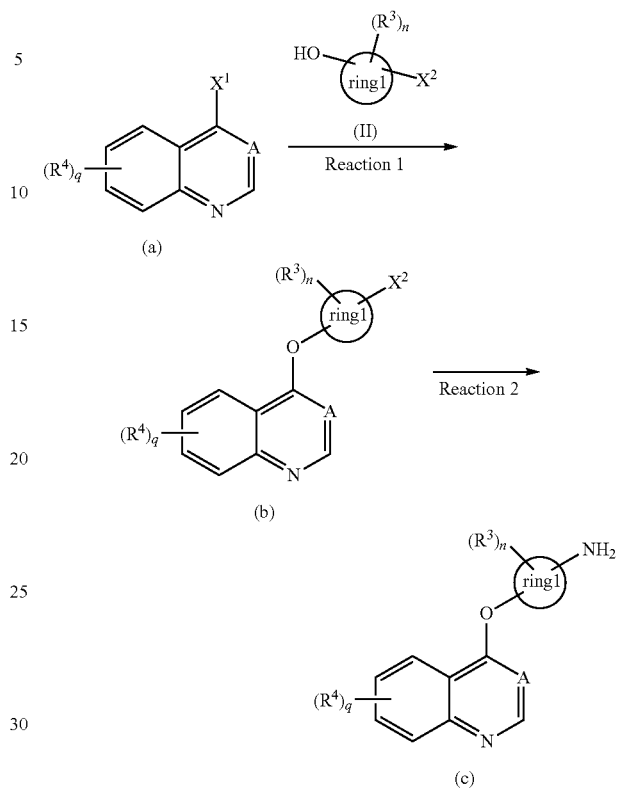

(wherein each of $X^1$ and $X^2$ independently represents a halogen atom, $X^1$ and $X^2$ may be the same as or different from each other, and the other symbols have the same meanings as defined above).

In the reaction process scheme 1, the reaction 1 can be carried out by subjecting a compound represented by general formula (a) and a compound represented by general formula (II) to the aromatic nucleophilic substitution reaction. The aromatic nucleophilic substitution reaction is well known, and is carried out, for example, in an organic solvent (chlorobenzene, N,N-dimethyl sulfoxide, N,N-dimethyl acetamide, N,N-dimethylformamide, chloroform, dichloromethane, diethyl ether, tetrahydrofuran, methyl t-butyl ether, and the like), in the presence or absence of a catalyst (4-dimethylaminopyridine (DMAP) and the like), and in the presence or absence of a base (sodium hydride, triethylamine, cesium carbonate, and the like), at 0 to 200° C.

In the reaction process scheme 1, the reaction 2 is carried out by reacting a compound represented by general formula (b) in an organic solvent (tetrahydrofuran, and the like), in the presence of a palladium catalyst (tris(dibenzylideneacetone)dipalladium(0) chloroform complex, and the like), in the presence of a base (lithium bis(trimethylsilyl)amide (LHMDS), potassium bis(trimethylsilyl)amide (KHMDS), sodium bis(trimethylsilyl)amide (NaHMDS), and the like), a phosphine compound (2-dicyclohexylphosphino-2',6'-dimethoxybiphenyl (S-Phos), tri-tert-butylphosphine (P(t-Bu)$_3$), and the like) at 0 to 100° C., and then reacting by adding inorganic acid (hydrochloric acid, hydrobromic acid, hydroiodic acid, sulfuric acid, phosphoric acid, nitric acid, and the like) at 0 to 150° C. Alternatively, the production method for aryl amine described in Organic Letters, Vol 3, No. 17, p. 2729-2732, 2001 can be employed.

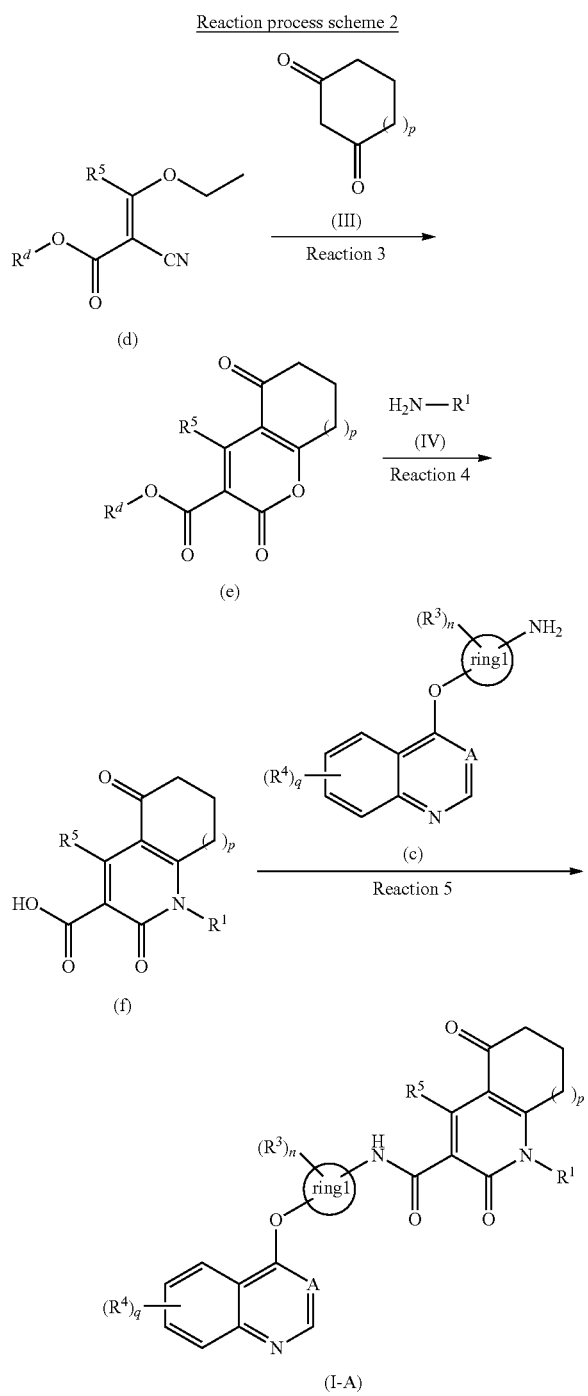

(wherein $R^d$ represents a C1-4 alkyl group, and the other symbols have the same meanings as defined above).

In the reaction process scheme 2, the reaction 3 is carried out by a reaction of a compound represented by general formula (d) and a compound represented by general formula (III). The reaction is well known, and, for example, can be carried out at 0 to 100° C. in an organic solvent (N,N-dimethyl formamide and the like), in the presence of a base (tert-butoxy potassium and the like).

In the reaction process scheme 2, the reaction 4 can be carried out by subjecting a compound represented by general formula (e) and a compound represented by general formula (IV) to addition reaction. The reaction is well known, and, for example, can be carried out by reacting at 0 to 100° C. in an alcohol solvent (methanol, ethanol, and the like).

In the reaction process scheme 2, the reaction 5 can be carried out by using and subjecting the compound represented by general formula (c) and the compound represented by general formula (f) to an amidation reaction. The amidation reaction is well known, and examples thereof include:

(1) a method using an acid halide, (2) a method using a mixed acid anhydride, and (3) a method using a condensing agent.

These methods are specifically described below:

(1) The method using an acid halide is carried out, for example, by reacting a carboxylic acid with an acid halogenating agent (oxalyl chloride, thionyl chloride, and the like) in an organic solvent (chloroform, dichloromethane, diethyl ether, tetrahydrofuran, and the like) at −20° C. to reflux temperature, and then reacting the obtained acid halide in the presence of a base (pyridine, triethylamine, dimethylaniline, dimethylaminopyridine, diisopropylethylamine, and the like) in amine and an organic solvent (chloroform, dichloromethane, diethyl ether, tetrahydrofuran, and the like) at 0 to 40° C. Additionally, the method can be also carried out by reacting the obtained acid halide with an amine at 0 to 40° C. by using an alkaline aqueous solution (sodium bicarbonate water or sodium hydroxide solution, and the like) in an organic solvent (dioxane, tetrahydrofuran, and the like).

(2) The method using a mixed acid anhydride is carried out, for example, by reacting carboxylic acid with an acid halide (pivaloyl chloride, tosyl chloride, mesyl chloride, and the like) or an acid derivative (ethyl chloroformate, isobutyl chloroformate, and the like) in the presence of a base (pyridine, triethylamine, dimethylaniline, dimethylaminopyridine, diisopropylethylamine, and the like) in an organic solvent (chloroform, dichloromethane, diethyl ether, tetrahydrofuran, and the like) or in the absence of any solvent at 0 to 40° C., and then reacting the obtained mixed acid anhydride with amine in an organic solvent (chloroform, dichloromethane, diethyl ether, tetrahydrofuran, and the like) at 0 to 40° C.

(3) The method using a condensing agent is carried out, for example, by reacting a carboxylic acid with an amine in an organic solvent (chloroform, dichloromethane, dimethyl formamide, diethyl ether, tetrahydrofuran, and the like) or in the absence of any solvent at 0 to 40° C. in the presence or absence of a base (diisopropylethylamine (DIPEA), pyridine, triethylamine, dimethylaniline, dimethylaminopyridine, and the like), using a condensing agent (O-(7-Aza-1-benzotriazolyl)-N,N,N',N'-tetramethyluronium hexafluorophosphate (HATU), (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methyl-pyridiniumiodide, 1-propylphosphonic acid cyclic anhydride (PPA), and the like) and using, or not using, 1-hydroxybenztriazole (HOBt).

These reactions (1), (2), and (3) are desirably carried out under an inert gas (argon, nitrogen, etc.) atmosphere in anhydrous conditions.

Furthermore, the compound represented by general formula (c) can be also produced by the reaction process scheme 3.

Reaction process scheme 3

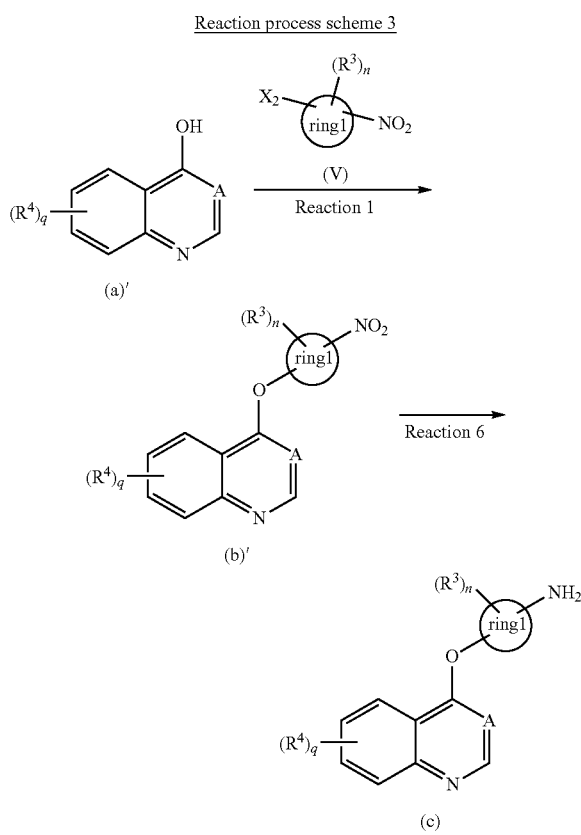

(wherein all of the symbols have the same meanings as defined above).

In the reaction process scheme 3, a compound represented by general formula (b)' can be produced by the same method as in the above-mentioned reaction 1 using a compound represented by general formula (a)' and the compound represented by general formula (V).

In the reaction process scheme 3, the reaction 6 can be carried out by subjecting the compound represented by general formula (b)' to a reduction reaction of the nitro group. The reduction reaction of a nitro group is well known, and can be carried out by, for example, the following method.

(1) The reduction reaction is carried out in, for example, a solvent [ethers (tetrahydrofuran, dioxane, dimethoxyethane, diethyl ether, etc.), alcohols (methanol, ethanol, and the like), benzenes (benzene, toluene, and the like), ketones (acetone, methyl ethyl ketone, and the like), nitriles (acetonitrile, and the like), amides (dimethylformamide, and the like), water, ethyl acetate, acetic acid or a mixture solvent of two or more thereof] in the presence of a hydrogeneration catalyst (palladium-carbon, palladium black, palladium, palladium hydroxide, platinum dioxide, platinum-carbon, nickel, Raney-nickel, ruthenium chloride, etc.), in the presence or absence of acids (hydrochloric acid, sulfuric acid, hypochlorous acid, boric acid, tetrafluoroboric acid, acetic acid, p-toluenesulfonic acid, oxalic acid, trifluoroacetic acid, formic acid, and the like), at normal pressure or reduced pressure under a hydrogen atmosphere, in the presence of formic acid ammonium or in the presence of hydrazine, at 0 to 200° C.

(2) The reaction is carried out, for example, in a water-miscible solvent (ethanol, methanol, tetrahydrofuran, etc.) in the presence or absence of an acid (hydrochloric acid, hydrobromic acid, ammonium chloride, acetic acid, ammonium formate, etc.) using a metal reagent (zinc, iron, tin, tin chloride, iron chloride, samarium, indium, sodium borohydride-Nickel chloride, etc.) at 0 to 150° C.

In the reaction process schemes 1 to 3, when a compound represented by each general formula includes a protective group, a deprotection reaction can be carried out if necessary. The deprotection reaction of the protective group is known, and can be carried out by the methods mentioned below. Examples thereof include: (1) deprotection reactions by alkaline hydrolysis, (2) deprotection reaction in acidic conditions, (3) deprotection reaction by hydrogenolysis, (4) deprotection reaction of a silyl group, (5) deprotection reaction using metal, (6) deprotection reaction using a metal complex, and the like.

These methods are specifically described:

(1) The deprotection reaction by alkaline hydrolysis condition is carried out, for example, in an organic solvent (for example, methanol, tetrahydrofuran, dioxane, etc.) with hydroxide of alkaline metal (for example, sodium hydroxide, potassium hydroxide, lithium hydroxide, etc.), hydroxide of alkaline earth metal (for example, barium hydroxide, calcium hydroxide, and the like), or carbonate (for example, sodium carbonate or potassium carbonate, and the like), or an aqueous solution thereof or a mixture thereof at 0 to 40° C.

(2) The deprotection reaction in acidic conditions is carried out, for example, in an organic solvent (for example, dichloromethane, chloroform, dioxane, ethyl acetate, methanol, isopropyl alcohol, tetrahydrofuran, anisole, etc.), organic acid (for example, acetic acid, trifluoroacetic acid, methanesulfonic acid, p-tosyl acid, etc.), or inorganic acid (for example, hydrochloric acid, sulfuric acid, etc.), or a mixture thereof (for example, hydrogen bromide/acetic acid, etc.) in the presence or absence of 2,2,2-trifluoroethanol at 0 to 100° C.

(3) The deprotection reaction by hydrogenolysis is carried out, for example, in a solvent (for example, ethers (tetrahydrofuran, dioxane, dimethoxyethane, diethyl ether, etc.), alcohols (for example, methanol, ethanol, and the like), benzenes (for example, benzene, toluene, etc.), ketones (for example, acetone, methyl ethyl ketone, and the like), nitriles (for example, acetonitrile, and the like), amides (for example, N,N-dimethylformamide, and the like), water, ethyl acetate, acetic acid, or a mixture of two or more thereof, etc.) in the presence of a catalyst (for example, palladium-carbon, palladium black, palladium hydroxide-carbon, platinum oxide, Raney nickel, etc.) under hydrogen atmosphere at normal pressure or elevated pressure, or in the presence of ammonium formate at 0 to 200° C.

(4) The deprotection reaction of a silyl group is carried out, for example, in a water-miscible organic solvent (for example, tetrahydrofuran, acetonitrile, and the like), by using tetrabutylammonium fluoride at 0 to 40° C. The reaction is also carried out, for example, in organic acid (for example, acetic acid, trifluoroacetic acid, methanesulfonic acid, p-tosyl acid, etc.), or in inorganic acid (for example, hydrochloric acid, sulfuric acid, and the like) or a mixture thereof (for example, hydrogen bromide/acetic acid, and the like) at −10 to 100° C.

(5) The deprotection reaction using a metal is carried out, for example, in an acidic solvent (for example, acetic acid, a buffer of pH 4.2 to 7.2, a mixed solution of the solution and an organic solvent such as tetrahydrofuran, etc.) in the presence of powder zinc, if necessary, with an ultrasonic wave applied at 0 to 40° C.

(6) The deprotection reaction using a metal complex is carried out, for example, in an organic solvent (for example, dichloromethane, N,N-dimethylformamide, tetrahydrofuran, ethyl acetate, acetonitrile, dioxane, ethanol, etc.), water or a mixed solvent thereof in the presence of a trap reagent (for example, tributyltin hydride, triethylsilane, dimedone, morpholine, diethylamine, pyrrolidine, etc.), an organic acid (for example, acetic acid, formic acid, 2-ethylhexanic acid, etc.) and/or in the presence of an organic acid salt (for example, sodium 2-ethylhexanate, potassium 2-ethylhexanate, and the like) in the presence or absence of a phosphine reagent (for example, triphenylphosphine, and the like) using a metal complex (for example, tetrakis (triphenylphosphine)palladium(O), dichlorobis(triphenylphosphine)palladium (II), palladium acetate (II), chlorotris (triphenylphosphine)rhodium (I), etc.) at 0 to 40° C.

In addition to the above-mentioned methods, the deprotection reaction can be carried out by the method described in for example, T. W. Greene, Protective Groups in Organic Synthesis, Wiley, New York, 1999.

Examples of a protective group for a hydroxyl group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group, and the like.

Examples of a protective group for an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluororenylmethoxycarbonyl group, a benzyl (Bn) group, a p-methoxybenzyl group, a benzyloxymethyl (BOM) group, a 2-(trimethylsilyl)ethoxymethyl (SEM) group, and the like.

The protective groups for a hydroxyl group and an amino group are not particularly limited to the above-described groups, and groups are included, in addition to the above-mentioned groups, as long as the groups can be detached easily and selectively. For example, those described in Protective Groups in Organic Synthesis (T. W. Greene, John Wiley & Sons Inc., 1999) may be used.

In each reaction in the present specification, compounds used as starting raw material, for example, the compound represented by general formula (a), (a)', (d), (II), (III), (IV) or (V) is well known or can be produced by well-known methods.

In each reaction in the present specification, as apparent to the skilled persons in the art, the reactions involving heating can be carried out using a water bath, an oil bath, a sand bath or a microwave.

In each reaction in the present specification, a solid-supported reagent which is supported on a high molecular polymer (e.g., polystyrene, polyacrylamide, polypropylene, polyethylene glycol, etc.) may be appropriately used.

In each reaction in the present specification, the reaction products can be purified by conventional purification methods, for example, by distillation at normal or reduced pressure, by high performance liquid chromatography using silica gel or magnesium silicate, thin layer chromatography, ion-exchange resin, scavenger resin, or column chromatography, washing, recrystallization, or the like. The purification may be done after each reaction or after several reactions.

[Toxicity]

The toxicity of the compound of the present invention is sufficiently low, and the compound can be safely used as pharmaceuticals.

[Application to Pharmaceuticals]

Since the compound of the present invention has an Axl inhibitory activity, it can be used as an agent for preventing and/or treating an Axl-related disease in mammals, especially in human.

In the present invention, examples of the Axl-related diseases include cancer, kidney diseases, immune system disease, and circulatory system disease.

In the present invention, the cancer includes acute myeloid leukemia, chronic myeloid leukemia, acute lymphatic leukemia, melanoma, breast cancer, pancreatic cancer, glioma, esophageal adenocarcinoma, large intestine cancer, renal cell carcinoma, thyroid cancer, non-small cell lung cancer, prostate cancer, stomach cancer, liver cancer, uveal malignant melanoma, ovarian cancer, endometrial cancer, lymphoma, head and neck cancer, and sarcoma.

In the present invention, examples of the kidney diseases include glomerular nephritis, chronic nephritis, IgA nephritis, sequential (secondary) nephritis, nephrosis nephritis, acute renal failure, chronic renal failure, diabetic nephropathy, gouty nephropathy, interstitial nephritis, and nephropyelitis.

In the present invention, examples of the immune system disease include psoriasis, and rheumatoid arthritis.

In the present invention, examples of the circulatory system disease include atherosclerosis and thrombosis.

Furthermore, since the compound of the present invention has an Axl inhibitory activity, it can be used as a metastasis suppressing agent to cancer cell.

The compound of the present invention may be administered as a combination drug in combination with other drugs in order to accomplish the following purposes:
1) to supplement and/or enhance the preventive and/or therapeutic effect of the compound;
2) to improve the kinetics, improvement of absorption, and reduction of the dose of the compound; and/or
3) to eliminate the side effects of the compound.

A combination drug of the compound of the present invention and other drugs may be administered in the form of a compounding agent including these components mixed into one formulation, or may be administered in separate formulations. Administration as separate formulations includes simultaneous administration and administration at different times. In the administration at different times, the compound of the present invention may be administered before the other drug. Alternatively, the other drug may be administered before the compound of the present invention. The method for the administration of these drugs may be the same as each other or different from each other.

Diseases on which the preventive and/or therapeutic effect of the above-mentioned combination drug works are not particularly limited but may be those in which the preventive and/or therapeutic effect of the compound of the present invention is supplemented and/or enhanced.

The other drugs for supplementing and/or enhancing the preventive and/or therapeutic effect of the compound of the present invention against cancer include, for example, alkylating agents, antimetabolites, anticancer antibiotics, plant alkaloids, hormones, platinum compounds, anti-CD20 antibodies, anti-CD52 antibodies, anti-PD-1 antibodies, G-CSF formulations, acute promyelocytic leukemia differentiation-inducing agents, kinase inhibitors, topoisomerase inhibitors, aromatase inhibitors, and other anticancer drugs.

The other drug for supplementing and/or enhancing the preventive and/or therapeutic effect of the compound of the present invention against kidney diseases include, for example, steroids, immunosuppressants, angiotensin II antagonistic drugs, angiotensin-converting enzyme inhibitors, antiplatelet drugs, and anticoagulant drugs.

The other drugs for supplementing and/or enhancing the preventive and/or therapeutic effect of the compound of the present invention against immune system diseases include, for example, immunosuppressants, steroid, disease-modifying anti-rheumatic drugs, prostaglandins, prostaglandin synthase inhibitors, phosphodiesterase inhibitors, metalloprotease inhibitors, anti-cytokine protein formulations such as anti-TNF-α formulations, anti-IL-1 formulations, and anti-IL-6 formulation, cytokine inhibitors, and nonsteroidal anti-inflammatory agents.

The other drugs for supplementing and/or enhancing the preventive and/or therapeutic effect of the compound of the present invention against circulatory system diseases include antiplatelet drugs, angiotensin II antagonistic drugs, angiotensin-converting enzyme inhibitors, HMG-CoA reductase inhibitors, and thiazolidine derivatives.

Examples of the alkylating agents include nitrogen mustard N-oxide hydrochloride, cyclophosphamide, ifosfamide, melphalan, thiotepa, carboquone, busulfan, nimustine hydrochloride, dacarbazine, ranimustine, carmustine, chlorambucil, bendamustine, and mechlorethamine.

Examples of the antimetabolites include methotrexate, mercaptopurine, 6-mercaptopurine riboside, fluorouracil, tegafur, tegafur uracil, carmofur, doxifluridine, cytarabine, enocitabine, tegafur gimestat otastat potassium, gemcitabine hydrochloride, cytarabine ocfosfate, procarbazine hydrochloride, and hydroxycarbamide.

Examples of the anticancer antibiotics include actinomycin D, mitomycin C, daunorubicin hydrochloride, doxorubicin hydrochloride, aclarubicin hydrochloride, neocarzinostatin, pirarubicin hydrochloride, epirubicin (hydrochloride), idarubicin hydrochloride, chromomycin A3, bleomycin (hydrochloride), peplomycin sulfate, therarubicin, zinostatin stimalamer, gemtuzumab ozogamicin, and the like.

Examples of the plant formulations include vinblastine sulfate, vincristine sulfate, vindesine sulfate, irinotecan hydrochloride, etoposide, flutamide, vinorelbine tartrate, docetaxel hydrate, paclitaxel, and the like.

Examples of the hormones include estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, aminoglutethimide, androgen bicalutamide, fulvestrant, and the like.

Examples of the platinum compounds include carboplatin, cisplatin, nedaplatin, and oxaliplatin, and the like.

Examples of the anti-CD20 antibodies include rituximab, ibritumomab, ibritumomab tiuxetan, and ocrelizumab.

Examples of the anti-CD52 antibodies include alemtuzumab.

Examples of the anti-PD-1 antibodies include nivolumab, and pembrolizumab.

Examples of the G-CSF formulation include pegfilgrastim, filgrastim, lenograstim, and nartograstim.

Examples of the differentiation-inducing agent for acute promyelocytic leukemia include tamibarotene, tretinoin, and arsenic trioxide formulations.

Examples of the kinase inhibitors include EGFR inhibitors including erlotinib hydrochloride, gefitinib, cetuximab, and panitumumab; HER$^2$ inhibitors including lapatinib and trastuzumab; BCR-ABL inhibitors including imatinib, dasatinib, and nilotinib; multikinase inhibitors including sunitinib, vandetanib, crizotinib, and sorafenib.

Examples of the topoisomerase inhibitor include topotecan, teniposide, irinotecan, and sobuzoxane.

Examples of the aromatase inhibitor include exemestane.

Examples of the other anticancer agents include L-asparaginase, octreotide acetate, porfimer sodium, mitoxantrone acetate, aceglatone, ubenimex, eribulin mesilate, cladribine, krestin, bexarotene, denileukin diftitox, temozolomide, nelarabine, fludarabine, bevacizumab, pemetrexed, pentostatin, bortezomib, lenalidomide, and calcium folinate.

Examples of the immunosuppressant include azathioprine, ascomycin, everolimus, salazosulfapyridine, cyclosporine, cyclophosphamide, sirolimus, tacrolimus, bucillamine, methotrexate, and leflunomide.

Examples of the steroid include amcinonide, hydrocortisone sodium succinate, prednisolone sodium succinate, methylprednisolone sodium succinate, ciclesonide, diflupredonate, betamethasone propionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfate, mometasone furoate, fluocinonide, fluocinolone acetonide, fludroxycortide, flunisolide, prednisolone, alclometasone propionate, clobetasol propionate, dexamethasone propionate, deprodone propionate, fluticasone propionate, beclometasone propionate, betamethasone, methylprednisolone, methylprednisolone suleptanate, methylprednisolone sodium succinate, dexamethasone sodium phosphate, hydrocortisone sodium phosphate, prednisolone sodium phosphate, diflucortolone valerate, dexamethasone valerate, betamethasone valerate, prednisolone valerate acetate, cortisone acetate, diflorasone acetate, dexamethasone acetate, triamcinolone acetate, paramethason acetate, halopredone acetate, fludrocortisone acetate, prednisolone acetate, methylprednisolone acetate, clobetasone butyrate, hydrocortisone butyrate, hydrocortisone butyrate propionate, and betamethasone butyrate propionate.

Examples of the angiotensin II antagonistic drug include losartan, candesartan, valsartan, irbesartan, olmesartan, telmisartan, and the like.

Examples of the angiotensin-converting enzyme inhibitor include alacepril, imidapril hydrochloride, quinapril hydrochloride, temocapril hydrochloride, delapril hydrochloride, benazepril hydrochloride, captopril, trandolapril, perindopril erbumine, enalapril maleate, lisinopril, and the like.

Examples of the antiplatelet drugs include dipyridamole, and dilazep hydrochloride hydrate.

Examples of the anticoagulant drugs include warfarin and heparin.

Examples of the disease-modifying anti-rheumatic drugs include D-penicillamine, actarit, auranofin, salazosulfapyridine, hydroxychloroquine, bucillamine, methotrexate, leflunomide, lobenzarit sodium, aurothioglucose, and sodium aurothiomalate.

Examples of the prostaglandins (hereinafter, abbreviated as "PG") include PGE1 formulations (examples: alprostadil alfadex, alprostadil, and the like), PGI2 formulations (example: beraprost sodium, and the like), PG receptor agonists, and PG receptor antagonists. Examples of the PG receptor include PGE receptors (EP1, EP2, EP3, and EP4), PGD receptors (DP, and CRTH2), PGF receptors (FP), PGI2 receptors (IP), and TX receptors (TP).

Examples of the prostaglandin synthase inhibitor include salazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, naproxen, piroxicam, piroxicam cinnamate, zaltoprofen, and pranoprofen.

Examples of the phosphodiesterase inhibitor include rolipram, cilomilast, Bay19-8004, NIK-616, roflumilast (BY-217), cipamfylline (BRL-61063), atizoram (CP-80633), ONO-6126, SCH-351591, YM-976, V-11294A, PD-168787, D-4396, and IC-485.

Examples of the anti-TNF-α formulation include anti-TNF-α antibodies, soluble TNF-α receptor, anti-TNF-α receptor antibodies, and soluble TNF-α binding protein, and particularly infliximab and etanercept.

Examples of the anti-IL-1 formulation include anti-IL-1 antibodies, soluble IL-1 receptor, anti-IL-1Ra antibodies and/or anti-IL-1 receptor antibodies and particularly anakinra.

Examples of the anti-IL-6 formulation include anti-IL-1 antibodies, soluble IL-6 receptor, and anti-IL-6 receptor antibodies, and particularly tocilizumab.

Examples of the cytokine inhibitor include suplatast tosylate, T-614, SR-31747, and sonatimod.

Examples of the HMG-CoA reductase inhibitor include atorvastatin, fluvastatin, lovastatin, pitavastatin, pravastatin, rosuvastatin, and simvastatin.

Examples of the thiazolidine derivative include pioglitazone, ciglitazone, rosiglitazone, and troglitazone.

Furthermore, the combination drugs to be combined with a compound of the present invention includes not only ones discovered to date, but also ones that may be discovered in the future.

The compound of the present invention is usually administered systemically or locally, by oral or parenteral administration. Examples of oral agents include liquid medicines for internal use (for example, elixirs, syrups, pharmaceutically acceptable water-based agents, suspensions, and emulsions), and solid medicine for internal use (for example, tablets (including sublingual tablets and orally disintegrating tablets), pills, capsules (including hard capsules, soft capsules, gelatin capsules, and microcapsules), powders, granules, and lozenges). Examples of parenteral agents include liquid medicines (for example, injection agents (subcutaneous injection agents, intravenous injection agents, intramuscular injection agents, intraperitoneal injection agents, and drip agents, and the like), eye drops (for example, aqueous eye drops (aqueous eye drops, aqueous eye drop suspensions, viscous eye drops, and solubilized eye drops, etc.), and nonaqueous eye drops (for example, nonaqueous eye drops and nonaqueous eye drop suspensions), and the like), agents for external use (for example, ointments (ophthalmic ointments, and the like)), and ear drops, and the like. These formulations may be controlled release agents such as rapid release formulations, sustained release formulations, and the like. These formulations can be produced by well-known methods, for example, by the methods described in The Japanese Pharmacopoeia.

Liquid medicines for internal use as the oral agent can be produced by, for example, dissolving or suspending an active ingredient in a generally used diluent (for example, purified water, ethanol, or mixture liquid thereof, or the like). The liquid medicine may include a wetting agent, a suspension agent, a sweetening agent, a flavoring material, an aromatic substance, a preservative, a buffer agent, and the like.

Solid medicines for internal use as the oral agent are formulated by, for example, mixing the active ingredient with, for example, a vehicle (for example, lactose, mannitol, glucose, microcrystalline cellulose, starch, and the like), a binder (for example, hydroxypropyl cellulose, polyvinylpyrrolidone, magnesium metasilicate aluminate, and the like), a disintegrant (for example, sodium carboxymethylcellulose, and the like), a lubricant (for example, magnesium stearate, and the like), a stabilizer, a dissolution adjuvant (for example, glutamic acid, aspartic acid, and the like), and the like, and formulating according to standard methods. As necessary, coating may be carried out with a coating agent (for example, sugar, gelatin, hydroxypropyl cellulose, hydroxypropyl methyl cellulose phthalate, and the like), and coating of two or more layers may be employed.

Agents for external use as parenteral agents are produced by well-known methods or generally used prescriptions. For example, an ointment may be produced by incorporation or melting of an active ingredient into base material. The ointment base material is selected from well-known material or generally used material. For example, a single material or a mixture of two or more of materials are selected from higher fatty acids and higher fatty acid esters (for example, adipic acid, myristic acid, palmitic acid, stearic acid, oleic acid, adipate esters, myristate esters, palmitate esters, stearate esters, oleate esters, and the like), waxes (for example, beeswax, spermaceti, ceresin, and the like), surfactants (for example, polyoxyethylene alkyl ether phosphate esters, and the like), higher alcohols (for example, cetanol, stearyl alcohol, etostearyl alcohol, and the like), silicone oils (for example, dimethylpolysiloxane, and the like), hydrocarbons (for example, hydrophilic petrolatum, white petrolatum, purified lanolin, liquid paraffin, and the like), glycols (for example, ethylene glycol, diethylene glycol, propylene glycol, polyethylene glycol, macrogol, and the like), plant oils (for example, castor oil, olive oil, sesame oil, turpentine oil, and the like), animal oils (for example, mink oil, egg yolk oil, squalane, squalene, and the like), water, absorption promoters, and anti-irritants. Furthermore, a humectant, preservative, stabilizer, antioxidant, fragrance, and the like, may be included.

The injection agents as parenteral agents include solutions, suspensions, emulsions and solid injection agents to be dissolved or suspended in a solvent before use. The injection agent is used by, for example, dissolving, suspending or emulsifying an active ingredient in a solvent. Examples of the solvent include distilled water for injection, physiological saline, vegetable oils, alcohols such as propylene glycol, polyethylene glycol, ethanol, and mixtures thereof. Furthermore, the injection agent may contain a stabilizer, a dissolution aid (glutamic acid, aspartic acid, and Polysorbate 80 (registered trademark), etc.), a suspending agent, an emulsifying agent, a soothing agent, a buffer, a preservative, and the like. Such an injection agent is produced by sterilizing at the final step or employing an aseptic process. Furthermore, it is also possible to employ an aseptic solid product such as a freeze-dried product produced and sterilized or dissolved in aseptic distilled water for injection or other solvent before use.

When the compound of the present invention or combination agents of the compound of the present invention and other agents are used for the above-mentioned purposes, they are usually administered systemically or locally, usually by oral or parenteral administration. The doses to be administered are different depending upon ages, body weights, symptoms, therapeutic effects, administration method, treatment time, and the like. The doses per adult person are generally from 1 ng to 1000 mg per dose, once or several times per day, by oral administration, from 0.1 ng to 100 mg per dose, once or several times per day, by parenteral administration, or continuous administration 1 to 24 hours per day intravenously. Needless to say, as mentioned above, the doses to be used vary dependent upon various conditions. Therefore, doses lower than the ranges specified above may be sufficient in some cases, and doses higher than the ranges specified above are needed in some cases.

EXAMPLES

Hereinafter, the present invention is described in detail with reference to Examples mentioned below, but the present invention is not limited thereto.

Solvents given in parentheses shown in chromatographic separation and TLC each indicate the eluting solvent or the developing solvent used, and the ratio is expressed in ratio by volume. The description "NH silica" denotes that CHROMATOREX NH TLC PLATE (catalog No.; 3800003) manufactured by FUJI SILYSIA CHEMICAL LTD. is used; and "DNH silica" denotes that CHROMATOREX NH TLC PLATE (catalog No.; 3800403) manufactured by FUJI SILYSIA CHEMICAL LTD. is used;

LC-MS/ELSD was carried out in the following conditions:
{Column: Waters ACQUITY $C_{18}$ (particle diameter: 1.7×$10^{-6}$; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (rate of mobile phase (A): mobile phase (B)): [0 min] 95:5; [0.1 min] 95:5; [1.2 min] 5:95; [1.4 min] 5:95; [1.41 min] 95:5; [1.5 min] 95:5; detector: UV (PDA), ELSD, MS}

The description in a parenthesis in the NMR data shows a solvent used for measurement.

Name of the compounds used in this specification are named by using ACD/Name (registered trademark) manufactured by Advanced Chemistry Development Inc., which is a computer program for naming compounds according to the regulation of IUPAC, or named according to the naming method of IUPAC.

Example 1

4-[(6-chloro-3-pyridinyl)oxy]-6,7-dimethoxy quinoline

Under the stream of nitrogen, a solution of 4-chloro-6,7-dimethoxy quinoline (1.00 g) (CAS registration No.: 35654-56-9) in chlorobenzene (9 mL), 6-chloropyridine-3-ol (0.65 g), and triethyl amine (11.3 mL) were placed in a 100-mL four-necked flask, and the mixture was stirred at a bath temperature (140° C.) for five days. The resulting solution was left to cool to room temperature, water and ethyl acetate were added thereto, and the solution was separated. The water layer was extracted again with ethyl acetate, and the combined organic layer was washed with a saturated saline solution, and dried over anhydrous sodium sulfate. The solvent was distilled off under reduced pressure. The resulting residue was purified by silica gel column chromatography (hexane:ethyl acetate=1:8) to obtain the title compound (1.16 g) having the following physical property values.

TLC: Rf 0.22 (hexane:ethyl acetate=1:3);
$^1$H-NMR (DMSO-$d_6$) δ 8.52, 8.48, 7.87-7.85, 7.66, 7.49, 7.43, 6.65, 3.95, 3.93.

Example 2

5-[(6,7-dimethoxy-4-quinolinyl)oxy]-2-pyridinamine

Under the stream of nitrogen, a solution of the compound (1.15 g) produced in Example 1 in tetrahydrofuran (THF) (18 mL), 1.0 mol/L lithium bis(trimethylsilyl)amide (LHDMS) (5.45 mL), tris(dibenzylideneacetone)dipalladium(0) chloroform complex (0.19 g), and 2-dicyclohexylphosphino-2',6'-dimethoxybiphenyl (0.15 g) were placed in a 200-mL four-necked flask, and the mixture was stirred at a bath temperature (80° C.) for 16.5 hours. Furthermore, 6 mol/L hydrochloric acid (10 mL) was added thereto, and the mixture was stirred at a bath temperature (80° C.) for two hours. The mixture was left to cool to room temperature, then a sodium hydrogen bicarbonate aqueous solution and ethyl acetate were added, and the resulting solution was separated. The water layer was extracted again with ethyl acetate, and the combined organic layer was washed with a saturated saline solution, and then dried over anhydrous sodium sulfate. The solvent was distilled off under reduced pressure. The resulting residue was purified by silica gel column chromatography (ethyl acetate→ethyl acetate:methanol=9:1) to obtain the title compound (0.80 g) having the following physical property values.

TLC: Rf 0.51 (ethyl acetate:methanol=4:1);
$^1$H-NMR (DMSO-$d_6$): δ 8.45, 7.89, 7.51, 7.38-7.36, 6.56, 6.42, 6.05, 3.94.

Example 3 ethyl 2,5-dioxo-5,6,7,8-tetrahydro-2H-chromene-3-carboxylate 1,3-cyclohexanedione (CAS registration No.: 504-02-9) (13.25 g) was dissolved in N,N-dimethyl formamide (DMF) (200 mL) at room temperature, and tert-butoxy potassium (13.26 g) and ethyl (E)-2-cyano-3-ethoxy-2-propenoate (CAS registration No.: 94-05-3) (20.00 g) were added thereto. The mixture was stirred for 21 hours. The reaction solution was diluted with ethyl acetate, 2 mol/L hydrochloric acid aqueous solution was added thereto, and the mixture was stirred. Ethyl acetate and water were further added, and the organic layer was extracted. The extract was washed with a saturated saline solution, then dried over anhydrous sodium sulfate, and the solvent was distilled off under reduced pressure to obtain the title compound (23.62 g) having the following physical property values.

TLC: Rf 0.35 (hexane:ethyl acetate=1:1);
$^1$H-NMR (CDCl$_3$): δ 1.37, 2.19, 2.61, 2.92, 4.36, 8.63.

Example 4

2,5-dioxo-1-phenyl-1,2,5,6,7,8-hexahydro-3-quinoline carboxylic acid

The compound (10.00 g) produced in Example 3 was dissolved in ethanol (200 mL) at room temperature, aniline (3.94 g) was added thereto, and the mixture was stirred for six hours. Solids precipitated from the reaction solution were collected by filtration through Kiriyama funnel, and washed with ethanol. The obtained residue was dried under reduced pressure at 60° C. The title compound (4.01 g) having the following physical property values was obtained.

TLC: Rf 0.37 (dichloromethane:methanol=9:1);
$^1$H-NMR (CDCl$_3$): δ 2.11, 2.60, 7.25, 7.63, 9.21.

Example 5

N-{5-[(6,7-dimethoxy-4-quinolinyl)oxy]-2-pyridinyl}-2,5-dioxo-1-phenyl-1,2,5,6,7,8-hexahydro-3-quinolinecarboxamide

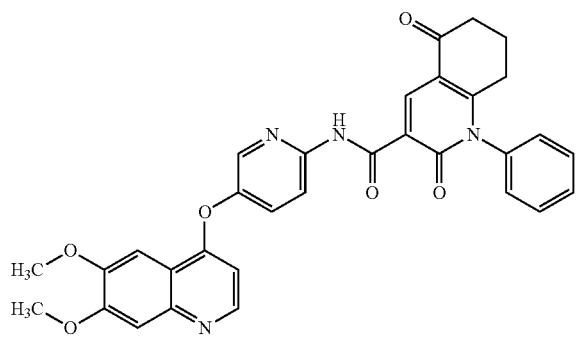

The compound (105 mg) produced in Example 4 and O-(7-aza-1-benzotriazolyl)-N,N,N',N'-tetramethyl uronium hexafluorophosphate (HATU) (192 mg) were dissolved in DMF (2 mL) at room temperature, diisopropylethylamine (DIPEA) (0.17 mL) and the compound (100 mg) produced in Example 2 were added thereto, and the mixture was stirred for 21 hours. The solvent was distilled off under reduced pressure. The resulting residue was purified by silica gel chromatography (hexane:ethyl acetate=30:70→0:100→ethyl acetate:methanol=70:30) to obtain the title compound (116 mg) having the following physical property values.

TLC: Rf 0.76 (ethyl acetate:methanol=5:1);
$^1$H-NMR (CDCl$_3$): δ 2.13, 2.60, 4.05, 6.44, 7.25, 7.42, 7.53, 7.63, 8.22, 8.48, 8.51, 9.32, 11.93.

Examples 5(1) to 5(54)

The following Example compounds were obtained by the procedure having the same purpose as in Example 5 using the compound produced in Example 2 and corresponding carboxylic acid derivatives in place of the compound produced in Example 4.

Example 5(1)

N-{5-[(6,7-dimethoxy-4-quinolinyl)oxy]-2-pyridinyl}-7,7-dimethyl-2,5-dioxo-1-phenyl-1,2,5,6,7,8-hexahydro-3-quinolinecarboxamide

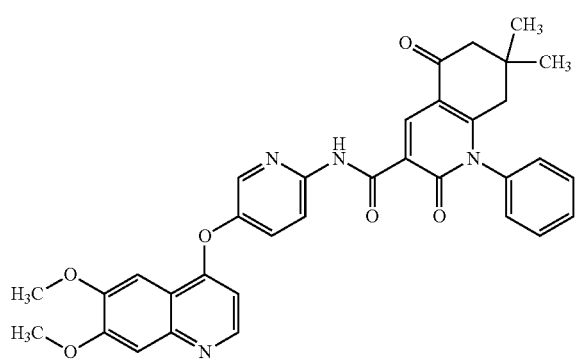 [SMILES: COc1cc2nccc(Oc3ccc(NC(=O)c4cc5c(n(-c6ccccc6)c4=O)CC(C)(C)CC5=O)nc3)c2cc1OC]

TLC: Rf 0.75 (ethyl acetate:methanol=5:1);
$^1$H-NMR (CDCl$_3$): δ 1.06, 2.43, 2.48, 4.05, 6.45, 7.25, 7.43, 7.54, 7.55-7.65, 8.22, 8.48, 8.51, 9.32, 11.92.

Example 5(2)

N-{5-[(6,7-dimethoxy-4-quinolinyl)oxy]-2-pyridinyl}-2',5'-dioxo-1'-phenyl-2',5',6',8'-tetrahydro-1'H-spiro[cyclopropane-1,7'-quinoline]-3'-carboxamide TLC: Rf 0.69 (ethyl acetate:methanol=5:1);
$^1$H-NMR (CDCl$_3$): δ 0.39, 0.54, 2.41, 2.48, 4.05, 6.45, 7.22, 7.43, 7.53, 7.55-7.62, 8.22, 8.49, 8.51, 9.36, 11.92.
(Byproduct)

N-{5-[(6,7-dimethoxy-4-quinolinyl)oxy]-2-pyridinyl}-8'-hydroxy-2',5'-dioxo-1'-phenyl-2',5',6',8'-tetrahydro-1'H-spiro[cyclopropane-1,7'-quinoline]-3'-carboxamide TLC: Rf 0.68 (ethyl acetate:methanol=5:1);
$^1$H-NMR (CDCl$_3$): δ 0.44, 0.61, 1.89, 3.39, 3.45, 4.10, 4.14, 6.76, 7.19, 7.47, 7.58-7.65, 7.86, 8.25, 8.63, 9.27, 12.05.

Example 5(3)

N-{5-[(6,7-dimethoxy-4-quinolinyl)oxy]-2-pyridinyl}-1-ethyl-2,5-dioxo-1,2,5,6,7,8-hexahydro-3-quinolinecarboxamide (LC-MS/ELSD): (retention time: 0.70 min);
$^1$H-NMR (CDCl$_3$): δ 1.41-1.46, 2.25-2.29, 2.62-2.65, 3.07-3.11, 4.06, 4.26-4.30, 6.45-6.47, 7.43, 7.55, 7.55-7.60, 8.29-8.31, 8.50-8.53, 9.21, 12.23.

Example 5(4)

N-{5-[(6,7-dimethoxy-4-quinolinyl)oxy]-2-pyridinyl}-1-(4-fluorobenzyl)-2,5-dioxo-1,2,5,6,7,8-hexahydro-3-quinolinecarboxamide (LC-MS/ELSD): (retention time: 0.80 min);
$^1$H-NMR (CDCl$_3$): δ 2.14-2.20, 2.58-2.63, 2.96-3.01, 4.06, 5.50, 6.45-6.47, 6.89-7.10, 7.26-7.37, 7.43, 7.55, 7.57-7.61, 8.29-8.30, 8.50-8.54, 9.29, 12.10.

Example 5(5)

N-{5-[(6,7-dimethoxy-4-quinolinyl)oxy]-2-pyridinyl}-2,5-dioxo-1-(tetrahydro-2H-pyran-4-yl)-1,2,5,6,7,8-hexahydro-3-quinolinecarboxamide (LC-MS/ELSD): (retention time: 0.67 min);
$^1$H-NMR (CDCl$_3$): δ 2.20-2.30, 2.60-2.64, 3.00-3.30, 3.45-3.55, 4.06, 4.15-4.20, 4.40-4.60, 6.45-6.47, 7.44, 7.55-7.61, 8.30-8.31, 8.49-8.52, 9.20, 12.17.

Example 5(6)

N-{5-[(6,7-dimethoxy-4-quinolinyl)oxy]-2-pyridinyl}-1-(2,2-dimethylpropyl)-2,5-dioxo-1,2,5,6,7,8-hexahydro-3-quinolinecarboxamide

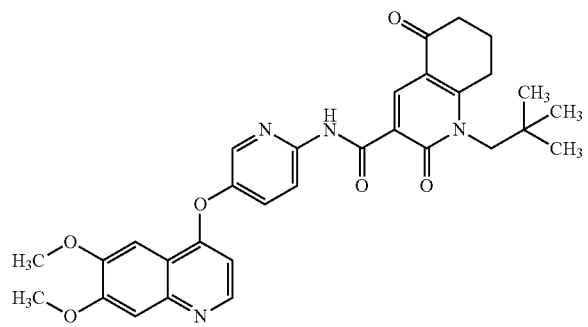 [SMILES: COc1cc2nccc(Oc3ccc(NC(=O)c4cc5c(n(CC(C)(C)C)c4=O)CCCC5=O)nc3)c2cc1OC]

TLC: Rf 0.54 (ethyl acetate:methanol=9:1);
$^1$H-NMR (CDCl$_3$): δ 0.99, 2.09, 2.56, 3.19, 3.94, 4.25, 6.54, 7.40, 7.53, 7.86, 8.39, 8.48, 8.89, 12.19.

Example 5(7)

N-{5-[(6,7-dimethoxy-4-quinolinyl)oxy]-2-pyridinyl}-1-(4-fluorophenyl)-2,5-dioxo-1,2,5,6,7,8-hexahydro-3-quinolinecarboxamide

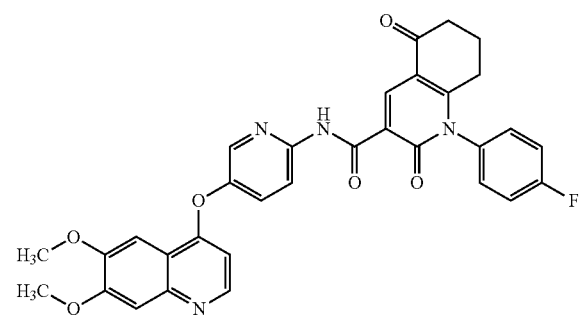 [SMILES: COc1cc2nccc(Oc3ccc(NC(=O)c4cc5c(n(-c6ccc(F)cc6)c4=O)CCCC5=O)nc3)c2cc1OC]

TLC: Rf 0.59 (dichloromethane:methanol=9:1);
$^1$H-NMR (CDCl$_3$): δ 2.13, 2.60, 4.05, 6.44, 7.24-7.35, 7.43, 7.54, 7.57, 8.23, 8.50, 9.32, 11.88.

Example 5(8)

N-{5-[(6,7-dimethoxy-4-quinolinyl)oxy]-2-pyridinyl}-6,6-dimethyl-2,5-dioxo-1-phenyl-1,2,5,6,7,8-hexahydro-3-quinolinecarboxamide

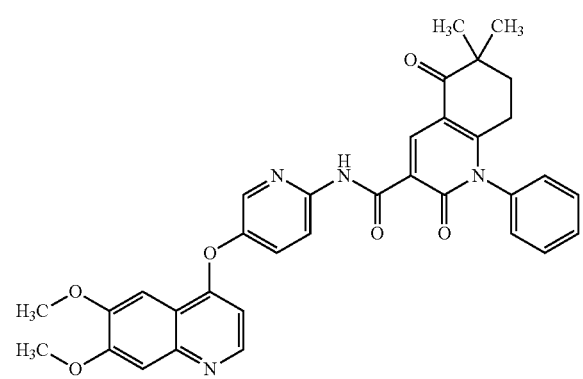 [SMILES: COc1cc2nccc(Oc3ccc(NC(=O)c4cc5c(n(-c6ccccc6)c4=O)CCC(C)(C)C5=O)nc3)c2cc1OC]

TLC: Rf 0.51 (dichloromethane:methanol=10:1);
$^1$H-NMR (CDCl$_3$): δ 1.13, 1.80-1.90, 2.40-2.60, 3.92, 3.94, 6.53-6.55, 7.40, 7.50-7.53, 7.57-7.66, 7.84-7.88, 8.34-8.36, 8.40-8.43, 8.47-8.49, 8.99, 11.98.

Example 5(9)

N-{5-[(6,7-dimethoxy-4-quinolinyl)oxy]-2-pyridinyl}-1-isobutyl-2,5-dioxo-1,2,5,6,7,8-hexahydro-3-quinolinecarboxamide TLC: Rf 0.50 (ethyl acetate:methanol=19:1);
$^1$H-NMR (DMSO-d$_6$): δ 0.94, 2.05-2.25, 2.49-2.65, 3.15-3.24, 3.93, 4.13, 6.54, 7.04, 7.53, 7.86, 8.38-8.45, 8.48, 8.89, 12.24.

Example 5(10)

N-{5-[(6,7-dimethoxy-4-quinolinyl)oxy]-2-pyridinyl}-1-[(2R)-1-hydroxy-3-methyl-2-butanyl]-2,5-dioxo-1,2,5,6,7,8-hexahydro-3-quinolinecarboxamide TLC: Rf 0.20 (ethyl acetate, NH silica);
$^1$H-NMR (CDCl$_3$): δ 0.70, 1.11, 2.13, 2.41, 2.87-2.99, 3.35, 4.02, 4.07, 4.19, 4.88, 6.17, 7.19, 7.53, 7.86, 8.17, 8.37, 8.58, 8.61, 12.18.

Example 5(11)

N-{5-[(6,7-dimethoxy-4-quinolinyl)oxy]-2-pyridinyl}-1-[(2S)-1-hydroxy-3-methyl-2-butanyl]-2,5-dioxo-1,2,5,6,7,8-hexahydro-3-quinolinecarboxamide

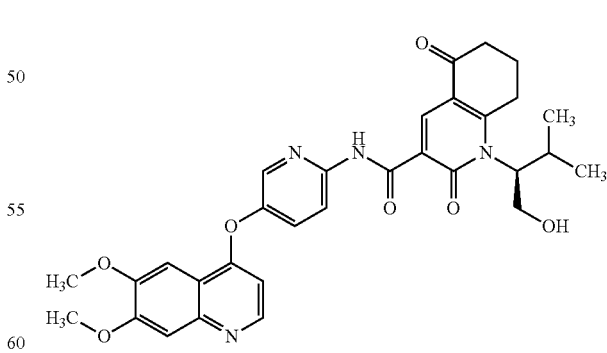

TLC: Rf 0.20 (ethyl acetate, NH silica);
$^1$H-NMR (CDCl$_3$): δ 0.70, 1.11, 2.13, 2.41, 2.87-2.99, 3.35, 4.02, 4.07, 4.19, 4.88, 6.17, 7.19, 7.53, 7.86, 8.17, 8.37, 8.58, 8.61, 12.18.

Example 5(12)

N-{5-[(6,7-dimethoxy-4-quinolinyl)oxy]-2-pyridinyl}-1-(3-fluorophenyl)-2,5-dioxo-1,2,5,6,7,8-hexahydro-3-quinolinecarboxamide

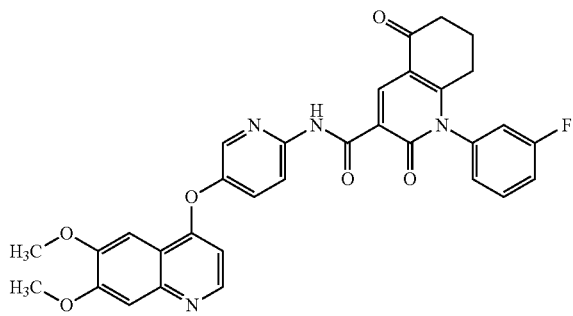 [SMILES: COc1cc2nccc(Oc3ccc(NC(=O)c4cc5c(n(-c6cccc(F)c6)c4=O)CCCC5=O)nc3)c2cc1OC]

TLC: Rf 0.56 (ethyl acetate:methanol=9:1);

$^1$H-NMR (CDCl$_3$): δ 2.13, 2.60, 4.05, 6.44, 7.07, 7.32, 7.43, 7.54, 7.59, 8.23, 8.49, 9.32, 11.85.

Example 5(13)

N-{5-[(6,7-dimethoxy-4-quinolinyl)oxy]-2-pyridinyl}-1-[1-(hydroxymethyl)cyclobutyl]-2,5-dioxo-1,2,5,6,7,8-hexahydro-3-quinolinecarboxamide TLC: Rf 0.15 (ethyl acetate, NH silica);

$^1$H-NMR (CDCl$_3$): δ 1.81-1.95, 2.16-2.29, 2.40-2.75, 2.83-3.01, 3.45, 4.05, 4.06, 4.18, 4.48, 6.41, 7.39, 7.55, 7.61, 8.28, 8.46, 8.54, 9.08, 11.99.

Example 5(14)

N-{5-[(6,7-dimethoxy-4-quinolinyl)oxy]-2-pyridinyl}-1-[(1R)-1-(4-fluorophenyl)ethyl]-2,5-dioxo-1,2,5,6,7,8-hexahydro-3-quinolinecarboxamide TLC: Rf 0.51 (ethyl acetate);

$^1$H-NMR (CDCl$_3$): δ 2.00-2.20, 2.45-3.07, 4.05, 4.06, 6.45, 7.03-7.12, 7.18-7.23, 7.43, 7.55, 7.58, 8.28, 8.50, 8.51, 9.23, 12.07.

Example 5(15)

N-{5-[(6,7-dimethoxy-4-quinolinyl)oxy]-2-pyridinyl}-1-[(1S)-1-(4-fluorophenyl)ethyl]-2,5-dioxo-1,2,5,6,7,8-hexahydro-3-quinolinecarboxamide TLC: Rf 0.50 (ethyl acetate, NH silica);

$^1$H-NMR (CDCl$_3$): δ 2.00-2.20, 2.45-3.07, 4.05, 4.06, 6.45, 7.03-7.12, 7.18-7.23, 7.43, 7.55, 7.58, 8.28, 8.50, 8.51, 9.23, 12.07.

Example 5(16)

N-{5-[(6,7-dimethoxy-4-quinolinyl)oxy]-2-pyridinyl}-1-(2-fluorophenyl)-2,5-dioxo-1,2,5,6,7,8-hexahydro-3-quinolinecarboxamide

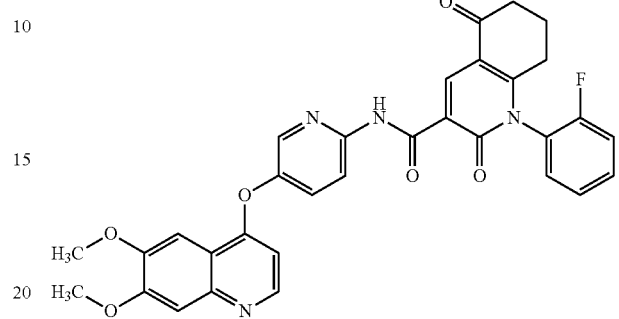

TLC: Rf 0.52 (ethyl acetate:methanol=9:1);

$^1$H-NMR (CDCl$_3$): δ 2.15, 2.63, 4.05, 6.44, 7.26-7.61, 8.22, 8.49, 9.33, 11.85.

Example 5(17)

N-{5-[(6,7-dimethoxy-4-quinolinyl)oxy]-2-pyridinyl}-2',5'-dioxo-1'-phenyl-2',5',6',8'-tetrahydro-1'H-spiro[cyclobutane-1,7'-quinoline]-3'-carboxamide TLC: Rf 0.71 (ethyl acetate:methanol=5:1);

$^1$H-NMR (CDCl$_3$): δ 1.78-1.93, 2.64, 2.73, 2.93, 3.02, 4.05, 6.45, 7.24, 7.42, 7.53-7.67, 8.22, 8.49, 9.29, 11.92.

Example 5(18)

N-{5-[(6,7-dimethoxy-4-quinolinyl)oxy]-2-pyridinyl}-2,5-dioxo-1-[(1S)-1-phenylethyl]-1,2,5,6,7,8-hexahydro-3-quinolinecarboxamide TLC: Rf 0.69 (ethyl acetate:methanol=5:1);

$^1$H-NMR (CDCl$_3$): δ 2.01, 2.55, 2.95, 4.05, 4.06, 6.44, 7.19, 7.29-7.43, 7.55, 7.57, 8.28, 8.49-8.53, 9.25, 12.13.

Example 5(19)

1-cyclopropyl-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.69 min);

MASS (ESI, Pos.): 527 (M+H)$^+$.

Example 5(20)

1-(1-cyclopropyl-2-hydroxyethyl)-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.71 min);

MASS (ESI, Pos.): 571 (M+H)$^+$.

Example 5(21)

N-{5-[(6,7-dimethoxy-4-quinolinyl)oxy]-2-pyridinyl}-1-[2-(methylsulfonyl)-1-phenylethyl]-2,5-dioxo-1,2,5,6,7,8-hexahydro-3-quinolinecarboxamide TLC: Rf 0.67 (ethyl acetate:methanol=5:1);
$^1$H-NMR (CDCl$_3$): δ 2.20-2.80, 3.14, 3.92, 3.93, 4.61, 6.29, 6.49, 7.33, 7.39, 7.50, 7.83, 8.34, 8.45, 8.92, 11.80.

Example 5(22)

N-{5-[(6,7-dimethoxy-4-quinolinyl)oxy]-2-pyridinyl}-2,5-dioxo-1-(3-pentanyl)-1,2,5,6,7,8-hexahydro-3-quinolinecarboxamide (LC-MS/ELSD): (retention time: 0.80 min);
MASS (ESI, Pos.): 557 (M+H)$^+$.

Example 5(23)

N-{5-[(6,7-dimethoxy-4-quinolinyl)oxy]-2-pyridinyl}-1-(2-hydroxy-2-methylpropyl)-2,5-dioxo-1,2,5,6,7,8-hexahydro-3-quinolinecarboxamide (LC-MS/ELSD): (retention time: 0.66 min);
MASS (ESI, Pos.): 559 (M+H)$^+$.

Example 5(24)

N-{5-[(6,7-dimethoxy-4-quinolinyl)oxy]-2-pyridinyl}-1-(1-hydroxy-3-methyl-2-butanyl)-2,5-dioxo-1,2,5,6,7,8-hexahydro-3-quinolinecarboxamide (LC-MS/ELSD): (retention time: 0.71 min);
MASS (ESI, Pos.): 573 (M+H)$^+$.

Example 5(25)

1-cyclobutyl-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.74 min);
MASS (ESI, Pos.): 541 (M+H)$^+$.

Example 5(26)

N-{5-[(6,7-dimethoxy-4-quinolinyl)oxy]-2-pyridinyl}-1-[1-(4-fluorophenyl)ethyl]-2,5-dioxo-1,2,5,6,7,8-hexahydro-3-quinolinecarboxamide (LC-MS/ELSD): (retention time: 0.80 min);
MASS (ESI, Pos.): 609 (M+H)$^+$.

Example 5(27)

N-{5-[(6,7-dimethoxy-4-quinolinyl)oxy]-2-pyridinyl}-2,5-dioxo-1-(3-pyridinyl)-1,2,5,6,7,8-hexahydro-3-quinolinecarboxamide (LC-MS/ELSD): (retention time: 0.63 min);
MASS (ESI, Pos.): 564 (M+H)$^+$.

Example 5(28)

N-{5-[(6,7-dimethoxy-4-quinolinyl)oxy]-2-pyridinyl}-1-[2-(dimethylamino)ethyl]-2,5-dioxo-1,2,5,6,7,8-hexahydro-3-quinolinecarboxamide (LC-MS/ELSD): (retention time: 0.51 min);
MASS (ESI, Pos.): 558 (M+H)$^+$.

Example 5(29)

N-{5-[(6,7-dimethoxy-4-quinolinyl)oxy]-2-pyridinyl}-1-(2-methoxy-2-methylpropyl)-2,5-dioxo-1,2,5,6,7,8-hexahydro-3-quinolinecarboxamide TLC: Rf 0.65 (dichloromethane:methanol=9:1);
$^1$H-NMR (CDCl$_3$): δ 1.19-1.35, 2.18, 2.62, 2.81, 3.16, 3.83, 4.06, 4.07, 4.99, 6.45, 7.27, 7.44, 7.56, 7.59, 8.31, 8.51, 8.54, 9.23, 12.24.

Example 5(30)

N-{5-[(6,7-dimethoxy-4-quinolinyl)oxy]-2-pyridinyl}-1-(3-hydroxy-3-methyl-2-butanyl)-2,5-dioxo-1,2,5,6,7,8-hexahydro-3-quinolinecarboxamide (LC-MS/ELSD): (retention time: 0.70 min);
MASS (ESI, Pos.): 573 (M+H)$^+$.

Example 5(31)

N-{5-[(6,7-dimethoxy-4-quinolinyl)oxy]-2-pyridinyl}-1-(3-oxetanyl)-2,5-dioxo-1,2,5,6,7,8-hexahydro-3-quinolinecarboxamide (LC-MS/ELSD): (retention time: 0.68 min);
MASS (ESI, Pos.): 543 (M+H)$^+$.

Example 5(32)

1-(4,4-difluorocyclohexyl)-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.80 min);
MASS (ESI, Pos.): 605 (M+H)$^+$.

Example 5(33)

N-{5-[(6,7-dimethoxy-4-quinolinyl)oxy]-2-pyridinyl}-1-(1-methyl-1H-pyrazole-4-yl)-2,5-dioxo-1,2,5,6,7,8-hexahydro-3-quinolinecarboxamide (LC-MS/ELSD): (retention time: 0.63 min);
MASS (ESI, Pos.): 567 (M+H)$^+$.

Example 5(34)

1-(cyclopropylmethyl)-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.75 min);
MASS (ESI, Pos.): 541 (M+H)$^+$.

Example 5(35)

N-{5-[(6,7-dimethoxy-4-quinolinyl)oxy]-2-pyridinyl}-1-(3-methyl-2-butanyl)-2,5-dioxo-1,2,5,6,7,8-hexahydro-3-quinolinecarboxamide (LC-MS/ELSD): (retention time: 0.82 min);
MASS (ESI, Pos.): 557 (M+H)$^+$.

Example 5(36)

N-{5-[(6,7-dimethoxy-4-quinolinyl)oxy]-2-pyridinyl}-1-hexyl-2,5-dioxo-1,2,5,6,7,8-hexahydro-3-quinolinecarboxamide (LC-MS/ELSD): (retention time: 0.88 min);
MASS (ESI, Pos.): 571 (M+H)$^+$.

Example 5(37)

1-[(1S)-1-cyclohexylethyl]-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.92 min);
MASS (ESI, Pos.): 597 (M+H)$^+$.

Example 5(38)

N-{5-[(6,7-dimethoxy-4-quinolinyl)oxy]-2-pyridinyl}-2,5-dioxo-1-(3-phenylpropyl)-1,2,5,6,7,8-hexahydro-3-quinolinecarboxamide (LC-MS/ELSD): (retention time: 0.85 min);
MASS (ESI, Pos.): 605 (M+H)$^+$.

Example 5(39)

1-[(1S)-1-cyclopropylethyl]-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.79 min);
MASS (ESI, Pos.): 555 (M+H)$^+$.

Example 5(40)

1-[(1R)-1-cyclopropylethyl]-N-{5-[(6,7-dimethoxy-4-quinolinyl)oxy]-2-pyridinyl}-2,5-dioxo-1,2,5,6,7,8-hexahydro-3-quinolinecarboxamide (LC-MS/ELSD): (retention time: 0.80 min);
MASS (ESI, Pos.): 555 (M+H)$^+$.

Example 5(41)

N-{5-[(6,7-dimethoxy-4-quinolinyl)oxy]-2-pyridinyl}-1-(4-methylphenyl)-2,5-dioxo-1,2,5,6,7,8-hexahydro-3-quinolinecarboxamide TLC: Rf 0.66 (ethyl acetate:methanol=9:1);
$^1$H-NMR (CDCl$_3$): δ 2.10, 2.48, 2.60, 4.05, 6.44, 7.13, 7.42, 7.53, 7.56, 8.21, 8.49, 8.50, 9.31, 11.94.

Example 5(42)

1-(4-chlorophenyl)-N-{5-[(6,7-dimethoxy-4-quinolinyl)oxy]-2-pyridinyl}-2,5-dioxo-1,2,5,6,7,8-hexahydro-3-quinolinecarboxamide TLC: Rf 0.60 (ethyl acetate:methanol=9:1);
$^1$H-NMR (CDCl$_3$): δ 2.13, 2.60, 4.05, 6.45, 7.22, 7.42, 7.53, 7.57, 7.61, 8.23, 8.48, 8.50, 9.31, 11.85.

Example 5(43)

1-(2,4-difluorophenyl)-N-{5-[(6,7-dimethoxy-4-quinolinyl)oxy]-2-pyridinyl}-2,5-dioxo-1,2,5,6,7,8-hexahydro-3-quinolinecarboxamide TLC: Rf 0.33 (ethyl acetate);
$^1$H-NMR (CDCl$_3$): δ 2.17, 2.62, 4.06, 6.44, 7.14, 7.31, 7.43, 7.54, 7.57, 8.24, 8.50, 9.33, 11.79.

Example 5(44)

1-(2-chlorophenyl)-N-{5-[(6,7-dimethoxy-4-quinolinyl)oxy]-2-pyridinyl}-2,5-dioxo-1,2,5,6,7,8-hexahydro-3-quinolinecarboxamide TLC: Rf 0.29 (ethyl acetate);
$^1$H-NMR (CDCl$_3$): δ 2.14, 2.54, 2.64, 4.05, 6.44, 7.34, 7.43, 7.55, 7.57, 7.69, 8.23, 8.49, 8.51, 9.35, 11.85.

Example 5(45)

N-{5-[(6,7-dimethoxy-4-quinolinyl)oxy]-2-pyridinyl}-1-(2-methylphenyl)-2,5-dioxo-1,2,5,6,7,8-hexahydro-3-quinolinecarboxamide TLC: Rf 0.36 (ethyl acetate);
$^1$H-NMR (CDCl$_3$): δ 2.08-2.15, 2.36, 2.58-2.65, 4.05, 6.44, 7.15, 7.43-7.59, 8.23, 8.48-8.52, 9.35, 11.97.

Example 5(46)

N-{5-[(6,7-dimethoxy-4-quinolinyl)oxy]-2-pyridinyl}-1-[(1R)-2-hydroxy-1-phenylethyl]-2,5-dioxo-1,2,5,6,7,8-hexahydro-3-quinolinecarboxamide TLC: Rf 0.15 (ethyl acetate, NH silica);
$^1$H-NMR (CDCl$_3$): δ 2.14, 2.48, 3.04, 3.30, 4.04, 4.05, 4.51, 5.11, 6.22, 7.19-7.42, 7.53, 7.73, 8.16, 8.40, 8.51, 8.86, 11.89.

Example 5(47)

N-{5-[(6,7-dimethoxy-4-quinolinyl)oxy]-2-pyridinyl}-1-[(1S)-2-hydroxy-1-phenylethyl]-2,5-dioxo-1,2,5,6,7,8-hexahydro-3-quinolinecarboxamide TLC: Rf 0.51 (ethyl acetate:methanol=10:1);
$^1$H-NMR (CDCl$_3$): δ 2.08-2.25, 2.30-2.70, 2.97-3.16, 3.16-3.40, 4.05, 4.06, 4.45-4.60, 4.88-5.19, 5.67-6.15, 6.26, 7.16-7.42, 7.53, 7.72, 8.18, 8.43, 8.52, 8.94, 11.90.

Example 5(48)

N-{5-[(6,7-dimethoxy-4-quinolinyl)oxy]-2-pyridinyl}-2,5-dioxo-1-[(1R)-1-phenylethyl]-1,2,5,6,7,8-hexahydro-3-quinolinecarboxamide TLC: Rf 0.51 (ethyl acetate);
$^1$H-NMR (CDCl$_3$): δ 1.99-2.10, 2.40-2.70, 2.91, 4.06, 6.45, 7.21, 7.30-7.43, 7.55, 7.58, 8.29, 8.52, 9.26, 12.14.

Example 5(49)

N-{5-[(6,7-dimethoxy-4-quinolinyl)oxy]-2-pyridinyl}-1-[(2S)-3-methyl-2-butanyl]-2,5-dioxo-1,2,5,6,7,8-hexahydro-3-quinolinecarboxamide TLC: Rf 0.51 (ethyl acetate:methanol=10:1)
$^1$H-NMR (CDCl$_3$): δ 0.74, 1.07, 1.70, 2.10-2.40, 2.48-2.73, 2.95-3.15, 3.96, 4.06, 4.07, 6.45, 7.43, 7.52-7.64, 8.31, 8.47-8.56, 9.21, 12.27.

Example 5(50)

1-(3-chlorophenyl)-N-{5-[(6,7-dimethoxy-4-quinolinyl)oxy]-2-pyridinyl}-2,5-dioxo-1,2,5,6,7,8-hexahydro-3-quinolinecarboxamide TLC: Rf 0.72 (ethyl acetate:methanol=19:1);
$^1$H-NMR (DMSO-d$_6$): δ 1.98-2.07, 2.48-2.60, 3.93, 6.54, 7.40, 7.45-7.51, 7.67-7.69, 7.90, 8.36, 8.41, 8.48, 8.97, 11.89.

Example 5(51)

N-{5-[(6,7-dimethoxy-4-quinolinyl)oxy]-2-pyridinyl}-1-(3-methylphenyl)-2,5-dioxo-1,2,5,6,7,8-hexahydro-3-quinolinecarboxamide TLC: Rf 0.38 (ethyl acetate:methanol=19:1);
$^1$H-NMR (DMSO-d$_6$): δ 1.89-2.04, 2.36-2.62, 3.92-3.94, 6.54, 7.10-7.56, 7.86, 8.35, 8.42, 8.47-8.49, 8.97, 11.97.

Example 5(52)

N-{5-[(6,7-dimethoxy-4-quinolinyl)oxy]-2-pyridinyl}-1-[(2R)-3-methyl-2-butanyl]-2,5-dioxo-1,2,5,6,7,8-hexahydro-3-quinolinecarboxamide TLC: Rf 0.48 (ethyl acetate:methanol=10:1);
$^1$H-NMR (CDCl$_3$): δ 0.74, 1.07, 1.70, 2.10-2.38, 2.49-2.75, 2.93-3.15, 3.88-4.02, 4.06, 4.07, 6.45, 7.43, 7.52-7.63, 8.31, 8.46-8.58, 9.21, 12.27.

Example 5(53)

N-{5-[(6,7-dimethoxy-4-quinolinyl)oxy]-2-pyridinyl}-1-[1-(2-hydroxy-2-methylpropyl)-1H-pyrazole-4-yl]-2,5-dioxo-1,2,5,6,7,8-hexahydro-3-quinolinecarboxamide TLC: Rf 0.15 (ethyl acetate, NH silica);
$^1$H-NMR (CDCl$_3$): δ 1.27, 2.14, 2.59, 2.73, 3.20, 4.05, 4.18, 6.44, 7.43, 7.53, 7.54, 7.70, 8.24, 8.49, 8.51, 9.28, 11.88.

Example 5(54)

N-{5-[(6,7-dimethoxy-4-quinolinyl)oxy]-2-pyridinyl}-2,5-dioxo-1-phenyl-2,5,6,7,8,9-hexahydro-1H-cyclohepta[b]piperidine-3-carboxamide TLC: Rf 0.32 (ethyl acetate);
$^1$H-NMR (CDCl$_3$): δ 1.80, 1.91, 2.71, 2.77, 4.05, 6.45, 7.25, 7.43, 7.53-7.66, 8.21, 8.48, 8.50, 9.11, 11.99.

Example 6

1-(4-fluorophenyl)-N-{5-[(7-methoxy-4-quinolinyl)oxy]-2-pyridinyl}-2,5-dioxo-1,2,5,6,7,8-hexahydro-3-quinolinecarboxamide

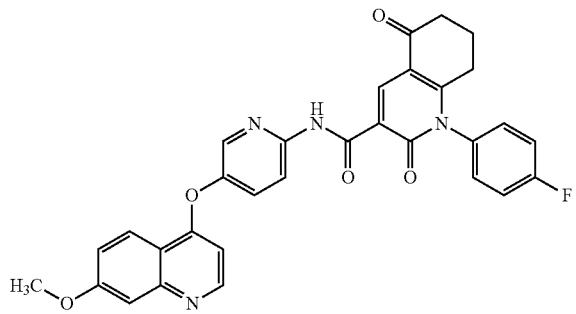 [SMILES: COc1ccc2c(Oc3ccc(NC(=O)c4cc5c(n(-c6ccc(F)cc6)c4=O)CCCC5=O)nc3)ccnc2c1]

The title compound having the following physical property values was obtained by the procedure having the same purpose as in Example 1→Example 2→Example 3→Example 4→Example 5, using 4-chloro-7-methoxy quinoline (CAS registration No.: 68500-37-8) in place of 4-chloro-6,7-dimethoxy quinoline.

TLC: Rf 0.73 (ethyl acetate:methanol=19:1);
$^1$H-NMR (CDCl$_3$): δ 1.92-2.09, 2.40-2.70, 3.93, 6.54, 7.29, 7.41-7.60, 7.87, 8.21, 8.36, 8.41, 8.61, 8.97, 11.94.

Example 6(1) to 6(38)

The following Example compounds were obtained by the procedure having the same purpose as in Example 6, using 4-chloro-7-methoxy quinoline or a corresponding quinoline derivative in place of it and the compound produced in Example 4 or a corresponding carboxylic acid derivative in place of it.

Example 6(1)

N-{5-[(7-methoxy-4-quinolinyl)oxy]-2-pyridinyl}-2,5-dioxo-1-phenyl-1,2,5,6,7,8-hexahydro-3-quinolinecarboxamide TLC: Rf 0.30 (ethyl acetate, NH silica);
$^1$H-NMR (DMSO-d$_6$): δ 1.98, 2.45-2.57, 3.92, 6.52, 7.28, 7.40, 7.44, 7.46, 7.57-7.67, 7.85, 8.20, 8.35, 8.40, 8.60, 8.97, 11.95.

Example 6(2)

N-{5-[(6-methoxy-4-quinolinyl)oxy]-2-pyridinyl}-2,
5-dioxo-1-phenyl-1,2,5,6,7,8-hexahydro-3-quinolinecarboxamide (LC-MS/ELSD): (retention time: 0.77 min);
$^1$H-NMR (CDCl$_3$): δ 2.05-2.20, 2.51-2.68, 3.97, 6.52, 7.25-7.26, 7.27-7.29, 7.41, 7.54-7.67, 8.00, 8.22, 8.50, 8.55, 9.33, 11.93.

Example 6(3)

1-[(2S)-1-hydroxy-3-methyl-2-butanyl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.71 (ethyl acetate:methanol=5:1);
$^1$H-NMR (CDCl$_3$): δ 0.72, 1.12, 2.18, 2.48, 2.92-3.02, 3.31, 3.95, 4.04, 4.17, 4.77, 5.23, 6.23, 7.21, 7.78, 8.21, 8.24, 8.51, 8.55, 8.77, 12.16.

Example 6(4)

1-[(2R)-1-hydroxy-3-methyl-2-butanyl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.71 (ethyl acetate:methanol=5:1);
$^1$H-NMR (CDCl$_3$): δ 0.72, 1.12, 2.18, 2.48, 2.92-3.02, 3.31, 3.95, 4.04, 4.17, 4.77, 5.23, 6.23, 7.21, 7.78, 8.21, 8.24, 8.51, 8.55, 8.77, 12.16.

Example 6(5)

1-(3-fluorophenyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.43 (ethyl acetate:methanol=19:1);
$^1$H-NMR (CDCl$_3$): δ 1.93-2.08, 2.40-2.65, 3.93, 6.54, 7.27-7.55, 7.65-7.76, 7.87, 8.21, 8.34-8.47, 8.62, 8.98, 11.91.

Example 6(6)

2,5-dioxo-1-phenyl-N-(5-{[7-(trifluoromethyl)-4-quinolinyl]oxy}-2-pyridinyl)-1,2,5,6,7,8-hexahydro-3-quinolinecarboxamide (LC-MS/ELSD): (retention time: 1.06 min);
$^1$H-NMR (DMSO-d$_6$): δ 2.00, 2.52-2.55, 6.88, 7.46-7.48, 7.58-7.66, 7.93-7.96, 8.40-8.44, 8.46, 8.57, 8.85, 8.99, 11.99.

Example 6(7)

1-cyclobutyl-N-{5-[(7-methoxy-4-quinolinyl)oxy]-2-pyridinyl}-2,5-dioxo-1,2,5,6,7,8-hexahydro-3-quinolinecarboxamide TLC: Rf 0.69 (ethyl acetate:methanol=19:1);
$^1$H-NMR (DMSO-d$_6$): δ 1.70-1.90, 1.95-2.10, 2.35-2.60, 2.73-2.89, 3.04-3.15, 3.94, 4.89-5.03, 6.55, 7.30, 7.42, 7.88, 8.22, 8.40, 8.42, 8.62, 8.83, 12.16.

Example 6(8)

1-(2,2-dimethylpropyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.65 (ethyl acetate:methanol=19:1);
$^1$H-NMR (DMSO-d$_6$): δ 0.99, 2.00-2.16, 2.48-2.65, 3.15-3.22, 3.94, 4.12-4.38, 6.55, 7.30, 7.42, 7.88, 8.22, 8.39, 8.42, 8.62, 8.90, 12.20.

Example 6(9)

N-{5-[(7-methoxy-4-quinolinyl)oxy]-2-pyridinyl}-6,6-dimethyl-2,5-dioxo-1-phenyl-1,2,5,6,7,8-hexahydro-3-quinolinecarboxamide TLC: Rf 0.55 (ethyl acetate:methanol=19:1);
$^1$H-NMR (DMSO-d$_6$): δ 1.13, 1.80-1.90, 2.34-2.56, 3.92, 6.54, 7.29, 7.41, 7.48-7.68, 7.87, 8.20, 8.35, 8.41, 8.61, 8.99, 11.98.

Example 6(10)

1-(4-chlorophenyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.52 (ethyl acetate:methanol=19:1);
$^1$H-NMR (DMSO-d$_6$): δ 1.91-2.04, 2.37-2.60, 3.93, 6.54, 7.29, 7.41, 7.52, 7.72, 7.88, 8.20, 8.34, 8.41, 8.61, 8.97, 11.91.

Example 6(11)

N-{5-[(7-methoxy-4-quinolinyl)oxy]-2-pyridinyl}-1-(4-methylphenyl)-2,5-dioxo-1,2,5,6,7,8-hexahydro-3-quinolinecarboxamide TLC: Rf 0.41 (ethyl acetate:methanol=19:1);
$^1$H-NMR (DMSO-d$_6$): δ 1.91-2.03, 2.42, 2.40-2.60, 3.93, 6.54, 7.26-7.46, 7.87, 8.20, 8.36, 8.41, 8.61, 8.96, 11.97.

Example 6(12)

1-(4,4-difluorocyclohexyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.50 (ethyl acetate, NH silica);
$^1$H-NMR (CDCl$_3$): δ 1.81, 2.25, 2.31, 2.62, 3.08, 3.30, 3.98, 4.10, 6.43, 7.25, 7.42, 7.57, 8.24, 8.30, 8.51, 8.61, 9.19, 12.08.

Example 6(13)

1-(cyclopropylmethyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.55 (ethyl acetate, NH silica);
$^1$H-NMR (CDCl$_3$): δ 0.62, 1.15, 2.26, 2.64, 3.15, 3.98, 4.20, 6.43, 7.23, 7.42, 7.57, 8.23, 8.29, 8.51, 8.61, 9.22, 12.23.

Example 6(14)

1-[(1R)-1-cyclopropylethyl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.55 (ethyl acetate, NH silica);
$^1$H-NMR (CDCl$_3$): δ 0.06, 0.30, 0.56, 0.77, 1.80, 2.24, 2.60, 2.89, 3.43, 3.98, 6.44, 7.22, 7.43, 7.56, 8.23, 8.30, 8.51, 8.61, 9.20, 12.29.

Example 6(15)

1-[(1S)-1-cyclopropylethyl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.55 (ethyl acetate, NH silica);
$^1$H-NMR (CDCl$_3$): δ 0.06, 0.30, 0.56, 0.77, 1.80, 2.24, 2.60, 2.89, 3.43, 3.98, 6.44, 7.22, 7.43, 7.56, 8.23, 8.30, 8.51, 8.61, 9.20, 12.29.

Example 6(16)

1-(4-fluorophenyl)-N-{5-[(6-methoxy-4-quinolinyl)oxy]-2-pyridinyl}-2,5-dioxo-1,2,5,6,7,8-hexahydro-3-quinolinecarboxamide TLC: Rf 0.69 (ethyl acetate:methanol=5:1);
$^1$H-NMR (CDCl$_3$): δ 2.13, 2.60, 3.97, 6.52, 7.29-7.35, 7.41, 7.55-7.60, 8.00, 8.23, 8.49, 8.54, 9.32, 11.88.

Example 6(17)

1-isobutyl-N-{5-[(7-methoxy-4-quinolinyl)oxy]-2-pyridinyl}-2,5-dioxo-1,2,5,6,7,8-hexahydro-3-quinolinecarboxamide TLC: Rf 0.34 (ethyl acetate:methanol=19:1);
$^1$H-NMR (DMSO-d$_6$): 0.94, 2.08-2.20, 2.40-2.60, 3.12-3.26, 3.94, 4.12, 6.55, 7.30, 7.42, 7.88, 8.22, 8.39, 8.41, 8.62, 8.90, 12.24.

Example 6(18)

N-{5-[(7-methoxy-4-quinolinyl)oxy]-2-pyridinyl}-2',5'-dioxo-1'-phenyl-2',5',6',8'-tetrahydro-1'H-spiro[cyclobutane-1,7'-quinoline]-3'-carboxamide TLC: Rf 0.56 (ethyl acetate:methanol=19:1);
$^1$H-NMR (DMSO-d$_6$): δ 1.65-1.91, 2.63-2.74, 3.93, 7.29, 7.45, 7.46-7.53, 7.58-7.71, 7.87, 8.20, 8.36, 8.41, 8.61, 8.94, 11.94.

Example 6(19)

1-(2,4-difluorophenyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.51 (ethyl acetate);
$^1$H-NMR (CDCl$_3$): δ 2.16, 2.62, 3.97, 6.42, 7.10-7.33, 7.42, 7.56, 8.21-8.24, 8.49, 8.60, 9.33, 11.79.

Example 6(20)

1-(2-chlorophenyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.40 (ethyl acetate);
$^1$H-NMR (CDCl$_3$): δ 2.14, 2.55, 2.63, 3.97, 6.41, 7.23, 7.35, 7.42, 7.53-7.58, 7.68, 8.21, 8.23, 8.49, 8.60, 9.34, 11.84.

Example 6(21)

N-{5-[(7-methoxy-4-quinolinyl)oxy]-2-pyridinyl}-1-(2-methylphenyl)-2,5-dioxo-1,2,5,6,7,8-hexahydro-3-quinolinecarboxamide TLC: Rf 0.44 (ethyl acetate);
$^1$H-NMR (CDCl$_3$): δ 2.15-2.20, 2.35, 2.58-2.67, 3.97, 6.41, 7.15, 7.24, 7.41-7.49, 7.56, 8.21, 8.23, 8.49, 8.60, 9.34, 11.96.

Example 6(22)

1-[1-(hydroxymethyl)cyclobutyl]-N-{5-[(6-methoxy-4-quinolinyl)oxy]-2-pyridinyl}-2,5-dioxo-1,2,5,6,7,8-hexahydro-3-quinolinecarboxamide TLC: Rf 0.15 (ethyl acetate, NH silica);
$^1$H-NMR (CDCl$_3$): δ 1.87, 2.18, 2.40, 2.62, 2.94, 3.44, 3.98, 4.10, 4.18, 4.50, 6.46, 7.38, 7.58, 7.62, 7.92, 8.28, 8.49, 8.57, 9.02, 12.02.

Example 6(23)

1-[1-(hydroxymethyl)cyclobutyl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.15 (ethyl acetate, NH silica);
$^1$H-NMR (CDCl$_3$): δ 1.95, 2.21, 2.38-2.69, 2.95, 3.42, 3.68, 3.97, 4.15, 4.46, 6.40, 7.23, 7.39, 7.61, 8.24, 8.28, 8.53, 8.58, 9.10, 11.99.

Example 6(24)

N-{5-[(6-methoxy-4-quinolinyl)oxy]-2-pyridinyl}-1-(2-methylphenyl)-2,5-dioxo-1,2,5,6,7,8-hexahydro-3-quinolinecarboxamide TLC: Rf 0.25 (ethyl acetate, NH silica);
$^1$H-NMR (CDCl$_3$): δ 2.12, 2.26, 2.60, 3.97, 6.51, 7.15, 7.40-7.49, 7.58, 8.00, 8.23, 8.49, 8.55, 9.34, 11.98.

Example 6(25)

1-(2-chlorophenyl)-N-{5-[(6-methoxy-4-quinolinyl)oxy]-2-pyridinyl}-2,5-dioxo-1,2,5,6,7,8-hexahydro-3-quinolinecarboxamide TLC: Rf 0.25 (ethyl acetate, NH silica);
$^1$H-NMR (CDCl$_3$): δ 2.15, 2.57, 2.63, 3.97, 6.51, 7.35-7.61, 7.68, 8.00, 8.23, 8.50, 8.55, 9.34, 11.86.

Example 6(26)

1-(2,4-difluorophenyl)-N-{5-[(6-methoxy-4-quinolinyl)oxy]-2-pyridinyl}-2,5-dioxo-1,2,5,6,7,8-hexahydro-3-quinolinecarboxamide TLC: Rf 0.25 (ethyl acetate, NH silica);
$^1$H-NMR (CDCl$_3$): δ 2.18, 2.62, 3.97, 6.51, 7.18, 7.21-7.40, 7.41, 7.57, 8.01, 8.24, 8.50, 8.55, 9.32, 11.79.

Example 6(27)

1-[(1S)-1-cyclopropylethyl]-N-{5-[(6-methoxy-4-quinolinyl)oxy]-2-pyridinyl}-2,5-dioxo-1,2,5,6,7,8-hexahydro-3-quinolinecarboxamide TLC: Rf 0.60 (ethyl acetate:methanol=10:1);
$^1$H-NMR (CDCl$_3$): δ 0.03-0.13, 0.20-0.40, 0.49-0.67, 0.69-0.89, 1.81, 2.09-2.42, 2.47-2.72, 2.89, 3.31-3.52, 3.98, 6.53, 7.42, 7.55-7.64, 8.00, 8.31, 8.53, 8.56, 9.21, 12.30.

Example 6(28)

1-[(1S)-2-hydroxy-1-phenylethyl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.54 (ethyl acetate:methanol=10:1);
$^1$H-NMR (CDCl$_3$): δ 2.07-2.29, 2.36-2.68, 2.97-3.16, 3.17-3.43, 3.96, 4.45-4.62, 4.95-5.23, 5.68-6.05, 6.22, 7.12-7.43, 7.72, 8.17, 8.23, 8.47-8.56, 8.86, 11.90.

Example 6(29)

1-[(1R)-1-(4-fluorophenyl)ethyl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.58 (ethyl acetate);
$^1$H-NMR (CDCl$_3$): δ 2.00, 2.05, 2.40-2.80, 2.96, 3.98, 6.43, 7.08, 7.18-7.29, 7.42, 7.58, 8.24, 8.28, 8.51, 8.61, 9.25, 12.07.

Example 6(30)

N-{5-[(7-methoxy-4-quinolinyl)oxy]-2-pyridinyl}-2,5-dioxo-1-[(1R)-1-phenylethyl]-1,2,5,6,7,8-hexahydro-3-quinolinecarboxamide TLC: Rf 0.58 (ethyl acetate);
$^1$H-NMR (CDCl$_3$): δ 1.99-2.10, 2.40-2.70, 2.90, 3.98, 6.43, 7.22, 7.27-7.43, 7.59, 8.24, 8.28, 8.52, 8.61, 9.26, 12.13.

Example 6(31)

1-(2-fluorophenyl)-N-{5-[(6-methoxy-4-quinolinyl)oxy]-2-pyridinyl}-2,5-dioxo-1,2,5,6,7,8-hexahydro-3-quinolinecarboxamide TLC: Rf 0.60 (ethyl acetate:methanol=10:1);
$^1$H-NMR (CDCl$_3$): δ 2.06-2.25, 2.63, 3.97, 6.52, 7.42, 7.51-7.67, 7.99, 8.23, 8.50, 8.55, 9.33, 11.85.

Example 6(32)

1-(3-fluorophenyl)-N-{5-[(6-methoxy-4-quinolinyl)oxy]-2-pyridinyl}-2,5-dioxo-1,2,5,6,7,8-hexahydro-3-quinolinecarboxamide TLC: Rf 0.66 (ethyl acetate:methanol=10:1);
$^1$H-NMR (CDCl$_3$): δ 2.04-2.26, 2.53-2.70, 3.97, 6.52, 6.99-7.14, 7.27-7.36, 7.37-7.44, 7.52-7.68, 7.99, 8.23, 8.49, 8.55, 9.32, 11.85.

Example 6(33)

N-{5-[(7-methoxy-4-quinolinyl)oxy]-2-pyridinyl}-1-[(2S)-3-methyl-2-butanyl]-2,5-dioxo-1,2,5,6,7,8-hexahydro-3-quinolinecarboxamide TLC: Rf 0.57 (ethyl acetate:methanol=10:1);
$^1$H-NMR (CDCl$_3$): δ 0.74, 1.07, 1.70, 2.10-2.34, 2.45-2.76, 2.94-3.14, 3.86-3.96, 3.98, 6.42, 7.21-7.25, 7.43, 7.58, 8.24, 8.30, 8.52, 8.61, 9.21, 12.27.

Example 6(34)

1-(2-fluorophenyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.35 (ethyl acetate:methanol=19:1);
$^1$H-NMR (DMSO-d$_6$): δ 1.96-2.18, 2.30-2.60, 3.93, 6.54, 7.29, 7.41, 7.44-7.72, 7.88, 8.21, 8.36, 8.41, 8.61, 9.00, 11.81.

Example 6(35)

N-{5-[(7-methoxy-4-quinolinyl)oxy]-2-pyridinyl}-1-(3-methylphenyl)-2,5-dioxo-1,2,5,6,7,8-hexahydro-3-quinolinecarboxamide TLC: Rf 0.50 (ethyl acetate:methanol=19:1);
$^1$H-NMR (DMSO-d$_6$): δ 1.94-2.05, 2.40, 2.45-2.60, 3.93, 6.54, 7.22-7.55, 7.87, 8.21, 8.36, 8.42, 8.62, 8.97, 11.97.

Example 6(36)

1-(3-chlorophenyl)-N-{5-[(7-methoxy-4-quinolinyl)oxy]-2-pyridinyl}-2,5-dioxo-1,2,5,6,7,8-hexahydro-3-quinolinecarboxamide TLC: Rf 0.74 (ethyl acetate:methanol=19:1);
$^1$H-NMR (DMSO-d$_6$): δ 1.98-2.07, 2.45-2.60, 3.93, 6.54, 7.29, 7.41, 7.46-7.51, 7.66-7.69, 7.87, 8.20, 8.36, 8.41, 8.61, 8.97, 11.89.

Example 6(37)

N-{5-[(7-methoxy-4-quinolinyl)oxy]-2-pyridinyl}-1-[(2R)-3-methyl-2-butanyl]-2,5-dioxo-1,2,5,6,7,8-hexahydro-3-quinolinecarboxamide TLC: Rf 0.55 (ethyl acetate:methanol=10:1);
$^1$H-NMR (CDCl$_3$): δ 0.74, 1.07, 1.70, 2.12-2.38, 2.47-2.74, 2.95-3.20, 3.90-3.95, 3.98, 6.43, 7.20-7.25, 7.43, 7.58, 8.24, 8.30, 8.52, 8.61, 9.21, 12.26.

Example 6(38)

1-[1-(2-hydroxy-2-methylpropyl)-1H-pyrazole-4-yl]-N-{5-[(7-methoxy-4-quinolinyl)oxy]-2-pyridinyl}-2,5-dioxo-1,2,5,6,7,8-hexahydro-3-quinolinecarboxamide TLC: Rf 0.15 (ethyl acetate, NH silica);

$^1$H-NMR (CDCl$_3$): δ 1.28, 2.14, 2.62, 2.75, 3.10, 3.97, 4.18, 6.41, 7.22, 7.42, 7.52-7.60, 7.70, 8.21, 8.23, 8.48, 8.60, 9.27, 11.87.

Example 7 tert-butyl N-[5-[(6,7-dimethoxy-4-quinazolinyl)amino]-2-pyridyl] carbamate 4-chloro-6,7-dimethoxyquinazoline (CAS registration No.: 13790-39-1) (450 mg) and tert-butyl (5-aminopyridin-2-yl)carbamate (420 mg) were dissolved in N,N-dimethyl acetamide (DMA) (20 mL) at room temperature. 4 mol/L hydrochloric acid-dioxane (0.5 mL) was added thereto at 50° C., and the mixture was stirred. Thereafter, the resulting solution was heated to 80° C. and stirred for three hours. The resulting solution was left to cool to room temperature, methyl tert-butyl ether (MTBE) was added to the reaction solution, solids precipitated from the reaction solution were collected by filtration through Kiriyama funnel, and washed with MTBE. The resulting residue was dried under reduced pressure at 60° C. The title compound (821 mg) having the following physical property values was obtained.

TLC: Rf 0.45 (ethyl acetate:methanol=5:1);

$^1$H-NMR (DMSO-d$_6$): δ 1.49, 4.00, 7.34, 7.88, 8.05, 8.32, 8.56, 8.84, 10.02, 11.54.

Example 8

N$^5$-(6,7-dimethoxy-4-quinazolinyl)pyridine-2,5-diamine

The compound (800 mg) produced in Example 7 was dissolved in dichloromethane (10 mL) at room temperature, trifluoroacetic acid (0.3 mL) was added thereto, and the mixture was stirred at room temperature for six hours. The reaction solution was diluted with ethyl acetate, and saturated sodium bicarbonate water was added to the reaction solution and stirred. Ethyl acetate and water were further added, and the organic layer was extracted. THF and water were added to the water layer, and the organic layer was extracted. The organic layer was collected, washed with a saturated saline solution, dried over anhydrous sodium sulfate, and the solvent was distilled off under reduced pressure. Ethyl acetate and hexane were added to the resulting residue, followed by stirring at room temperature. The solid was washed with ether in a slurry form. The residue collected by filtration through Kiriyama funnel was dried under reduced pressure at 60° C. to obtain the title compound (598 mg) having the following physical property values.

TLC: Rf 0.16 (ethyl acetate:methanol=5:1);

$^1$H-NMR (DMSO-d$_6$): δ 3.91, 5.83, 6.49, 7.12, 7.65, 7.82, 8.09, 8.30, 9.36.

Example 9

N-{5-[(6,7-dimethoxy-4-quinazolinyl)amino]-2-pyridinyl}-2,5-dioxo-1-phenyl-1,2,5,6,7,8-hexahydro-3-quinolinecarboxamide

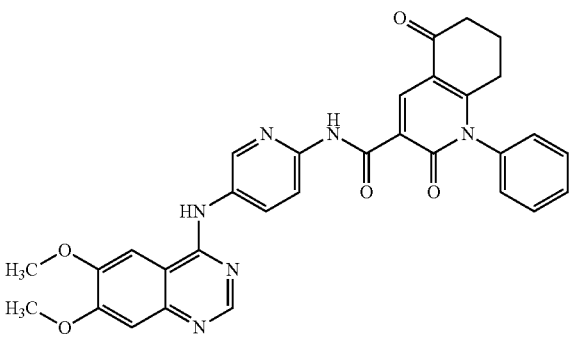

The compound produced in Example 4 (76 mg) and HATU (154 mg) were dissolved in DMF (1 mL) at room temperature. To the resulting solution, DIPEA (0.14 mL) and the compound produced in Example 8 (80 mg) were added, and the mixture was stirred for 18 hours. The reaction solution was diluted with ethyl acetate, and saturated sodium bicarbonate water was added and stirred. Ethyl acetate and water were further added, and the organic layer was extracted. The organic layer was washed with a saturated saline solution, dried over anhydrous sodium sulfate, and the solvent was distilled off under reduced pressure. The resulting residue was purified by silica gel chromatography (hexane:ethyl acetate=30:70→0:100→ethyl acetate:methanol=70:30) to obtain the title compound (57 mg) having the following physical property values.

TLC: Rf 0.59 (ethyl acetate:methanol=5:1);

$^1$H-NMR (CDCl$_3$): δ 2.10, 2.58, 4.04, 7.04, 7.13, 7.25, 7.59, 8.20, 8.41, 8.50, 8.64, 9.30, 11.82.

Examples 9(1) to 9(4)

The following Example compounds were obtained by the procedure having the same purpose as in Example 7→Example 8→Example 9, using 4-chloro-6,7-dimethoxyquinazoline or a corresponding quinoline derivative in place of it, tert-butyl (5-aminopyridin-2-yl)carbamate or a corresponding amine derivative in place of it, and the compound produced in Example 4.

Example 9(1)

N-{5-[(6,7-dimethoxy-4-quinolinyl)amino]-2-pyridinyl}-2,5-dioxo-1-phenyl-1,2,5,6,7,8-hexahydro-3-quinolinecarboxamide trifluoroacetate TLC: Rf 0.21 (dichloromethane:methanol=10:1);

$^1$H-NMR (DMSO-d$_6$): δ 1.86-2.14, 2.49-2.62, 3.98, 4.02, 6.75, 7.35-7.40, 7.41-7.52, 7.53-7.73, 7.94-8.07, 8.36-8.56, 8.99, 10.42, 12.03, 14.00.

Example 9(2)

N-{4-[(6,7-dimethoxy-4-quinolinyl)amino]phenyl}-2,5-dioxo-1-phenyl-1,2,5,6,7,8-hexahydro-3-quinolinecarboxamide (LC-MS/ELSD): (retention time: 0.75 min);

$^1$H-NMR (CD$_3$OD): δ 2.04-2.13, 2.56-2.64, 4.01, 4.02, 6.82, 7.24, 7.35-7.42, 7.59-7.67, 7.69, 7.75-7.79, 8.19, 9.17.

Example 9(3)

N-{5-[(7-methoxy-4-quinolinyl)amino]-2-pyridinyl}-2,5-dioxo-1-phenyl-1,2,5,6,7,8-hexahydro-3-quinolinecarboxamide TLC: Rf 0.63 (ethyl acetate:methanol:ammonia water=9:1:0.5);
$^1$H-NMR (DMSO-$d_6$): δ 1.90-2.05, 2.40-2.60, 3.89, 6.70, 7.18, 7.25, 7.42-7.50, 7.54-7.68, 7.86, 8.22-8.40, 8.97, 8.99, 11.85.

Example 9(4)

N-{4-[(6,7-dimethoxy-4-quinazolinyl)amino]phenyl}-2,5-dioxo-1-phenyl-1,2,5,6,7,8-hexahydro-3-quinolinecarboxamide (LC-MS/ELSD): (retention time: 0.79 min);
$^1$H-NMR (CD$_3$OD): δ 1.94-2.07, 2.50-2.58, 3.94, 3.96, 7.18, 7.43-7.51, 7.57-7.68, 7.75, 7.87, 8.50, 8.95, 9.69, 11.48.

Example 10

5-[(E)-{[3-(benzyloxy)phenyl]imino}methyl]-2,2-dimethyl-1,3-dioxane-4,6-dione 3-benzyloxyaniline (25 g), meldrum's acid (22 g), ethyl orthoformate (22 g), and ethanol (25 mL) were placed in a 200-mL eggplant flask. The mixture was heated and refluxed for 80 min, and left to cool to room temperature. Then, the precipitated powder was collected by filtration. The powder was washed with ethanol (50 mL) and dried to obtain the title compound (43 g) having the following physical property values.
TLC: Rf 0.48 (hexane:ethyl acetate=2:1);
$^1$H-NMR (DMSO-$d_6$): δ 1.66, 5.15, 6.88, 7.11, 7.30-7.45, 8.60, 11.2.

Example 11

7-(benzyloxy)-4(1H)-quinolinone

The compound produced in Example 10 (42 g) and 1,2-dichlorobenzene (420 mL) were placed in a 1 L-eggplant flask. The mixture was heated and refluxed for 5.5 hours, and left to cool to room temperature. Then, the precipitated powder was collected by filtration. The powder was washed with methanol (84 mL) and dried to obtain the title compound (18 g) having the following physical property values.
TLC: Rf 0.60 (ethyl acetate:methanol=9:1);
$^1$H-NMR (DMSO-$d_6$): δ 5.19, 5.92, 6.98, 7.32-7.43, 7.77, 7.97.

Example 12

7-(benzyloxy)-4-chloroquinolinone

Under argon atmosphere, the compound produced in Example 11 (17 g), toluene (34 mL) and phosphorus oxychloride (10 g) were placed in a 300-mL eggplant flask. The mixture was heated and refluxed for 2.5 hours, left to cool to 70° C., and diluted with ethyl acetate (135 mL). Thereafter, the mixture was left to cool to room temperature, and was neutralized by 2 mol/L sodium hydroxide aqueous solution. The resulting solution was extracted with ethyl acetate, washed with a saturated saline solution and dried over anhydrous sodium sulfate. Thereby, the solvent was distilled off under reduced pressure to obtain the title compound (18 g) having the following physical property values.
TLC: Rf 0.60 (hexane:ethyl acetate=2:1);
$^1$H-NMR (CDCl$_3$): δ 5.22, 7.34-7.51, 8.13, 8.86.

Example 13

7-(benzyloxy)-4-[(6-chloro-3-pyridinyl)oxy]quinolinone
The compound produced in Example 12 (15 g), 6-chloropyridine-3-ol (8.3 g), 4-dimethylaminopyridine (7.5 g), and toluene (75 mL) were placed in a 300-mL eggplant flask. The mixture was heated at 110° C. for 6.5 hours, then left to cool to room temperature. Water and ethyl acetate were added thereto, and the resulting solution was separated. The extract solution was washed with a saturated saline solution, dried over anhydrous sodium sulfate, and the solvent was distilled off under reduced pressure. Then, the resulting residue was dissolved in a small amount of ethyl acetate, and crystallized by adding methanol to the solution. The precipitates were then collected by filtration to obtain the title compound (15 g) having the following physical property values.
TLC: Rf 0.37 (hexane:ethyl acetate=1:1);
$^1$H-NMR (CDCl$_3$): δ 5.24, 6.46, 7.31-7.52, 8.19, 8.34, 8.65.

Example 14

5-{[7-(benzyloxy)-4-quinolinyl] oxy}-2-pyridinamine
Under argon atmosphere, a solution of the compound produced in Example 13 (5 g) in THF (25 mL), 1.0 mol/L LHMDS (3.5 mL), tris(dibenzylideneacetone) dipalladium (0) chloroform complex (0.63 g), and 2-dicyclohexylphosphino-2',6'-dimethoxybiphenyl (0.73 g) were placed in a 200-mL 4-diameter eggplant flask, and the mixture was stirred at 70° C. Disappearance of the raw material was confirmed, the resulting product was left to cool to room temperature, then water and ethyl acetate were added, and the solution was separated. After extraction with ethyl acetate, the solution was washed with a saturated saline solution, dried over anhydrous sodium sulfate, and the solvent was distilled off under reduced pressure. The resulting residue was suspended in acetonitrile (100 mL), and 2.0 mol/L hydrochloric acid (10 mL) was added to the suspension, and the mixture was stirred at room temperature for 2.5 hours. 1.0 mol/L sodium hydroxide aqueous solution, a saturated sodium hydrogen bicarbonate aqueous solution, and ethyl acetate were added, and the solution was separated. The extracted solution was washed with a saturated saline solution, dried over anhydrous sodium sulfate, and the solvent was distilled off under reduced pressure. The resulting residue was purified by silica gel column chromatography (hexane:ethyl acetate=1:1-0:1) to obtain the title compound (2.9 g) having the following physical property values.
TLC: Rf 0.33 (dichloromethane:ethyl acetate:methanol=8:4:1);
$^1$H-NMR (DMSO-$d_6$): δ 5.29, 6.06, 6.41, 6.55, 7.31-7.52, 7.88, 8.20, 8.56.

Example 15

N-(5-{[7-(benzyloxy)-4-quinolinyl]oxy}-2-pyridinyl)-2,5-dioxo-1-phenyl-1,2,5,6,7,8-hexahydro-3-quinolinecarboxamide

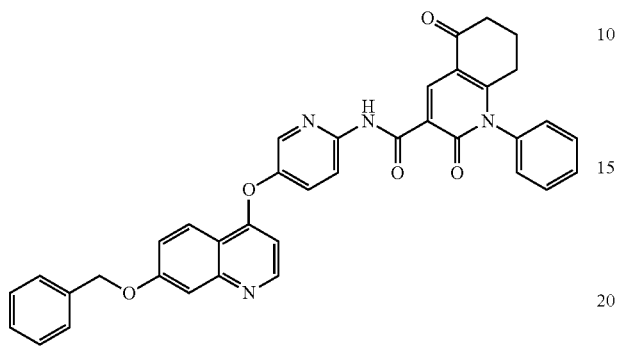

The compound produced in Example 14 (800 mg), the compound produced in Example 4 (660 mg), DIPEA (1.2 mL), and DMF (16 mL) were placed in a 30-mL eggplant flask, and finally HATU (1.1 g) was added thereto, followed by stirring at room temperature overnight. After disappearance of the raw material was confirmed, water and ethyl acetate were added, and the resulting solution was separated. The resulting solution was extracted with ethyl acetate, and then washed with water and a saturated saline solution sequentially in this order, and dried over anhydrous sodium sulfate. The solvent was distilled off under reduced pressure. The resulting residue was dissolved in a small amount of ethyl acetate, and crystallized by adding methanol. The precipitate was filtered to obtain the title compound (1.2 g) having the following physical property values.

TLC: Rf 0.74 (ethyl acetate:methanol=9:1);
$^1$H-NMR (CDCl$_3$): δ 2.11, 2.59, 5.23, 6.42, 7.25-7.63, 8.20, 8.24, 8.49, 8.59, 9.32, 11.92.

Example 16

N-{5-[(7-hydroxy-4-quinolinyl)oxy]-2-pyridinyl}-2,5-dioxo-1-phenyl-1,2,5,6,7,8-hexahydro-3-quinolinecarboxamide

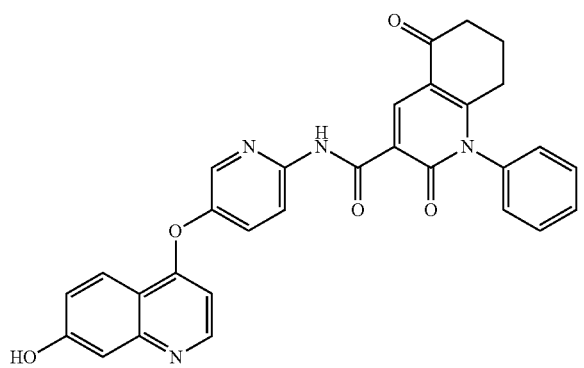 [SMILES: O=C1CCCc2c1cc(C(=O)Nc1ccc(Oc3ccnc4cc(O)ccc34)cn1)c(=O)n2-c1ccccc1]

The compound produced in Example 15 (500 mg), 20% palladium hydroxide-carbon (250 mg), ethyl acetate (18 mL), and methanol (2 mL) were placed in a 200-mL eggplant flask. Under hydrogen atmosphere, the mixture was stirred at room temperature for four hours, followed by filtration through Celite. The filtrate was distilled off under reduced pressure to obtain the title compound (360 mg) having the following physical property values.

TLC: Rf 0.63 (ethyl acetate:methanol=9:1);
$^1$H-NMR (DMSO-d$_6$): δ 2.00, 2.50, 6.44, 7.19, 7.25, 7.46, 7.60, 7.85, 8.15, 8.34, 8.41, 8.53, 8.97, 10.28, 11.95.

Example 17

N-[5-({7-[3-(dimethylamino)propoxy]-4-quinolinyl}oxy)-2-pyridinyl]-2,5-dioxo-1-phenyl-1,2,5,6,7,8-hexahydro-3-quinolinecarboxamide

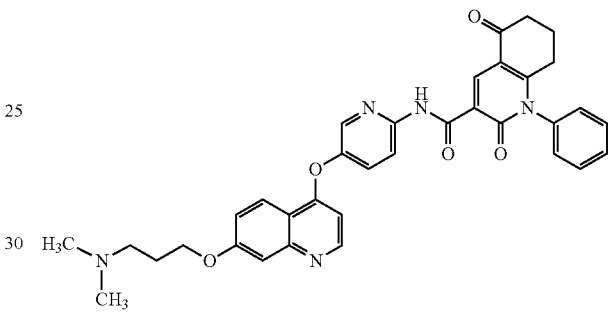

The compound produced in Example 16 (50 mg) was dissolved in THF (1 mL) at room temperature, and 3-(dimethylamino)-1-propanol (30 mg), 1,1'-azobis(N,N-dimethylformamide) (50 mg), and tributylphosphine (0.071 mL) were added sequentially. The mixture was stirred at 60° C. for 20 hours, and the solvent was distilled off under reduced pressure. The resulting residue was purified by silica gel chromatography (hexane:ethyl acetate=30:70→0:100→ethyl acetate:methanol=70:30) to obtain the title compound (22 mg) having the following physical property values.

TLC: Rf 0.75 (ethyl acetate:methanol=5:1, NH silica);
$^1$H-NMR (CDCl$_3$): δ 2.11, 2.34, 2.59, 4.19, 6.40, 7.25, 7.40, 7.54, 7.62, 8.20, 8.23, 8.49, 8.59, 9.33, 11.92.

Examples 17(1) to 17(8)

The following Example compounds were obtained by the procedure having the same purpose as in Example 16→Example 17, using the compound produced in Example 16 and corresponding alcohol derivatives in place of 3-(dimethylamino)-1-propanol.

Example 17(1)

N-(5-{[7-(3-hydroxy-3-methylbutoxy)-4-quinolinyl]oxy}-2-pyridinyl)-2,5-dioxo-1-phenyl-1,2,5,6,7,8-hexahydro-3-quinolinecarboxamide TLC: Rf 0.78 (ethyl acetate:methanol=5:1, NH silica);
$^1$H-NMR (CDCl$_3$): δ 1.35, 2.09, 2.60, 4.36, 6.41, 7.21, 7.44, 7.55, 7.58-7.65, 8.21, 8.22, 8.49, 8.60, 9.32, 11.92.

Example 17(2)

N-[5-({7-[3-(4-morpholinyl)propoxy]-4-quinolinyl}oxy)-2-pyridinyl]2,5-dioxo-1-phenyl-1,2,5,6,7,8-hexahydro-3-quinolinecarboxamide TLC: Rf 0.33 (ethyl acetate, DNH silica);
$^1$H-NMR (CDCl$_3$): δ 2.00-2.20, 2.45-2.52, 2.53-2.65, 3.72-3.75, 4.18-4.22, 6.40-6.42, 7.20-7.30, 7.40-7.41, 7.53-7.70, 8.19-8.22, 8.47-8.50, 8.58-8.60, 9.32, 11.92.

Example 17(3)

N-[5-({7-[2-(4-morpholinyl)ethoxy]-4-quinolinyl}oxy)-2-pyridinyl]-2,5-dioxo-1-phenyl-1,2,5,6,7,8-hexahydro-3-quinolinecarboxamide TLC: Rf 0.80 (ethyl acetate:methanol=5:1, NH silica);
$^1$H-NMR (CDCl$_3$): δ 2.10, 2.56-2.64, 2.90, 3.76, 4.29, 6.42, 7.22-7.28, 7.40, 7.53-7.65, 8.20, 8.22, 8.49, 8.60, 9.33, 11.92.

Example 17(4)

1-[(2S)-1-hydroxy-3-methyl-2-butanyl]-N-[5-({7-[3-(4-morpholinyl)propoxy]-4-quinolinyl}oxy)-2-pyridinyl]-2,5-dioxo-1,2,5,6,7,8-hexahydro-3-quinolinecarboxamide TLC: Rf 0.18 (ethyl acetate, DNH silica);
$^1$H-NMR (CDCl$_3$): δ 0.73, 1.13, 1.98-2.11, 2.12-2.26, 2.38-2.63, 2.82-3.08, 3.18-3.41, 3.70-3.79, 3.99-4.08, 4.09-4.27, 4.56-4.79, 6.26, 7.21, 7.26-7.29, 7.74, 8.18-8.27, 8.48-8.59, 8.86, 12.15.

Example 17(5)

1-(2,2-dimethylpropyl)-N-[5-({7-[3-(4-morpholinyl)propoxy]-4-quinolinyl}oxy)-2-pyridin yl]-2,5-dioxo-1,2,5,6,7,8-hexahydro-3-quinolinecarboxamide TLC: Rf 0.41 (ethyl acetate, DNH silica);
$^1$H-NMR (CDCl$_3$): δ 1.06, 2.01-2.13, 2.14-2.30, 2.44-2.52, 2.53-2.69, 3.01-3.16, 3.67-3.79, 4.21, 6.42, 7.23, 7.42, 7.57, 8.23, 8.29, 8.53, 8.60, 9.22, 12.18.

Example 17(6)

1-(1-methyl-1H-pyrazole-4-yl)-N-[5-({7-[3-(4-morpholinyl)propoxy]-4-quinolinyl}oxy)-2-pyridinyl]-2,5-dioxo-1,2,5,6,7,8-hexahydro-3-quinolinecarboxamide TLC: Rf 0.50 (ethyl acetate:methanol=10:1, NH silica);
$^1$H-NMR (CDCl$_3$): δ 2.01-2.21, 2.46-2.52, 2.54-2.66, 2.76, 3.69-3.77, 4.03, 4.20, 6.42, 7.22, 7.41, 7.52, 7.53-7.60, 8.17-8.26, 8.48, 8.59, 9.28, 11.90.

Example 17(7)

1-[1-(2-hydroxy-2-methylpropyl)-1H-pyrazole-4-yl]-N-[5-({7-[3-(4-morpholinyl)propoxy]-4-quinolinyl}oxy)-2-pyridinyl]-2,5-dioxo-1,2,5,6,7,8-hexahydro-3-quinolinecarboxamide TLC: Rf 0.50 (ethyl acetate:methanol=10:1, NH silica);
$^1$H-NMR (CDCl$_3$): δ 1.28, 2.01-2.22, 2.45-2.53, 2.54-2.66, 2.69-2.80, 3.20, 3.68-3.78, 4.16-4.25, 6.41, 7.19-7.25, 7.41, 7.52-7.60, 7.69, 8.16-8.26, 8.49, 8.59, 9.28, 11.87.

Example 17(8)

1-[(1R)-1-(4-fluorophenyl)ethyl]-N-[5-({7-[3-(4-morpholinyl)propoxy]-4-quinolinyl}oxy)-2-pyridinyl]-2,5-dioxo-1,2,5,6,7,8-hexahydro-3-quinolinecarboxamide TLC: Rf 0.62 (ethyl acetate:methanol=10:1, NH silica);
$^1$H-NMR (CDCl$_3$): δ 1.93-2.17, 2.41-2.64, 2.81-3.13, 3.74, 4.21, 6.42, 7.02-7.13, 7.18-7.26, 7.42, 7.57, 8.23, 8.28, 8.51, 8.60, 9.25, 11.99-12.11.

Example 18

(4-bromophenyl)(6,7-dimethoxy-4-quinazolinyl)methanone

At room temperature, 4-chloro-6,7-dimethoxyquinazoline (224 mg), 4-bromobenzaldehyde (221 mg), and 1,3-dimethyl imidazolium iodide (74 mg) were placed in a 50-mL eggplant flask, and the mixture was suspended in 1,4-dioxane (3 mL). At room temperature, 60% sodium hydride (52 mg) was added and stirred. Thereafter, the mixture was heated to 100° C. and stirred for one hour. The mixture was left to cool to room temperature, the reaction solution was diluted with ethyl acetate (10 mL), and water was added to the solution (10 mL). The precipitated crystals were collected by filtration to obtain the title compound (196 mg) having the following physical property values.

TLC: Rf 0.31 (hexane:ethyl acetate=1:1);
$^1$H-NMR (CDCl$_3$): δ 3.99, 4.10, 7.42, 7.43, 7.64-7.68, 7.84-7.88, 9.23.

Example 19

2-methyl-2-propanyl {4-[(6,7-dimethoxy-4-quinazolinyl)carbonyl]phenyl}carbamate

Under argon atmosphere, the compound produced in Example 18 (149 mg), tert-butyl carbamate (51 mg), tris(dibenzylideneacetone)dipalladium-chloroform adduct (21 mg), 4,5-bis(diphenylphosphino)-9,9-dimethylxanthene (35 mg), and cesium carbonate (182 mg) were suspended in 1,4-dioxane (4 mL) in a 50-mL eggplant flask. Thereafter, the suspension was heated to 100° C., stirred for 12 hours, and then left to cool to room temperature. Water was added thereto, followed by extraction with ethyl acetate. The extracted solution was washed with water and a saturated saline solution, and then dried over anhydrous sodium sulfate. Thereafter, the solvent was distilled off under reduced pressure, followed by purification by silica gel column chromatography (hexane:ethyl acetate=1:1) to obtain the title compound (145 mg) having the following physical property values.

TLC: Rf 0.17 (hexane:ethyl acetate=1:1);
$^1$H-NMR (CDCl$_3$): δ 1.53, 3.96, 4.09, 6.73, 7.33, 7.40, 7.47-7.51, 7.92-7.96, 9.22.

Example 20

(4-aminophenyl) (6,7-dimethoxy-4-quinazolinyl)methanone hydrochloride The compound produced in Example 19 (41 mg) was suspended was suspended in methanol (0.5 mL)

in a 50-mL eggplant flask at room temperature. 4 mol/L hydrogen chloride/ethyl acetate solution (1 mL) was added, and the reaction mixture was stirred at room temperature for one hour, and then concentrated to obtain the title compound (35 mg) having the following physical property values.

TLC: Rf 0.48 (dichloromethane:methanol=9:1);

$^1$H-NMR (DMSO-$d_6$): δ 3.79, 4.01, 6.57-6.60, 7.06, 7.46, 7.54-7.57, 9.14.

Example 21

N-{4-[(6,7-dimethoxy-4-quinazolinyl)carbonyl]phenyl}-2,5-dioxo-1-phenyl-1,2,5,6,7,8-hexahydro-3-quinolinecarboxamide

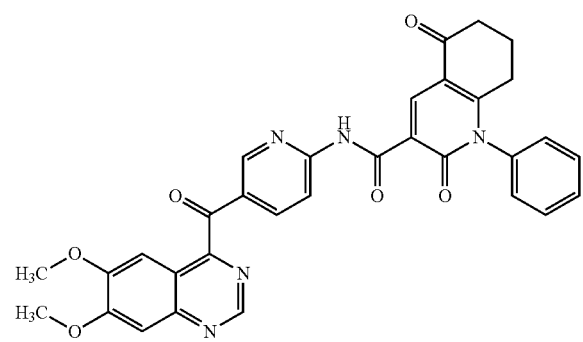 [SMILES: COc1cc2ncnc(C(=O)c3ccc(NC(=O)c4cc5c(n(-c6ccccc6)c4=O)CCCC5=O)nc3)c2cc1OC]

The title compound having the following physical property values was obtained by the procedure having the same purpose as in Example 5 using the compound produced in Example 20 and the compound produced in Example 4.

TLC: Rf 0.55 (dichloromethane:methanol=9:1);

$^1$H-NMR (CDCl$_3$): δ 2.06-2.14, 2.54-2.63, 3.95, 4.11, 7.26-7.29, 7.33, 7.41, 7.61-7.70, 7.82-7.86, 7.94-7.97, 9.23, 9.32, 11.70.

Example 22

4-[(6,7-dimethoxy-4-quinolyl)oxy] aniline 4-aminophenol (500 mg) was dissolved in dimethyl sulfoxide (DMSO) (5 mL) at room temperature, and 55% sodium hydride (98 mg) was added thereto. Thereafter, 4-chloro-6,7-dimethoxy quinoline (244 mg) was added, and the mixture was stirred at 100° C. for three hours. The reaction solution was diluted with ethyl acetate, saturated sodium bicarbonate water was added, and the mixture was stirred. Furthermore, ethyl acetate and water were added, and the organic layer was extracted. The organic layer was washed with a saturated saline solution, and then dried over anhydrous sodium sulfate. The solvent was distilled off under reduced pressure. The resulting residue was washed with methanol to obtain the title compound (442 mg) having the following physical property values.

TLC: Rf 0.57 (ethyl acetate);

$^1$H-NMR (CDCl$_3$): δ 3.71, 4.04, 6.41, 6.76, 6.98, 7.39, 7.57, 8.44.

Example 23

N-{4-[(6,7-dimethoxy-4-quinolinyl)oxy]phenyl}-2,5-dioxo-1-phenyl-1,2,5,6,7,8-hexahydro-3-quinolinecarboxamide

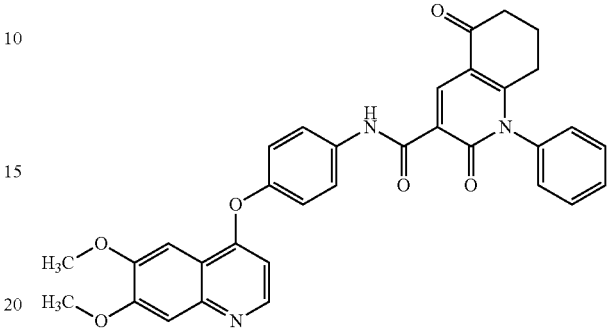

The title compound having the following physical property values was obtained by the procedure having the same purpose as in Example 5, using the compound produced in Example 22 and the compound produced in Example 4.

TLC: Rf 0.72 (ethyl acetate:methanol=5:1);

$^1$H-NMR (CDCl$_3$): δ 2.11, 2.60, 4.05, 6.49, 7.14, 7.28, 7.43, 7.56, 7.61-7.70, 7.80, 8.47, 9.34, 11.46.

Examples 23(1) to 23(3) The following Example compounds were obtained by the procedure having the same purpose as in Example 22→Example 23, using 4-chloro-6,7-dimethoxy quinoline or a corresponding quinoline derivative in place of it, 4-aminophenol or a corresponding phenol derivative in place of it.

Example 23(1)

2,5-dioxo-1-phenyl-N-[4-(4-quinolinyloxy)phenyl]-1,2,5,6,7,8-hexahydro-3-quinolinecarboxamide (LC-MS/ELSD): (retention time: 0.79 min);

$^1$H-NMR (CDCl$_3$): δ 2.05-2.18, 2.53-2.69, 6.56, 7.12-7.20, 7.26-7.34, 7.54-7.85, 8.08, 8.36, 8.66, 9.34, 11.45.

Example 23(2)

N-{4-[(6,7-dimethoxy-4-quinolinyl)oxy]-2-methylphenyl}-2,5-dioxo-1-phenyl-1,2,5,6,7,8-hexahydro-3-quinolinecarboxamide TLC: Rf 0.50 (dichloromethane:methanol=9:1);

$^1$H-NMR (CDCl$_3$): δ 2.05-2.15, 2.32, 2.53-2.63, 4.04, 4.05, 6.50, 7.00, 7.06, 7.26-7.30, 7.42, 7.55-7.68, 8.30, 8.48, 9.35, 11.23.

Example 23(3)

N-{4-[(6,7-dimethoxy-4-quinolinyl)oxy]-2,6-difluorophenyl}-2,5-dioxo-1-phenyl-1,2,5,6,7,8-hexahydro-3-quinolinecarboxamide TLC: Rf 0.28 (ethyl acetate);

$^1$H-NMR (CDCl$_3$): δ 2.06-2.14, 2.55-2.63, 4.03, 4.05, 6.69, 6.78-6.83, 7.26-7.30, 7.41, 7.45, 7.56-7.68, 8.58, 9.32, 10.77.

Example 24

4-(2-fluoro-4-nitrophenoxy)-6,7-dimethoxy quinoline 6,7-dimethoxy quinoline-4-ol (5.0 g), cesium carbonate (1.3 g) and 1,2-difluoro-4-nitrobenzene (3.5 mL) were added into DMF (20 mL), and the mixture was stirred at room temperature for six hours. The reaction solution was diluted with ethyl acetate, and then the organic layer was washed with water. The water layer was extracted with ethyl acetate twice, and the combined organic layer was washed with a saturated saline solution, and dried over anhydrous sodium sulfate. The organic layer was concentrated. The resulting residue was purified by silica gel column chromatography (hexane:ethyl acetate=1:1→0:100) to obtain the title compound (2.3 g) having the following physical property values.

TLC: Rf 0.62 (hexane:ethyl acetate=1:9);
$^1$H-NMR (CDCl$_3$): δ 4.04, 4.07, 6.55, 7.31-7.38, 7.45, 7.47, 8.11-8.26, 8.19, 8.58.

Example 25

4-[(6,7-dimethoxy quinoline-4-yl)oxy]-3-fluoroaniline

The compound produced in Example 24 (2.1 g) was dissolved in DMF:water=3:1 (45 mL). Zinc (3.9 g) and ammonium chloride (1.9 mg) were added to the solution, and the solution was stirred at room temperature for one hour. Then the reaction solution was filtered through Celite. Saturated sodium hydrogen carbonate aqueous solution was added to the filtrate and solid precipitate was removed by filtration through Celite. Ethyl acetate was added thereto, and the water layer was extracted with ethyl acetate. The combined organic layer was washed with a saturated saline solution, and dried over anhydrous sodium sulfate. The organic layer was concentrated. The title compound (1.9 g) having the following physical property values was obtained.

TLC: Rf 0.35 (hexane:ethyl acetate=1:9);
$^1$H-NMR (DMSO-d$_6$): δ 3.93, 5.48, 6.38, 6.42-6.48, 6.54, 7.06, 7.37, 7.49, 8.44.

Example 26

N-{4-[(6,7-dimethoxy-4-quinolinyl)oxy]-3-fluorophenyl}-2,5-dioxo-1-phenyl-1,2,5,6,7,8-hexahydro-3-quinolinecarboxamide

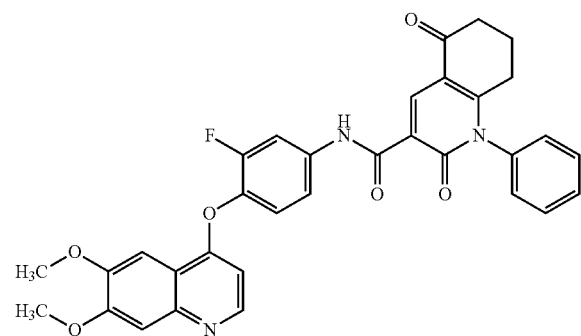 [SMILES: COc1cc2nccc(Oc3ccc(NC(=O)c4cc5c(n(-c6ccccc6)c4=O)CCCC5=O)cc3F)c2cc1OC]

The title compound having the following physical property values was obtained by the procedure having the same purpose as in Example 5 using the compound produced in Example 25 and the compound produced in Example 4.

TLC: Rf 0.17 (hexane:ethyl acetate=1:9);
$^1$H-NMR (CDCl$_3$): δ 2.06-2.20, 2.54-2.68, 4.06, 6.43, 7.15-7.47, 7.57-7.74, 7.94, 8.48, 9.32, 11.55.

Examples 26(1) to 26(3)

The following Example compounds were obtained by the procedure having the same purpose as in Example 26, using a carboxylic acid derivative was used in place of the compound produced in Example 4.

Example 26(1)

N-{4-[(6,7-dimethoxy-4-quinolinyl)oxy]-3-fluorophenyl}-1-(2,2-dimethylpropyl)-2,5-dioxo-1,2,5,6,7,8-hexahydro-3-quinolinecarboxamide TLC: Rf 0.36 (ethyl acetate);
$^1$H-NMR (DMSO-d$_6$): δ 0.99, 2.00-2.16, 2.54-2.60, 3.11-3.24, 3.94, 4.28, 6.47, 7.40-7.57, 8.05, 8.47, 8.84, 11.81.

Example 26(2)

N-{4-[(6,7-dimethoxy-4-quinolinyl)oxy]-3-fluorophenyl}-1-(3-fluorophenyl)-2,5-dioxo-1,2,5,6,7,8-hexahydro-3-quinolinecarboxamide

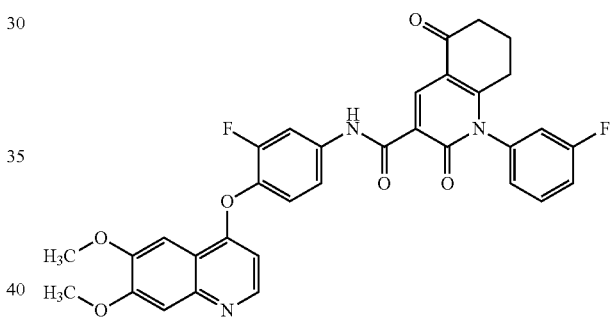

TLC: Rf 0.32 (ethyl acetate);
$^1$H-NMR (CDCl$_3$): δ 2.07-2.21, 2.51-2.71, 4.05, 4.06, 6.39-6.45, 7.01-7.13, 7.15-7.23, 7.29-7.40, 7.42, 7.57, 7.60-7.74, 7.85-8.00, 8.48, 9.33, 11.38-11.49.

Example 26(3)

N-{4-[(6,7-dimethoxy-4-quinolinyl)oxy]-3-fluorophenyl}-2',5'-dioxo-1'-phenyl-2',5',6',8'-tetrahydro-1'H-spiro[cyclopropane-1,7'-quinoline]-3'-carboxamide TLC: Rf 0.33 (ethyl acetate);
$^1$H-NMR (CDCl$_3$): δ 0.32-0.44, 0.50-0.61, 2.40, 2.48, 4.05, 4.06, 6.42, 7.14-7.25, 7.34-7.40, 7.42, 7.58, 7.59-7.70, 7.93, 8.49, 9.37, 11.54.

Example 27

4-[(6-chloro-3-pyridinyl)oxy]-6,7-dimethoxyquinazoline

Under argon atmosphere, DMAP (4.4 g) was added to 4-chloro-6,7-dimethoxyquinazoline (8.0 g) and a DMSO suspension (20 mL) of 6-chloropyridine-3-ol (4.6 g), heated and stirred at a bath temperature (80° C.) for two hours, and left to cool to room temperature. Thereafter, the reaction solution was diluted with ethyl acetate, and washed with water and saturated sodium hydrogen carbonate aqueous solution. The organic layer was dried over anhydrous sodium sulfate, and concentrated. The resulting residue was washed with hexane-ethyl acetate (3:1) to obtain the title compound (9.1 g) having the following physical property values.

TLC: Rf 0.16 (hexane:ethyl acetate=1:1);
$^1$H-NMR (DMSO-$d_6$): δ 3.97, 3.99, 7.41, 7.58, 7.69, 7.97, 8.50, 8.57.

Example 28

5-[(6,7-dimethoxy-4-quinazolinyl)oxy]-2-pyridinamine hydrochloride

Under argon atmosphere, 1.0 mol/L LHMDS (4.7 mL), tris(dibenzylideneacetone)dipalladium(0) chloroform complex (140 mg), and 2-dicyclohexylphosphino-2',6'-dimethoxybiphenyl (170 mg) were added to a THF solution (15 mL) of the compound produced in Example 27 (1.0 g). The mixture was stirred at a bath temperature (70° C.) for four hours. After the reaction solution was left to cool to room temperature, and placed into ice water, followed by extraction with ethyl acetate. The organic layer was washed with water, dried over anhydrous sodium sulfate, and concentrated. The resulting residue was suspended in acetonitrile (30 mL), and 2.0 mol/L hydrochloric acid (10 mL) was added thereto and stirred at room temperature for 30 min. Precipitates generated in the reaction solution were collected by filtration to obtain the title compound (591 mg) having the following physical property values.

TLC: Rf 0.16 (ethyl acetate:methanol=10:1);
$^1$H-NMR (DMSO-$d_6$): δ 3.96, 3.99, 4.24, 7.10, 7.42, 7.53, 8.00-8.20, 8.07, 8.20, 8.61.

Example 29

N-{5-[(6,7-dimethoxy-4-quinazolinyl)oxy]-2-pyridinyl}-2,5-dioxo-1-phenyl-1,2,5,6,7,8-hexahydro-3-quinolinecarboxamide

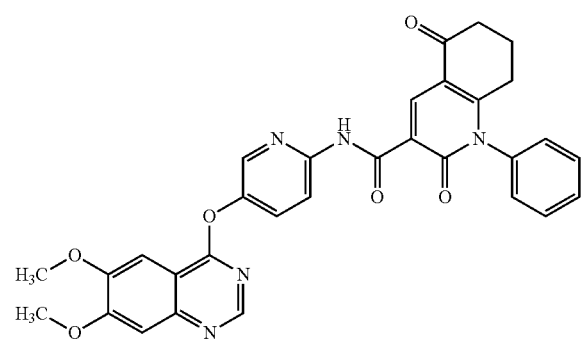 [SMILES: COc1cc2ncnc(Oc3ccc(NC(=O)c4cc5c(n(-c6ccccc6)c4=O)CCCC5=O)nc3)c2cc1OC]

The title compound having the following physical property values was obtained by the procedure having the same purpose as in Example 5 using the compound produced in Example 28 and the compound produced in Example 4.

TLC: Rf 0.75 (ethyl acetate:methanol=5:1);
$^1$H-NMR (CDCl$_3$): δ 2.11, 2.59, 4.07, 7.26, 7.33, 7.54, 7.58-7.69, 8.27, 8.52, 8.61, 9.33, 11.91.

Examples 29(1) to 29(6)

The following Example compounds were obtained by the procedure having the same purpose as in Example 27→Example 28→Example 29, using corresponding quinoline derivatives in place of 4-chloro-6,7-dimethoxyquinazoline, 6-chloropyridine-3-ol, and the compound produced in Example 4 or corresponding carboxylic acid derivatives in place of it.

Example 29(1)

N-{5-[(7-methoxy-4-quinazolinyl)oxy]-2-pyridinyl}-2,5-dioxo-1-phenyl-1,2,5,6,7,8-hexahydro-3-quinolinecarboxamide (LC-MS/ELSD): (retention time: 0.99 min);
$^1$H-NMR (CDCl$_3$): δ 2.02-2.21, 2.57, 3.99, 7.24-7.25, 7.27-7.29, 7.30-7.33, 7.55-7.69, 8.23, 8.26, 8.51, 8.67, 9.33, 11.89.

Example 29(2)

1-cyclobutyl-N-{5-[(6,7-dimethoxy-4-quinazolinyl)oxy]-2-pyridinyl}-2,5-dioxo-1,2,5,6,7,8-hexahydro-3-quinolinecarboxamide TLC: Rf 0.47 (ethyl acetate:methanol=10:1);
$^1$H-NMR (CDCl$_3$): δ 1.75-1.95, 1.96-2.10, 2.11-2.25, 2.40-2.54, 2.55-2.65, 2.92-3.16, 4.08, 4.09, 4.74-4.93, 7.34, 7.56, 7.68, 8.36, 8.56, 8.62, 9.16, 12.13.

Example 29(3)

N-{5-[(6,7-dimethoxy-4-quinazolinyl)oxy]-2-pyridinyl}-1-(2,2-dimethylpropyl)-2,5-dioxo-1,2,5,6,7,8-hexahydro-3-quinolinecarboxamide TLC: Rf 0.44 (ethyl acetate:methanol=10:1);
$^1$H-NMR (CDCl$_3$): δ 1.06, 2.18-2.27, 2.63, 3.02-3.18, 4.08, 4.09, 7.34, 7.56, 7.69, 8.36, 8.56, 8.61, 9.22, 12.17.

Example 29(4)

N-{5-[(6,7-dimethoxy-4-quinazolinyl)oxy]-2-pyridinyl}-1-[(2S)-1-hydroxy-3-methyl-2-butanyl]-2,5-dioxo-1,2,5,6,7,8-hexahydro-3-quinolinecarboxamide TLC: Rf 0.38 (ethyl acetate:methanol=10:1);
$^1$H-NMR (CDCl$_3$): δ 0.74, 1.13, 2.09-2.34, 2.41-2.72, 2.77-3.39, 3.90-4.20, 4.07, 4.09, 4.44-4.69, 7.32, 7.55, 7.70, 8.32, 8.53, 8.60, 9.15, 12.07.

Example 29(5)

N-{5-[(6,7-dimethoxy-4-quinazolinyl)oxy]-2-pyridinyl}-1-(4-fluorophenyl)-2,5-dioxo-1,2,5,6,7,8-hexahydro-3-quinolinecarboxamide

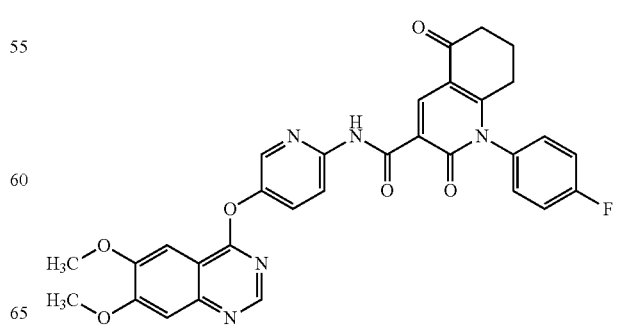

TLC: Rf 0.55 (hexane:ethyl acetate=1:9, NH silica);
$^1$H-NMR (CDCl$_3$): δ 2.12, 2.56-2.63, 4.07, 7.23-7.35, 7.53, 7.66, 8.26, 8.50, 8.60, 9.30, 11.84.

Example 29(6)

N-{5-[(6,7-dimethoxy-4-quinazolinyl)oxy]-2-pyridinyl}-1-[(2R)-1-hydroxy-3-methyl-2-butanyl]-2,5-dioxo-1,2,5,6,7,8-hexahydro-3-quinolinecarboxamide TLC: Rf 0.20 (ethyl acetate, NH silica);
$^1$H-NMR (CDCl$_3$): δ 0.72, 1.11, 2.22, 2.52, 2.94, 3.34, 4.07, 4.08, 4.16, 4.40, 4.72, 7.27, 7.54, 7.72, 8.24, 8.45, 8.56, 8.86, 91.5, 12.14.

Example 30

4-(2-fluoro-4-nitrophenyl)-7-methoxyquinazoline 4-chloro-7-methoxy-quinazoline (50 mg) and 2-fluoro-4-nitrophenol (60 mg) were added to diphenyl ether (10 mL), and the mixture was stirred at 150° C. for two hours by using microwave. The reaction solution was cooled, and water was added. Thereafter, the water layer was extracted with ethyl acetate, and the combined organic layer was washed with a saturated saline solution, and then concentrated. The resulting residue was purified by silica gel column chromatography (hexane:ethyl acetate=100:0-0:100) to obtain the title compound (60 mg) having the following physical property values.
MASS (ESI, Pos.): 286 (M+H)$^+$.

Example 31

3-fluoro-4-[7-methoxyquinazoline-4-yl)oxy] aniline The title compound having the following physical property values was obtained by the procedure having the same purpose as in Example 25, using the compound produced in Example 30.
$^1$H-NMR (CDCl$_3$): δ 3.70, 3.98, 6.49-6.57, 7.06, 7.24-7.30, 8.25, 9.47.

Example 32

N-{3-fluoro-4-[(7-methoxy-4-quinazolinyl)oxy]phenyl}-2,5-dioxo-1-phenyl-1,2,5,6,7,8-hexahydro-3-quinolinecarboxamide

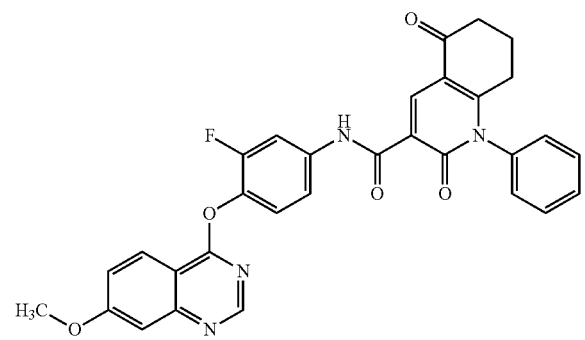 [SMILES: COc1ccc2c(Oc3ccc(NC(=O)c4cc5c(n(-c6ccccc6)c4=O)CCCC5=O)cc3F)ncnc2c1]

The title compound having the following physical property values was obtained by the procedure having the same purpose as in Example 5, using the compound produced in Example 31 and the compound produced in Example 4.
(LC-MS/ELSD): (retention time: 1.02 min);
$^1$H-NMR (CDCl$_3$): δ 2.06-2.20, 2.53-2.68, 3.98, 7.19-7.44, 7.58-7.73, 7.93, 8.25, 8.67, 9.32, 11.51.

Example 33 tert-butyl [4-(quinazoline-4-yloxy)phenyl]carbamate 4-chloro-quinazoline (0.95 g), calcium carbonate (3.5 g), and (4-hydroxy-phenyl)-carbamic acid tert-butyl ester (0.90 g) were added to acetonitrile (10 mL), and the mixture was stirred at 100° C. for three hours. Water was added to the reaction solution, and the water layer was extracted with ethyl acetate. The combined organic layer was washed with a saturated saline solution, and then concentrated. The resulting residue was purified by silica gel column chromatography (hexane:ethyl acetate=100:0-0:100) to obtain the title compound (1.3 g) having the following physical property values.
$^1$H-NMR (CDCl$_3$): δ 1.53, 6.63, 7.18-7.20, 7.47, 7.64-7.68, 7.89-7.93, 8.00, 8.37, 8.76.

Example 34

4-(quinazoline-4-yloxy)aniline Hydrochloride 4 mol/L hydrochloric acid-1,4-dioxane solution (5 mL) was added to a THF solution (5 mL) of the compound produced in Example 33 (100 mg), and the mixture was stirred at room temperature for three hours. The reaction solution was concentrated to obtain the title compound (81 mg) having the following physical property value.
MASS (ESI, Pos.): 238 (M+H)$^+$.

Example 35

2,5-dioxo-1-phenyl-N-[4-(4-quinazolinyloxy)phenyl]-1,2,5,6,7,8-hexahydro-3-quinolinecarboxamide

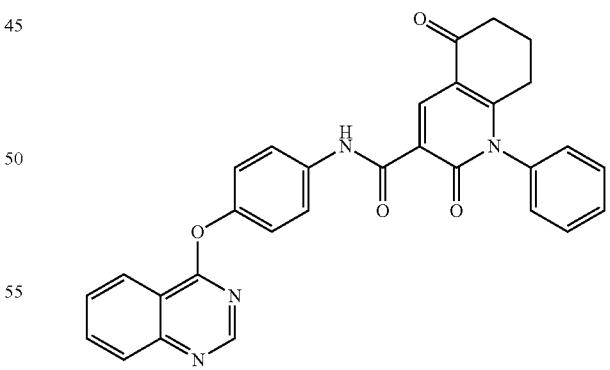

The title compound having the following physical property values was obtained by the procedure having the same purpose as in Example 5, using the compound produced in Example 34 and the compound produced in Example 4.
(LC-MS/ELSD): (retention time: 0.98 min);
$^1$H-NMR (CDCl$_3$): δ 2.08-2.13, 2.54-2.63, 7.21-7.29, 7.60-7.68, 7.82-7.84, 7.91-7.93, 8.00, 8.37, 8.76, 9.34, 11.43.

Example 36

5-{[(3-hydroxy-4-methoxyphenyl)amino]methylene}-2,2-dimethyl-1,3-dioxane-4,6-dione Under argon atmosphere, a methyl orthoformate (50 mL) solution of meldrum's acid (8.0 g) was heated at 100° C. for 5 min, and then 3-hydroxy-4-methoxyaniline (7.0 g) was added to the solution, and the resulting solution was heated and stirred at 105° C. for 25 min. The heating was stopped to cool with water, and precipitated powder was collected by filtration, washed with methyl orthoformate and MTBE, and dried under reduced pressure to obtain the title compound (12.3 g) having the following physical property values.

TLC: Rf 0.25 (hexane:ethyl acetate=1:1);
$^1$H-NMR (CDCl$_3$): δ 1.75, 3.92, 5.82, 6.73, 6.84-6.88, 8.53, 11.2.

Example 37

5-({[3-(benzyloxy)-4-methoxyphenyl]amino}methylene)-2,2-dimethyl-1,3-dioxane-4,6-dione Under argon atmosphere, the compound produced in Example 36 (12.0 g) was dissolved in DMA (80 mL) at 50° C. The temperature was returned to room temperature. Then, potassium carbonate (7.35 g) and benzyl bromide (8.75 g) were added thereto. The resulting solution was heated and stirred at 60° C. for two hours. The mixture was left to cool to room temperature, and the solvent was concentrated, followed by adding ethyl acetate and water and shaking thereof. Since deposits were precipitated, the deposits were collected by filtration, washed with water and ethyl acetate, and dried under reduced pressure to obtain the title compound (8.0 g) having the following physical property values.

TLC: Rf 0.49 (hexane:ethyl acetate=1:1);
$^1$H-NMR (CDCl$_3$): δ 1.75, 3.90, 5.17, 6.76-6.85, 6.91, 7.30-7.48, 8.48, 11.2.

Example 38

N-[5-({6-methoxy-7-[3-(4-morpholinyl)propoxy]-4-quinolinyl}oxy)-2-pyridinyl]-2,5-dioxo-1-phenyl-1,2,5,6,7,8-hexahydro-3-quinolinecarboxamide

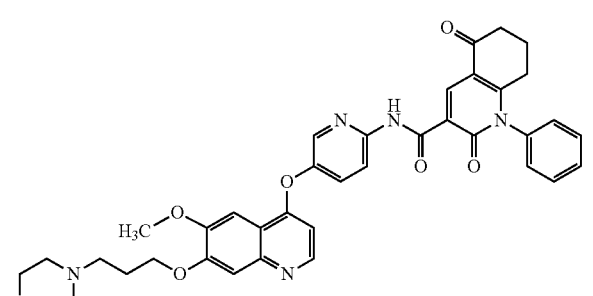

The title compound having the following physical property values was obtained by the procedure having the same purpose as in Example 11→Example 12→Example 13→Example 14→Example 15→Example 16→Example 17, using the compound produced in Example 37.

TLC: Rf 0.20 (ethyl acetate, NH silica);
$^1$H-NMR (CDCl$_3$): δ 2.08-2.19, 2.45-2.64, 3.73, 4.02, 4.27, 6.43, 7.25, 7.43, 7.52-7.65, 8.21, 8.47, 8.49, 9.32, 11.92.

Examples 38(1) to 38(7)

The following Example compounds were obtained by the procedure having the same purpose as in Example 38, using a corresponding compound in place of the compound produced in Example 37.

Example 38(1)

N-(5-{[7-(3-hydroxy-3-methylbutoxy)-6-methoxy-4-quinolinyl]oxy}-2-pyridinyl)-2,5-dioxo-1-phenyl-1,2,5,6,7,8-hexahydro-3-quinolinecarboxamide

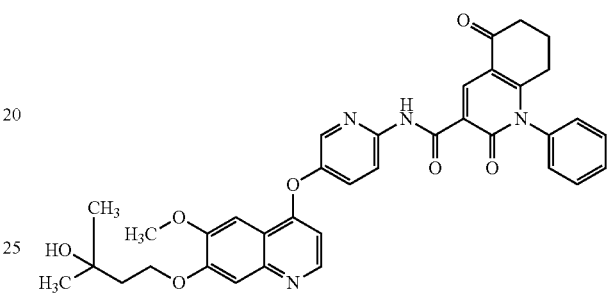

TLC: Rf 0.20 (ethyl acetate, NH silica);
$^1$H-NMR (CDCl$_3$): δ 1.34, 2.07-2.15, 2.56-2.64, 3.28, 4.01, 4.43, 6.45, 7.25, 7.43, 7.53-7.67, 8.21, 8.48, 8.51, 9.33, 11.93.

Example 38(2)

N-[5-({6-methoxy-7-[3-(1-piperidinyl)propoxy]-4-quinolinyl}oxy)-2-pyridinyl]-2,5-dioxo-1-phenyl-1,2,5,6,7,8-hexahydro-3-quinolinecarboxamide TLC: Rf 0.28 (ethyl acetate, NH silica);
$^1$H-NMR (CDCl$_3$): δ 1.42, 1.52-1.64, 2.08-2.15, 2.38-2.45, 2.50-2.63, 4.02, 4.24, 6.42, 7.21-7.28, 7.42, 7.51, 7.55-7.66, 8.21, 8.47, 8.49, 9.32, 11.92.

Example 38(3)

N-[5-({6-methoxy-7-[3-(1-pyrrolidinyl)propoxy]-4-quinolinyl}oxy)-2-pyridinyl]-2,5-dioxo-1-phenyl-1,2,5,6,7,8-hexahydro-3-quinolinecarboxamide

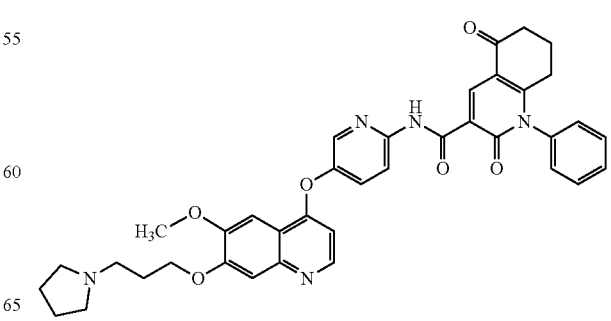

TLC: Rf 0.25 (ethyl acetate, NH silica);
$^1$H-NMR (CDCl$_3$): δ 1.79, 2.15, 2.56, 2.67, 4.02, 4.27, 6.42, 7.25, 7.42, 7.51, 7.53-7.65, 8.21, 8.47, 8.49, 9.32, 11.92.

Example 38(4)

N-[5-({6-methoxy-7-[3-(1-piperazinyl)propoxy]-4-quinolinyl}oxy)-2-pyridinyl]-2,5-dioxo-1-phenyl-1,2,5,6,7,8-hexahydro-3-quinolinecarboxamide TLC: Rf 0.20 (ethyl acetate, NH silica);
$^1$H-NMR (CDCl$_3$): δ 2.10, 2.55, 2.71, 3.15, 4.01, 4.26, 6.44, 7.26, 7.42, 7.51-7.67, 8.21, 8.49, 9.31, 11.92.

Example 38(5)

N-(5-{[7-(2-butyn-1-yloxy)-6-methoxy-4-quinolinyl]oxy}-2-pyridinyl)-2,5-dioxo-1-phenyl-1,2,5,6,7,8-hexahydro-3-quinolinecarboxamide TLC: Rf 0.56 (ethyl acetate:methanol=10:1);
$^1$H-NMR (CDCl$_3$): δ 1.86, 2.00-2.21, 2.48-2.74, 4.04, 4.90, 6.45, 7.22-7.31, 7.50-7.68, 8.22, 8.45-8.54, 9.33, 11.94.

Example 38(6)

N-[5-({6-methoxy-7-[3-(methylsulfonyl)propoxy]-4-quinolinyl}oxy)-2-pyridinyl]-2,5-dioxo-1-phenyl-1,2,5,6,7,8-hexahydro-3-quinolinecarboxamide TLC: Rf 0.16 (ethyl acetate:methanol=10:1, NH silica);
$^1$H-NMR (CDCl$_3$): δ 2.02-2.19, 2.40-2.68, 2.99, 3.29-3.40, 4.02, 4.32, 6.45, 7.22-7.29, 7.40, 7.49-7.69, 8.22, 8.44-8.55, 9.33, 11.94.

Example 38(7)

N-[5-({6-methoxy-7-[3-(4-methyl-1-piperazinyl)propoxy]-4-quinolinyl}oxy)-2-pyridinyl]-2,5-dioxo-1-phenyl-1,2,5,6,7,8-hexahydro-3-quinolinecarboxamide TLC: Rf 0.20 (ethyl acetate, NH silica);
$^1$H-NMR (CDCl$_3$): δ 2.13, 2.29, 2.48-2.65, 4.02, 4.25, 6.42, 7.21-7.28, 7.42, 7.51, 7.52-7.67, 8.21, 8.47, 8.49, 9.32, 11.92.

Example 39

N-[5-({7-[(3-methyl-2-buten-1-yl)oxy]-4-quinolinyl}oxy)-2-pyridinyl]-2,5-dioxo-1-phenyl-1,2,5,6,7,8-hexahydro-3-quinolinecarboxamide Under argon atmosphere, cesium carbonate (94 mg) and 1-bromo-3-methyl-2-butene (140 mg) were added to a DMF solution (15 mL) of the compound produced in Example 16 (100 mg), and the mixture was stirred at a bath temperature (−10° C.) for two hours. An ammonium chloride aqueous solution was added to the reaction solution, followed by extraction with ethyl acetate. The organic layer was washed with a saturated saline solution, dried over anhydrous sodium sulfate, and concentrated, followed by purification by silica gel column chromatography (hexane:ethyl acetate=1:4, NH silica) to obtain the title compound (55 mg).

TLC: Rf 0.30 (ethyl acetate, NH silica);
$^1$H-NMR (CDCl$_3$): δ 1.79, 1.82, 2.08-2.17, 2.46-2.63, 4.67, 5.57, 6.39, 7.23-7.26, 7.46, 7.48-7.65, 8.18, 8.22, 8.45, 8.49, 9.29, 11.90.

Example 40

N-{5-[(7-{[(2R)-2,3-dihydroxy-3-methylbutyl]oxy}-4-quinolinyl)oxy]-2-pyridinyl}-2,5-dioxo-1-phenyl-1,2,5,6,7,8-hexahydro-3-quinolinecarboxamide

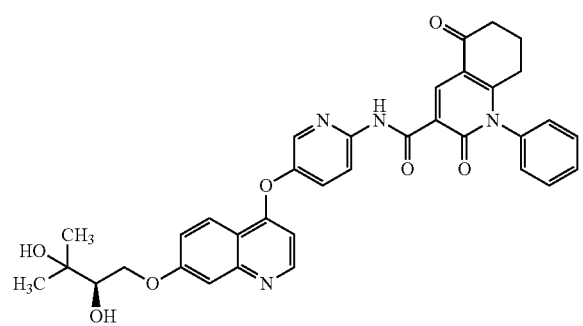 [SMILES: CC(C)(O)[C@H](O)COc1ccc2c(Oc3ccc(NC(=O)c4cc5c(n(-c6ccccc6)c4=O)CCCC5=O)nc3)ccnc2c1]

Under argon atmosphere, tert-butyl alcohol (0.5 mL), water (0.5 mL), AD-mix-β (50 mg), and methane sulfonamide (7 mg) were added to a dichloromethane solution (0.5 mL) of the compound produced in Example 39 (20 mg), and the mixture was stirred at room temperature for six hours. A sodium thiosulfate aqueous solution was added to the reaction solution, followed by extraction with ethyl acetate. The organic layer was washed with a saturated saline solution, dried over anhydrous sodium sulfate, and concentrated, followed by purification by silica gel column chromatography (ethyl acetate, NH silica) to obtain the title compound (3 mg).

TLC: Rf 0.10 (ethyl acetate, NH silica);
$^1$H-NMR (CDCl$_3$): δ 1.32, 1.36, 2.11, 2.37, 2.60, 2.87, 3.92, 4.20, 4.32, 6.42, 7.23, 7.43, 7.53-7.66, 8.20, 8.23, 8.48, 8.60, 9.32, 11.93.

Examples 40(1) to 40(6)

The following Example compounds were obtained by the procedure having the same purpose as in Example 39→Example 40, using a corresponding compound in place of the compound produced in Example 16, 1-bromo-3-methyl-2-butene, and AD-mix-β or AD-mix-α.

Example 40(1)

N-{5-[(7-{[(2S)-2,3-dihydroxy-3-methylbutyl]oxy}-6-methoxy-4-quinolinyl)oxy]-2-pyridinyl}-2,5-dioxo-1-phenyl-1,2,5,6,7,8-hexahydro-3-quinolinecarboxamide TLC: Rf 0.41 (ethyl acetate:methanol=10:1);
$^1$H-NMR (CDCl$_3$): δ 1.32, 1.36, 1.99-2.19, 2.50-2.68, 3.04, 3.15-3.23, 3.74-3.90, 4.01, 4.21-4.33, 4.37-4.48, 6.45, 7.24-7.29, 7.42, 7.54, 7.54-7.69, 8.18-8.23, 8.46-8.52, 9.32, 11.93.

Example 40(2)

N-{5-[(7-{[(2R)-2,3-dihydroxy-3-methylbutyl]oxy}-6-methoxy-4-quinolinyl)oxy]-2-pyridinyl}-2,5-dioxo-1-phenyl-1,2,5,6,7,8-hexahydro-3-quinolinecarboxamide TLC: Rf 0.48 (dichloromethane:methanol=9:1);
$^1$H-NMR (CDCl$_3$): δ 1.28-1.32, 2.07-2.15, 2.56-2.64, 2.90-3.40, 3.85, 4.01, 4.27, 4.43, 6.45, 7.25-7.29, 7.42, 7.53-7.66, 8.21, 8.48, 8.50, 9.32, 11.93.

Example 40(3)

N-{5-[(7-{[(2S)-2,3-dihydroxy-3-methylbutyl]oxy}-6-methoxy-4-quinolinyl)oxy]-2-pyridinyl}-1-(2,2-dimethylpropyl)-2,5-dioxo-1,2,5,6,7,8-hexahydro-3-quinolinecarboxamide TLC: Rf 0.41 (ethyl acetate:methanol=10:1);
$^1$H-NMR (CDCl$_3$): δ 1.06, 1.33, 1.37, 2.11-2.33, 2.55-2.71, 3.04, 3.06-3.15, 3.16-3.24, 3.79-3.91, 4.03, 4.21-4.33, 4.39-4.48, 6.46, 7.43, 7.53-7.61, 8.27-8.33, 8.48-8.56, 9.22, 12.18.

Example 40(4)

N-{5-[(7-{[(2R)-2,3-dihydroxy-3-methylbutyl]oxy}-6-methoxy-4-quinolinyl)oxy]-2-pyridinyl}-1-(2,2-dimethylpropyl)-2,5-dioxo-1,2,5,6,7,8-hexahydro-3-quinolinecarboxamide TLC: Rf 0.45 (dichloromethane:methanol=9:1);
$^1$H-NMR (CDCl$_3$): δ 1.06, 1.33-1.37, 2.18-2.26, 2.63, 3.00-3.20, 3.87, 4.02, 4.28, 4.44, 6.46, 7.43, 7.55-7.60, 8.30, 8.49-8.55, 9.21, 12.18.

Example 40(5)

N-{5-[(7-{[(2R)-2,3-dihydroxy-3-methylbutyl]oxy}-6-methoxy-4-quinolinyl)oxy]-2-pyridinyl}-2',5'-dioxo-1'-phenyl-2',5',6',8'-tetrahydro-1'H-spiro[cyclopropane-1,7'-quinoline]-3'-carboxamide TLC: Rf 0.49 (dichloromethane:methanol=9:1);
$^1$H-NMR (CDCl$_3$): δ 0.37-0.40, 0.53-0.56, 1.32-1.36, 2.41, 2.48, 2.98, 3.19, 3.85, 4.01, 4.27, 4.43, 6.46, 7.21-7.24, 7.42, 7.54-7.65, 8.22, 8.49-8.52, 9.36, 11.94.

Example 40(6)

N-{5-[(7-{[(2S)-2,3-dihydroxy-3-methylbutyl]oxy}-6-methoxy-4-quinolinyl)oxy]-2-pyridinyl}-1-(3-fluorophenyl)-2,5-dioxo-1,2,5,6,7,8-hexahydro-3-quinolinecarboxamide TLC: Rf 0.56 (ethyl acetate:methanol=10:1, DNH silica);
$^1$H-NMR (CDCl$_3$): δ 1.32, 1.36, 2.05-2.22, 2.53-2.71, 2.98-3.09, 3.11-3.26, 3.77-3.92, 4.01, 4.20-4.30, 4.39-4.47, 6.45, 7.00-7.13, 7.28-7.36, 7.42, 7.51-7.69, 8.23, 8.45-8.54, 9.32, 11.86.

Example 41 bis(2-methyl-2-propanyl)(5-{[7-benzyloxy)-6-methoxy-4-quinolinyl]oxy}-2-pyridinyl)imidodicarbonate 5-{[7-(benzyloxy)-6-methoxy-4-quinolinyl]oxy}-2-pyridinamine (1.6 g) was dissolved in a 1,3-dimethyl-3,4,5,6-tetrahydro-2-(1H)-pyrimidinone solution (15 mL) of di-tert-butyl dicarbonate (CAS registration No.: 24424-99-5) (3.95 mL). Triethyl amine (9.37 mL) and DMAP (52 mg) were added to the resulting solution, and the solution was stirred at room temperature for five hours. The reaction solution was diluted with hexane:ethyl acetate mixed solution (1:3), and washed with water. Then, the organic layer was concentrated, and purified by silica gel column chromatography (hexane:ethyl acetate=4:1→0:1→ethyl acetate:methanol=50:1-20:1) to obtain the title compound (2.4 g) having the following physical property values.
TLC: Rf 0.51 (ethyl acetate);
$^1$H-NMR (CDCl$_3$): δ 1.49, 4.04, 5.33, 6.45, 7.30-7.43, 7.44-7.62, 8.41, 8.50.

Example 42 bis(2-methyl-2-propanyl) {5-[(7-hydroxy-6-methoxy-4-quinolinyl)oxy]-2-pyridinyl}imidodicarbonate Under argon atmosphere, ethyl acetate (10 mL) and ethanol (30 mL) were added to and dissolved in the compound produced in Example 41 (1.4 g). Palladium hydroxide (20 wt %, 420 mg) was added thereto, and the mixture was stirred under hydrogen atmosphere at room temperature for five hours. Palladium hydroxide was removed through Celite, and the filtrate was concentrated to obtain the title compound (1.2 g).
TLC: Rf 0.49 (ethyl acetate);
$^1$H-NMR (CDCl$_3$): δ 1.50, 4.08, 6.44, 7.36, 7.46-7.60, 8.42, 8.53.

Example 43 bis(2-methyl-2-propanyl) [5-({6-methoxy-7-[(3-methyl-3-buten-1-yl)oxy]-4-quinolinyl}oxy)-2-pyridinyl] imidodicarbonate 3-methyl-3-buten-1-ol (231 mg), N,N,N',N'-tetramethyl azodicarboxamide (TMAD) (462 mg), and tri-n-butylphosphine (544 mg) were added to a THF suspension (20 mL) of the compound produced in Example 42 (500 mg), and the mixture was stirred at room temperature for three hours. The reaction solution was diluted with ethyl acetate, and concentrated by removing insoluble matters. The resulting residue was purified by silica gel column chromatography (hexane:ethyl acetate=3:2→0:1) to obtain the title compound (570 mg) having the following physical property values.
TLC: Rf 0.52 (hexane:ethyl acetate=3:7);
$^1$H-NMR (CDCl$_3$): δ 1.49, 1.86, 2.68, 4.03, 4.33, 4.76-4.99, 6.46, 7.35, 7.45, 7.50, 7.55, 8.42, 8.52.

Example 44 bis(2-methyl-2-propanyl) {5-[{7-[(3S)-3,4-dihydroxy-3-methylbutoxy]-6-methoxy-4-quinolinyl}oxy]-2-pyridinyl}imidodicarbonate Dichloromethane:t-butanol:water=1:1:1 (1.5 mL) was added to and dissolved in the compound produced in Example 43 (170 mg), AD-mix-R (431 mg) and methane sulfonamide (58 mg) were added thereto, and the mixture was stirred at room temperature overnight. The reaction solution was diluted with ethyl acetate, and washed with water. The organic layer was collected and purified by silica gel column chromatography (hexane:ethyl acetate=4:1→0:1→ethyl acetate:methanol=9:1) to obtain the title compound (152 mg) having the following physical property values.

TLC: Rf 0.54 (ethyl acetate:methanol=9:1);

$^1$H-NMR (CDCl$_3$): δ 1.29, 1.50, 2.06-2.17, 2.19-2.36, 2.90-3.32, 3.45-3.65, 4.02, 4.28-4.51, 6.48, 7.36, 7.45, 7.51, 7.56, 8.42, 8.52.

Example 45

4-(4-{4-[(6-amino-3-pyridinyl)oxy]-6-methoxy-7-quinolinyl}oxy)-(2S)-2-methyl-1,2-butanediol Trifluoroacetic acid (2 mL) was added to a dichloromethane solution (5 mL) of the compound produced in Example 44 (152 mg). The mixture was stirred at room temperature for two hours. The reaction solution was concentrated, and subjected to azeotrope with toluene twice. The resulting residue was purified by silica gel column chromatography (NH silica, ethyl acetate:methanol=9:1) to obtain the title compound (100 mg) having the following physical property values.

TLC: Rf 0.35 (dichloromethane:methanol=9:1, NH silica);

$^1$H-NMR (CDCl$_3$): δ 1.28, 2.01-2.15, 2.17-2.34, 2.74-2.94, 3.08-3.23, 3.44-3.66, 4.03, 4.26-4.46, 4.52, 6.43, 6.61, 7.31, 7.41, 7.56, 8.03, 8.48.

Example 46

N-{5-[(7-{[(3 S)-3,4-dihydroxy-3-methylbutyl]oxy}-6-methoxy-4-quinolinyl)oxy]-2-pyridinyl}-2,5-dioxo-1-phenyl-1,2,5,6,7,8-hexahydro-3-quinolinecarboxamide

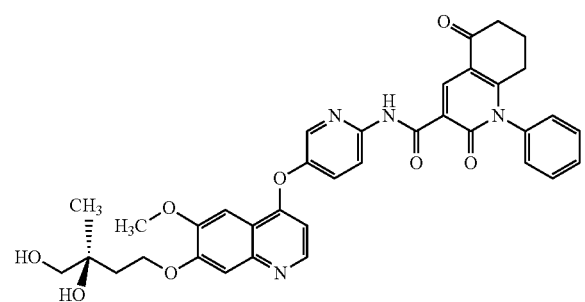

The title compound having the following physical property values was obtained by the procedure having the same purpose as in Example 5, using the compound produced in Example 45 and the compound produced in Example 4.

TLC: 0.43 (dichloromethane:methanol=9:1);

$^1$H-NMR (CDCl$_3$): δ 1.28, 2.05-2.30, 2.56-2.64, 2.70-3.30, 3.48-3.60, 4.02, 4.31-4.45, 6.45, 7.25-7.28, 7.33, 7.43-7.67, 8.21, 8.48-8.51, 9.32, 11.93.

Examples 46(1) to 46(3)

The following Example compounds were obtained by the procedure having the same purpose as in Example 46, using the compound produced in Example 45, or a compound produced by subjecting the compound produced in Example 43 to the procedure having the same purpose as in Example 44→Example 45 using AD-mix-α in place of AD-mix-β, and the compound produced in Example 4 or a corresponding carboxylic acid derivative in place of it.

Example 46(1)

N-{5-[(7-{[(3R)-3,4-dihydroxy-3-methylbutyl]oxy}-6-methoxy-4-quinolinyl)oxy]-2-pyridinyl}-2,5-dioxo-1-phenyl-1,2,5,6,7,8-hexahydro-3-quinolinecarboxamide TLC: 0.40 (ethyl acetate:methanol=10:1);

$^1$H-NMR (CDCl$_3$): δ 1.28, 1.97-2.17, 2.18-2.35, 2.52-2.69, 2.74-2.89, 3.13, 3.40-3.69, 4.02, 4.23-4.52, 6.45, 7.20-7.30, 7.42, 7.53, 7.54-7.70, 8.21, 8.45-8.52, 9.32, 11.93.

Example 46(2)

N-{5-[(7-{[(3 S)-3,4-dihydroxy-3-methylbutyl]oxy}-6-methoxy-4-quinolinyl)oxy]-2-pyridinyl}-2',5'-dioxo-1'-phenyl-2',5',6',8'-tetrahydro-1'H-spiro[cyclopropane-1,7'-quinoline]-3'-carboxamide TLC: 0.45 (dichloromethane:methanol=9:1);

$^1$H-NMR (CDCl$_3$): δ 0.37-0.41, 0.53-0.56, 1.28, 2.05-2.30, 2.42, 2.48, 2.70-3.30, 3.48-3.60, 4.02, 4.31-4.45, 6.45, 7.21-7.24, 7.42, 7.48-7.65, 8.21, 8.48-8.51, 9.36, 11.93.

Example 46(3)

N-{5-[(7-{[(3R)-3,4-dihydroxy-3-methylbutyl]oxy}-6-methoxy-4-quinolinyl)oxy]-2-pyridinyl}-2',5'-dioxo-1'-phenyl-2',5',6',8'-tetrahydro-1'H-spiro[cyclopropane-1,7'-quinoline]-3'-carboxamide TLC: 0.50 (ethyl acetate:methanol=10:1, NH silica);

$^1$H-NMR (CDCl$_3$): δ 0.33-0.43, 0.50-0.61, 1.28, 1.98-2.14, 2.16-2.33, 2.42, 2.48, 2.73-2.91, 3.08-3.18, 3.42-3.68, 4.02, 4.23-4.51, 6.46, 7.19-7.25, 7.42, 7.54, 7.55-7.66, 8.22, 8.46-8.54, 9.36, 11.94.

Example 47

(5E)-5-(hydroxyimino)-4-methyl-2-oxo-1-phenyl-1,2,5,6,7,8-hexahydro-3-quinoline carboxylic acid A pyridine solution (1.0 mL) of the compound produced in Example 4 (142 mg) and hydroxylamine hydrochloride (208 mg) was heated and refluxed for one hour. The solution was cooled to room temperature. The reaction solution was diluted with ethyl acetate and washed with 1 mol/L hydrochloric acid. The obtained organic layer was concentrated to obtain the title compound (151 mg) having the following physical property values.

TLC: Rf 0.42 (dichloromethane:methanol=9:1);

$^1$H-NMR (DMSO-d$_6$): δ 1.63-1.81, 2.26-2.36, 2.60, 7.38-7.46, 7.51-7.68, 8.90, 11.30, 14.03.

Example 48

N-{(5E)-5-[(6,7-dimethoxy-4-quinolinyl)oxy]-2-pyridinyl}-5-(hydroxyimino)-2-oxo-1-phenyl-1,2,5,6,7,8-hexahydro-3-quinolinecarboxamide

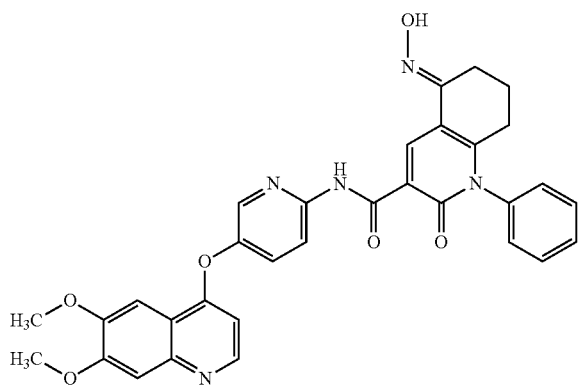 [SMILES: COc1cc2nccc(Oc3ccc(NC(=O)c4cc5c(n(-c6ccccc6)c4=O)CCC/C5=N\O)nc3)c2cc1OC]

The title compound having the following physical property values were obtained by the procedure having the same purpose as in Example 5, using the compound produced in Example 47 and the compound produced in Example 2.

TLC: 0.15 (ethyl acetate, NH silica);
$^1$H-NMR (CDCl$_3$): δ 1.77-1.94, 2.38, 2.77, 4.05, 6.46, 7.20-7.25, 7.43, 7.50-7.65, 7.99-8.07, 8.22, 8.48, 8.52, 9.33, 12.23.

Example 48(1)

N-{5-[(6,7-dimethoxy-4-quinolinyl)oxy]-2-pyridinyl}-(5E)-5-(methoxyimino)-2-oxo-1-phenyl-1,2,5,6,7,8-hexahydro-3-quinolinecarboxamide The title compound having the following physical property values was obtained by the procedure having the same purpose as in Example 48, using a corresponding carboxylic acid derivative in place of the compound produced in Example 47 and the compound produced in Example 2.

TLC: 0.18 (ethyl acetate);
$^1$H-NMR (CDCl$_3$): δ 1.74-1.92, 2.29-2.40, 2.62-2.75, 4.00, 4.05, 6.45, 7.20-7.28, 7.42, 7.50-7.66, 8.20-8.24, 8.46-8.52, 9.36, 12.26.

Example 49

7-(benzyloxy)-4-(2-fluoro-4-nitrophenoxy)-6-methoxy-quinoline The title compound having the following physical property values was obtained by the procedure having the same purpose as in Example 24, using 7-benzyloxy-6-methoxy-quinoline-4-ol in place of 6,7-dimethoxy quinoline-4-ol.

TLC: Rf 0.76 (hexane:ethyl acetate=1:1);
$^1$H-NMR (CDCl$_3$): δ 4.03, 5.34, 6.54, 7.28-7.43, 7.45, 7.47-7.55, 8.10-8.15, 8.19, 8.56.

Example 50

4-(2-fluoro-4-nitrophenoxy)-6-methoxy-7-quinolinol hydrobromate 5.1 mol/L hydrobromic acid-acetic acid solution (10 mL) was added to the compound produced in Example 49 (1.6 g). The mixture was stirred at room temperature for five hours. MTBE (50 mL) was added to the reaction solution, and the resulting solution was stirred. Generated precipitates were collected by filtration to obtain the title compound (1.5 g) having the following physical property values.
$^1$H-NMR (CD$_3$OD): δ 4.14, 7.05, 7.43, 7.76-7.85, 7.86, 8.30-8.38, 8.39-8.46, 8.69.

Example 51

4-(2-fluoro-4-nitrophenoxy)-6-methoxy-7-[3-(4-morpholinyl)propoxy]quinoline

Cesium carbonate (4.0 g) and 4-(3-chloropropyl)morpholine (517 mg) were added to a DMF solution (9.8 mL) of the compound produced in Example 50 (1.0 g), and the mixture was stirred at 60° C. for 16 hours. The mixture solution was diluted with ethyl acetate, and washed with water. The water layer was extracted with ethyl acetate twice. The combined organic layer was dried over anhydrous sodium sulfate and concentrated. The resulting residue was purified by silica gel column chromatography (NH silica, hexane:ethyl acetate=1:1-0:1) to obtain the title compound (600 mg) having the following physical property values.

TLC: Rf 0.50 (ethyl acetate, NH silica);
$^1$H-NMR (DMSO-d$_6$): δ 1.90-2.07, 2.32-2.43, 3.25-3.35, 3.48-3.64, 3.92, 4.21, 6.77, 7.45, 7.55-7.67, 8.14-8.25, 8.41-8.50, 8.56.

Example 52

3-fluoro-4-{(6-methoxy-7-(3-morpholinopropoxy)quinoline-4-yl)oxy}aniline

Under argon atmosphere, the compound produced in Example 51 (300 mg) was dissolved in ethyl acetate:ethanol=1:1 (30 mL), and palladium hydroxide (20 wt %, 99 mg) was added to the solution, and the argon atmosphere was replaced with a hydrogen atmosphere. After the solution was stirred at room temperature for eight hours, the reaction solution was filtered through Celite, and the filtrate was concentrated to obtain the title compound (240 mg) having the following physical property values.
$^1$H-NMR (CDCl$_3$): δ 2.03-2.23, 2.43-2.53, 2.57, 3.66-3.77, 3.86, 4.03, 4.26, 6.40, 6.45-6.61, 7.03, 7.42, 7.58, 8.46.

Example 53

N-[3-fluoro-4-({6-methoxy-7-[3-(4-morpholinyl)propoxy]-4-quinolinyl}oxy)phenyl]-2,5-di oxo-1-phenyl-1,2,5,6,7,8-hexahydro-3-quinolinecarboxamide

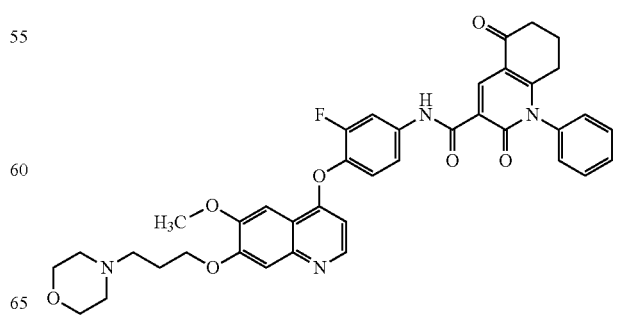

The title compound having the following physical property values was obtained by the procedure having the same purpose as in Example 5, using the compound produced in Example 52 and the compound produced in Example 2.

TLC: Rf 0.71 (ethyl acetate:methanol=10:1, NH silica);

$^1$H-NMR (DMSO-d$_6$): δ 1.88-2.07, 2.34-2.41, 2.41-2.46, 2.51-2.57, 3.31-3.37, 3.52-3.64, 3.94, 4.20, 6.42-6.49, 7.39, 7.40-7.53, 7.54-7.71, 8.04, 8.46, 8.95, 11.64.

Example 54 methyl 2-oxo-2,5,6,7-tetrahydro-1H-cyclopenta[b]pyridine-3-carboxylate 2-oxo-1,5,6,7-tetrahydro-cyclopenta[b]pyridine-3-carboxylic acid (CAS registration No.: 115122-63-9) (200 mg) was dissolved in methanol (20 mL) at room temperature, and concentrated sulfuric acid (0.006 mL) was added to the solution. The mixture was stirred at a bath temperature (70° C.) for four hours. The solution was left to cool to room temperature, the solvent was distilled off under reduced pressure, and a sodium hydrogen bicarbonate aqueous solution and dichloromethane were added thereto, and the solution was separated. The organic layer was washed with a saturated saline solution, and then was dried over anhydrous sodium sulfate, and the solvent was distilled off under reduced pressure to obtain the title compound (155 mg) having the following physical property values.

TLC: Rf 0.21 (ethyl acetate);

$^1$H-NMR (CDCl$_3$): δ 2.13-2.20, 2.80-2.84, 2.97-3.03, 3.91, 8.10.

Example 55 methyl 2-oxo-1-phenyl-2,5,6,7-tetrahydro-1H-cyclopenta[b]pyridine-3-carboxylate

The compound produced in Example 54 (140 mg) was dissolved in dichloromethane (7 mL) at room temperature. Phenylboronic acid (220 mg), copper acetate (263 mg), and pyridine (0.234 mL) were added to the solution, and the solution was stirred for 20 hours. The solution was filtered through a glass filter, and the solvent was distilled off under reduced pressure. The resulting residue was purified by silica gel column chromatography (hexane:ethyl acetate=8:2→ethyl acetate) to obtain the title compound (131 mg) having the following physical property values.

TLC: Rf 0.51 (ethyl acetate);

$^1$H-NMR (CDCl$_3$): δ 2.02-2.12, 2.53-2.58, 2.83-2.88, 3.88, 7.20-7.23, 7.44-7.53, 8.21.

Example 56

2-oxo-1-phenyl-2,5,6,7-tetrahydro-1H-cyclopenta[b]pyridine-3-carboxylic acid The compound produced in Example 55 (120 mg) was dissolved in methanol (2 mL) at room temperature. 2 mol/L sodium hydroxide aqueous solution (0.891 mL) was added to the solution, and the solution was stirred for one hour. 2N hydrochloric acid (0.891 mL) and ethyl acetate were added to the reaction solution, and the solution was separated. The organic layer was washed with a saturated saline solution, then was dried over anhydrous sodium sulfate, and the solvent was distilled off under reduced pressure to obtain the title compound (109 mg) having the following physical property values.

TLC: Rf 0.64 (ethyl acetate);

$^1$H-NMR (CDCl$_3$): δ 2.09-2.19, 2.63-2.68, 2.92-2.97, 7.25-7.30, 7.52-7.62, 8.51, 14.24.

Example 57

N-{5-[(6,7-dimethoxy-4-quinolinyl)oxy]-2-pyridinyl}-2-oxo-1-phenyl-2,5,6,7-tetrahydro-1H-cyclopenta[b]pyridine-3-carboxamide

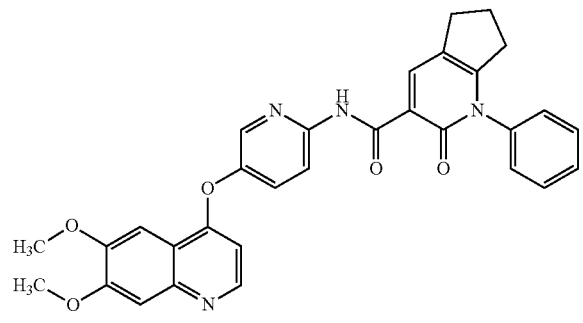 [SMILES: COc1cc2nccc(Oc3ccc(NC(=O)c4cc5c(n(-c6ccccc6)c4=O)CCC5)nc3)c2cc1OC]

The title compound having the following physical property values was obtained by the procedure having the same purpose as in Example 5, using the compound produced in Example 56 and the compound produced in Example 2.

TLC: Rf 0.65 (ethyl acetate:methanol=9:1);

$^1$H-NMR (DMSO-d$_6$): δ 2.03-2.13, 2.60-2.65, 2.92-2.97, 3.97, 3.99, 6.58, 7.45, 7.47-7.52, 7.57, 7.58-7.68, 7.86-7.90, 8.38, 8.48, 8.53, 8.60, 12.58.

Examples 57(1) to 57(2)

The Example compounds each having the following physical property values were obtained by the procedure having the same purpose as in Example 55→Example 56→Example 57, using a corresponding derivative in place of the compound produced in Example 54 and the compound produced in Example 2.

Example 57(1)

N-{5-[(6,7-dimethoxy-4-quinolinyl)oxy]-2-pyridinyl}-2-oxo-1-phenyl-1,2,5,6,7,8-hexahydro-3-quinolinecarboxamide TLC: Rf 0.63 (ethyl acetate, NH silica);

$^1$H-NMR (CDCl$_3$): δ 1.71-1.83, 2.20-2.29, 2.68-2.76, 4.05, 6.44, 7.19-7.24, 7.42, 7.46-7.62, 8.21, 8.44-8.50, 12.51.

Example 57(2)

N-{5-[(6,7-dimethoxy-4-quinolinyl)oxy]-2-pyridinyl}-2,5-dioxo-1-phenyl-2,5,6,7-tetrahydro-1H-cyclopenta[b]piperidine-3-carboxamide TLC: Rf 0.63 (ethyl acetate:methanol=9:1);

$^1$H-NMR (CDCl$_3$): δ 2.68-2.81, 4.05, 6.45, 7.35, 7.43, 7.53, 7.55-7.68, 8.24, 8.49, 8.51, 9.03, 11.91.

Example 58

N-{5-[(7-{[(4S)-2,2-dimethyl-1,3-dioxolane-4-yl]methoxy}-6-methoxy-4-quinolinyl)oxy]-2-pyridinyl}-2,5-dioxo-1-phenyl-1,2,5,6,7,8-hexahydro-3-quinolinecarboxamide The title compound having the following physical property values was obtained by the procedure having the same purpose as in Example 17, using the compound obtained by subjecting the compound produced in Example 37 to procedure having the same purpose as in Example 11→Example 12→Example 13→Example 14→Example 15→Example 16, and (S)-(2,2-dimethyl-1,3-dioxolane-4-yl)methanol.

TLC: Rf 0.60 (ethyl acetate, NH silica);
$^1$H-NMR (CDCl$_3$): δ 1.42, 1.50, 2.11, 2.60, 4.01, 4.14-4.29, 4.64, 6.44, 7.42, 7.52-7.65, 8.21, 8.47, 8.50, 9.32, 11.92.

Example 59

N-{5-[(7-{[(2R)-2,3-dihydroxypropyl]oxy}-6-methoxy-4-quinolinyl)oxy]-2-pyridinyl}-2,5-dioxo-1-phenyl-1,2,5,6,7,8-hexahydro-3-quinolinecarboxamide

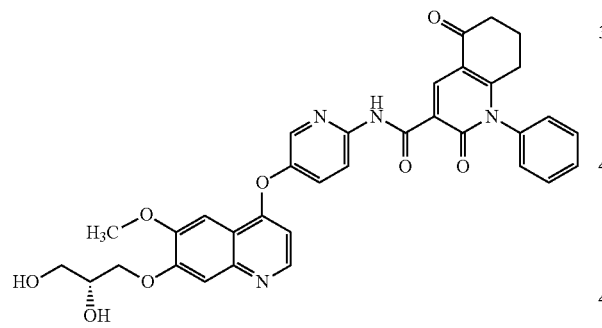

The compound produced in Example 58 (35 mg) was dissolved in THF (1 mL) at room temperature. Methanol (1 mL) and p-toluenesulfonic acid monohydrate (3.0 mg) were added to the solution, and the mixture was stirred room temperature for 16 hours. The reaction solution was diluted with ethyl acetate, and washed with water and a saturated sodium hydrogen carbonate aqueous solution. The organic layer was dried over anhydrous sodium sulfate, and then concentrated. The resulting residue was purified by silica gel chromatography (ethyl acetate:methanol=100:0-70:30) to obtain the title compound (32 mg) having the following physical property values.

TLC: Rf 0.55 (ethyl acetate:methanol=5:1, NH silica);
$^1$H-NMR (CDCl$_3$): δ 2.11, 2.56-2.64, 3.89, 4.02, 4.21-4.36, 6.45, 7.25-7.28, 7.44, 7.53-7.66, 8.21, 8.48-8.51, 9.32, 11.93.

Examples 59(1) to 59(3)

The following Example compounds were obtained by the procedure having the same purpose as in Example 59, using the compound produced in Example 58 or a corresponding compound in place of it.

Example 59(1)

N-{5-[(7-{[(2S)-2,3-dihydroxypropyl]oxy}-6-methoxy-4-quinolinyl)oxy]-2-pyridinyl}-2,5-dioxo-1-phenyl-1,2,5,6,7,8-hexahydro-3-quinolinecarboxamide TLC: Rf 0.55 (ethyl acetate:methanol=5:1, NH silica);
$^1$H-NMR (CDCl$_3$): δ 2.11, 2.56-2.64, 3.90, 4.02, 4.21-4.36, 6.44, 7.24-7.29, 7.44, 7.52-7.66, 8.22, 8.48-8.51, 9.33, 11.94.

Example 59(2)

N-{5-[(7-{[(2S)-2,3-dihydroxypropyl]oxy}-6-methoxy-4-quinolinyl)oxy]-2-pyridinyl}-1-(2,2-dimethylpropyl)-2,5-dioxo-1,2,5,6,7,8-hexahydro-3-quinolinecarboxamide TLC: Rf 0.35 (ethyl acetate, NH silica);
$^1$H-NMR (CDCl$_3$): δ 1.06, 2.22, 2.63, 3.09, 3.89, 4.02, 4.22, 4.34, 6.44, 7.43, 7.55, 7.58, 8.30, 8.52, 8.54, 9.21, 12.18.

Example 59(3)

N-{5-[(7-{[(2R)-2,3-dihydroxypropyl]oxy}-6-methoxy-4-quinolinyl)oxy]-2-pyridinyl}-1-(2,2-dimethylpropyl)-2,5-dioxo-1,2,5,6,7,8-hexahydro-3-quinolinecarboxamide TLC: Rf 0.35 (ethyl acetate, NH silica);
$^1$H-NMR (CDCl$_3$): δ 1.06, 2.22, 2.63, 3.09, 3.89, 4.02, 4.22, 4.34, 6.44, 7.43, 7.55, 7.58, 8.30, 8.52, 8.54, 9.21, 12.18.

Example 60

5-hydroxy-N-{5-[(7-hydroxy-6-methoxy-4-quinolinyl)oxy]-2-pyridinyl}-2-oxo-1-phenyl-1,2,5,6,7,8-hexahydro-3-quinolinecarboxamide The title compound having the following physical property values was obtained by the procedure having the same purpose as in Example 11→Example 12→Example 13→Example 14→Example 15→Example 16, using the compound produced in Example 37.

TLC: Rf 0.26 (dichloromethane:methanol=19:1);
$^1$H-NMR (CDCl$_3$): δ 1.62-1.93, 2.27, 4.08, 4.85, 6.42, 7.23, 7.52-7.62, 8.21, 8.46, 8.51, 8.80, 12.37.

Example 61

N-{5-[(7-hydroxy-6-methoxy-4-quinolinyl)oxy]-2-pyridinyl}-2-oxo-1-phenyl-1,2,5,6,7,8-hexahydro-3-quinolinecarboxamide

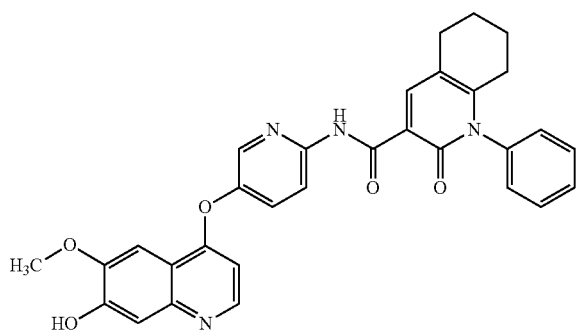 [SMILES: COc1cc2c(Oc3ccc(NC(=O)c4cc5c(n(-c6ccccc6)c4=O)CCCC5)nc3)ccnc2cc1O]

The compound produced in Example 60 (300 mg) was dissolved in dichloromethane (5 mL). Triethylsilane (127 mg), and trifluoroacetic acid (0.081 mL) were added to the solution, sequentially. The solution was stirred at room temperature for 22 hours. The reaction solution was diluted with ethyl acetate, and washed with water and a saturated sodium hydrogen carbonate aqueous solution. The organic layer was dried over anhydrous sodium sulfate, and then concentrated. The resulting residue was purified by silica gel chromatography (hexane:ethyl acetate=30:70-0:100) to obtain the title compound (183 mg) having the following physical property values.

TLC: Rf 0.77 (ethyl acetate:methanol=5:1);
$^1$H-NMR (CDCl$_3$): δ 1.75, 2.23, 2.72, 4.08, 6.42, 7.22, 7.51-7.60, 8.21, 8.44-8.51, 8.49, 12.51.

Example 62

4-methyl-7,8-dihydro-2H-chromene-2,5(6H)-dione

Ethyl acetoacetate (CAS registration No.: 141-97-9) (17.40 g), 1,3-cyclohexanedione (CAS registration No.: 504-02-9) (10.00 g), DMAP (0.22 g), and pyridine (30 mL) were placed in a 200-mL eggplant flask, and stirred at a bath temperature (140° C.) for one day. After the mixture was left to cool to room temperature, the solvent was distilled off under reduced pressure. The resulting residue was purified by silica gel column chromatography (hexane:ethyl acetate=4:1) to obtain the title compound (4.50 g) having the following physical property values.

(LC-MS/ELSD): (retention time: 0.81 min);
$^1$H-NMR (CDCl$_3$): δ 2.11, 2.48, 2.57, 2.87, 5.99.

Example 63

3-bromo-4-methyl-7,8-dihydro-2H-chromene-2,5(6H)-dione N-bromosuccinimide (CAS registration No.: 128-08-5) (2.00 g) was added into a DMF (40 mL) solution of the compound produced in Example 62 in a 100-mL eggplant flask, and the solution was stirred at room temperature for one day. The solvent was distilled off under reduced pressure. The resulting residue was purified by silica gel column chromatography (hexane:ethyl acetate=9:1) to obtain the title compound (1.16 g) having the following physical property values.

(LC-MS/ELSD): (retention time: 0.76 min);
$^1$H-NMR (CDCl$_3$): δ 2.12, 2.59, 2.69, 2.87.

Example 64

3-bromo-4-methyl-1-phenyl-7,8-dihydro-2,5(1H,6H)-quinolinedione

The compound produced in Example 63 (1.15 g) and aniline (1.25 g) were placed in a 30-mL eggplant flask. The mixture was stirred at a bath temperature (70° C.) for 20 hours. 1 mol/L hydrochloric acid was added to the reaction solution. The reaction solution was extracted with ethyl acetate, washed with water and a saturated saline solution sequentially in this order, and dried over anhydrous sodium sulfate. The solvent was distilled off under reduced pressure. The resulting residue was purified by silica gel column chromatography (hexane:ethyl acetate=7:3) to obtain the title compound (1.31 g) having the following physical property values.

(LC-MS/ELSD): (retention time: 1.12 min);
$^1$H-NMR (CDCl$_3$): δ 1.96, 2.43, 2.54, 2.79, 7.16-7.20, 7.49-7.58.

Example 65 methyl 4-methyl-2,5-dioxo-1-phenyl-1,2,5,6,7,8-hexahydro-3-quinoline carboxylate The compound produced in Example 64 (1.11 g), potassium acetate (0.66 g), DMF (11 mL), and methanol (11 mL), and, after degassing, [1,1'-bis(diphenylphosphino)ferrocene]palladium(II)dichloride dichloromethane complex (1:1) [PdCl$_2$ (dppf)$_2$CH$_2$Cl$_2$] (0.27 g) were placed in a 200-mL eggplant flask. After replacement with carbon monoxide was carried on, stirring at a bath temperature (70° C.) was carried out for 17 hours. 1 mol/L hydrochloric acid was added to the reaction solution. The reaction solution was extracted with ethyl acetate, washed with water and a saturated saline solution in this order, and dried over anhydrous sodium sulfate. The solvent was distilled off under reduced pressure. The resulting residue was purified by silica gel column chromatography (hexane:ethyl acetate=7:3) to obtain the title compound (0.51 g) having the following physical property values.

(LC-MS/ELSD): (retention time: 0.75 min);
$^1$H-NMR (CDCl$_3$): δ 1.97, 2.48, 2.53, 2.56, 3.89, 7.17-7.20, 7.48-7.56.

Example 66

4-methyl-2,5-dioxo-1-phenyl-1,2,5,6,7,8-hexahydro-quinoline-3-carboxylic acid

The compound produced in Example 65 (1.85 g) and 5 mol/L hydrochloric acid (19 mL) were placed in a 50-mL eggplant flask. The mixture was stirred at a bath temperature (50° C.) for 26 hours. Precipitate was removed by filtration, and the filtrate solvent was distilled off under reduced pressure. The resulting residue was washed in a slurry form with methanol and ethyl acetate to obtain the title compound (0.89 g) having the following physical property values.

(LC-MS/ELSD): (retention time: 0.66 min);
$^1$H-NMR (CD$_3$OD): δ 1.97, 2.54, 2.63, 7.29-7.32, 7.54-7.63.

Example 67

N-{5-[(6,7-dimethoxy-4-quinolinyl)oxy]-2-pyridinyl}-4-methyl-2,5-dioxo-1-phenyl-1,2,5,6,7,8-hexahydro-3-quinolinecarboxamide

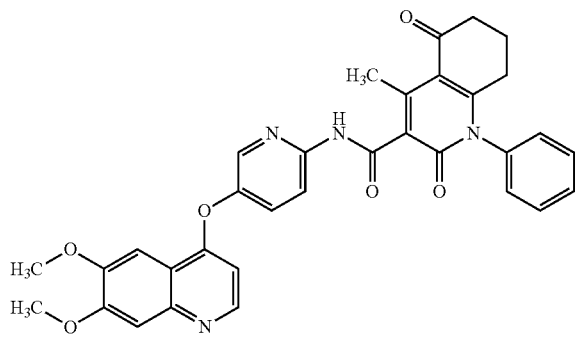 [SMILES: COc1cc2nccc(Oc3ccc(NC(=O)c4c(C)c5c(n(-c6ccccc6)c4=O)CCCC5=O)nc3)c2cc1OC]

The title compound having the following physical property values was obtained by the procedure having the same purpose as in Example 5, using the compound produced in Example 66 and the compound produced in Example 2.

TLC: Rf 0.62 (dichloromethane:methanol=9:1);
$^1$H-NMR (CDCl$_3$): δ 2.01, 2.53, 2.58, 2.86, 4.05, 6.42, 7.22, 7.42, 7.49-7.61, 8.20, 8.45, 8.50, 9.73.

Example 67(1)

N-{4-[(6,7-dimethoxy-4-quinolinyl)oxy]phenyl}-4-methyl-2,5-dioxo-1-phenyl-1,2,5,6,7,8-hexahydro-3-quinolinecarboxamide The title compound having the following physical property values was obtained by the procedure having the same purpose as in Example 67, using the compound produced in Example 66 and the compound produced in Example 22.

TLC: Rf 0.48 (ethyl acetate:methanol=19:1);
$^1$H-NMR (CDCl$_3$): δ 2.01, 2.52, 2.59, 2.93, 4.04, 6.45, 7.14, 7.23, 7.41, 7.55-7.68, 7.72, 8.47, 9.79.

EXPERIMENT EXAMPLE

Biological Examples are described below. Based on these experiment methods, the effect of the compound of the present invention was verified.

Biological Example 1: Measurement of an Axl Inhibitory Activity (In Vitro Test)

An Axl enzyme inhibitory activity was measured by using LanthaScreen (registered trademark) system (Invitrogen) based on the attached instruction. The reagents used are shown below.

Reaction buffer solution: a solution containing 50 mmol/L HEPES (pH7.5), 0.01% Brij35, 10 mmol/L MgCl$_2$ and 1 mmol/L EGTA was prepared by using purified water.

Test substance solution: a solution containing a test compound of 5-fold concentration with respect to the final concentration was prepared by 20-fold diluting a DMSO solution of test compound of each concentration with the reaction buffer solution.

Enzyme solution: a solution containing 400 ng/mL Axl enzyme was prepared by using the reaction buffer solution.

Substrate solution: a solution containing 45 μmmol/L ATP and 500 nmmol/L Fluorescein-Poly GT (Invitrogen) was prepared by using the reaction buffer solution.

Detection solution: a solution containing 20 mM EDTA and 4 nM PY20 (Invitrogen) was prepared by using Dilution B (Invitrogen).

A 10 mmol/L DMSO solution of the test compound was dispensed into a 96-well plate (Nunc), and, furthermore, a 3-fold dilution series was prepared using DMSO. In each well of the 96-well plate for measurement, 5 μL each of the reaction buffer solution containing DMSO was added to a Blank group and a medium group, and 5 μL of the test substance solution was added to the test substance group, respectively. Next, 10 μL/well of the reaction buffer solution was added to the Blank group, and 10 μL/well each of the enzyme solution was added to the medium group and the test compound group, followed by stirring at room temperature for 10 min. After the completion of stirring, 10 μL each of the substrate solution was added into each well, followed by stirring at room temperature with light shielded for one hour. After the completion of reaction, 25 μL each of the detection solution was added to each well, and stood still at room temperature with light shielded for 30 min. After standing sill, fluorescence intensity at 520 nm and 495 nm at the time of irradiation with exciting light of 340 nm was measured by using Analyst GT (Molecular Devices). The phosphorylation of the artificial substrate was quantified by Time-resolved Fluorescence Resonance Energy Transfer (TR-FRET). TR-FRET ratio was calculated by dividing 520 nm fluorescence signal by 495 nm fluorescence signal for each well, and the inhibition rate (%) in the test compound group was calculated based on the following mathematical formula.

Inhibition rate (%)=[1−(TR-FRET ratio of test compound group−A)/(B−A)×100  [Math. 1]

A: average value of TR-FRET ratios of Blank group
B: average value of TR-FRET ratios of medium group Values of 50% inhibition rate (IC50 values) of the test compound were calculated from the inhibition curve based on the inhibition rate of the test compounds in each concentration.

As a result, in the compounds of the present invention, IC50 values of the compound of, for example, Examples 5, 5(1), 5(6), 17(2), and 23(2) were 0.0022 μM, 0.0056 μM, 0.0043 μM, 0.0044 μM, and 0.0011 μM, respectively.

On the other hand, as comparative compounds, the Axl inhibitory activity of each of the compound of Example 8 described in Patent Literature 1 (Comparative compound A) and the compound 2 of Example 3 described in Patent Literature 3 (Comparative compound B), having the following structures, was measured. In both cases, IC50 value was higher than 10 μM.

Comparative compound A

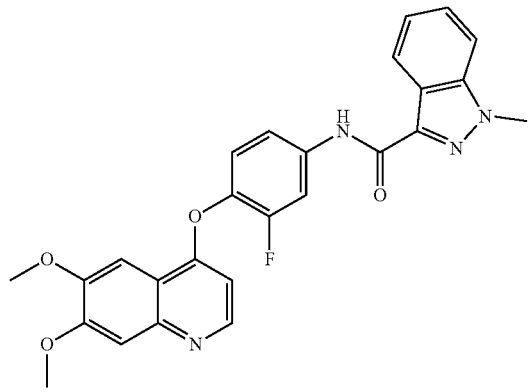

Comparative compound B

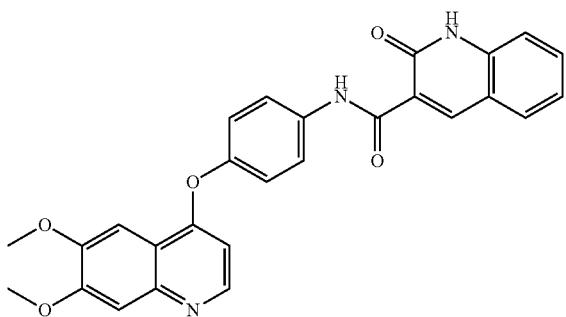

Biological Example 2: Measurement of Proliferation Suppression Rate by Using Mouse Pro-B Cell Line (Ba/F3 Axl) Stably Expressing Axl A 0.1 mmol/L DMSO solution of the test compound was dispensed into a 96-well plate, and a 3-fold dilution series was prepared using DMSO. DMSO solutions of test compounds, having various concentrations, were further 500-fold diluted with a RPMI1640 medium (containing 10% HI-FBS, 1% penicillin) and a diluted solution of the test compound having 500-fold concentration with respect to the final concentration was prepared. In each well of the 96-well plate (BD Biosciences) for measurement, 50 μL of a RPMI medium was added to the Blank group, 50 μL of a RPMI medium containing 0.2% DMSO was added to the medium group, and 50 μL of the diluted solution of the test compound was added to the test compound group, respectively. Ba/F3 Axl was diluted with a medium to have a density of $2 \times 10^5$ cells/mL to prepare a cell suspension. In each well of the 96-well plate for measurement, 50 μL each of the RPMI medium was added to the Blank group, and 50 μL each of the cell suspension to the medium group and the test compound group, respectively, and the groups were stood still at 37° C. at 5% $CO_2$ for 48 hours. After standing still, Relative Light Unit (RLU) was measured by using CELL-TITER-GLO (registered trademark) LUMINESCENT CELL VIABILITY ASSAY (Promega). The measurement was carried out according to the attached instruction. To each well, 100 μL each of light-emitting solution was added. The plate was stirred at room temperature for 3 min and then stool still at room temperature with light shielded for 10 min, and RLU was measured by using Microplate Reader (SpectraMax M5e, Molecular Devices). The average values of RLU of the Blank group and the medium group were respectively calculated, and the proliferation suppression rate of the test compound group was calculated.

Proliferation suppression rate (%)={1−(RLU of test compound group−$A$)/($B$−$A$)}×100  [Math. 2]

A: average value of RLU of Blank group
B: average value of RLU of medium group

A value of 50% inhibition rate (IC50 value) of the test compound was calculated from the inhibition curve based on the inhibition rate in each concentration of the test compound.

As a result, in the compounds of the present invention, IC50 values of the compounds of, for example, Examples 5, 5(1), 5(6), 17(2), and 23(2) were 0.0007 μM, 0.0008 μM, 0.0078 μM, 0.0012 μM, and 0.0012 μM, respectively.

On the other hand, IC50 values of the comparative compounds A and B, were 0.62 μM and >10 μM, respectively.

Biological Example 3: Evaluation of Kinase Selectivity (In Vitro Test)

Similar to Biological Example 1, values of 50% inhibition rate (IC50 value) with respect to various kinases (KDR, DDR1, FLT4, and ROS) of the test compound were measured. The Axl selective inhibitory activity of the test compound with respect to kinases, for example, KDR, was calculated based on the above-mentioned ratio of the IC50 values. The calculated values are shown in the following Table 1. As the test compound, for the compound of the present invention, the compounds of Examples 5, 5(1), 17(2), and 23(2) were used, and for the comparative compounds, the compound of Example 5 (Comparative compound C) and the compound of Example 92 (Comparative compound D) described in Patent Literature 5, having the following structure, were used.

Comparative compound C

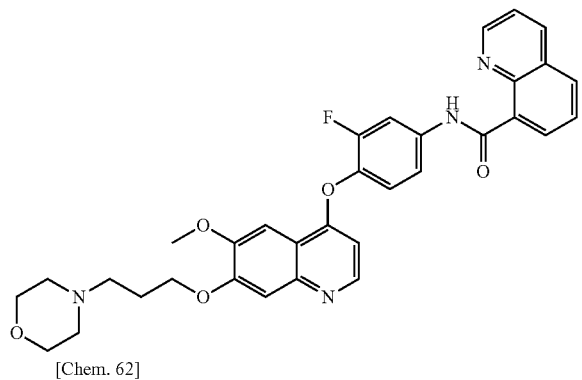

[Chem. 62]

Comparative compound D

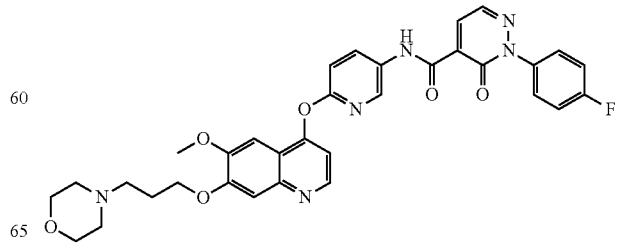

TABLE 1

| | KDR [IC50]/Axl [IC50] |
|---|---|
| Example 5 | about 900 times |
| Example 5(1) | about 1800 times |
| Example 17(2) | about 650 times |
| Example 23(2) | about 520 times |
| Comparative compound C | about 0.2 times |
| Comparative compound D | about 28 times |

Results showed that the compound of the present invention had Axl selective inhibition effect on KDR as compared with the comparative compounds. KDR is kinase also referred to as vascular endothelial growth factor receptor 2 (VEGF Receptor 2). It is known that inhibition of KDR may cause a side effect of increasing blood pressure (Hypertension, vol. 39, p. 1095-1100, 2002). Therefore, it was suggested that the compounds of the present invention were excellent compounds capable of avoiding the side effect, which was a problem in comparative compounds, for example, hypertension. Furthermore, it has been also suggested that the other three types of kinases (DDR1, FLT4, and ROS) might cause side effect to be avoided, from the phenotype of the KO mouse or transgenic mouse. It became apparent that the compound of the present invention has excellent selectivity to such specific kinases and therefore capable of avoiding side effect.

Biological Example 4: Measurement of Inhibitory Activity of Drug-Metabolizing Enzyme (Human CYP2C8 Inhibition Effect)

The reaction was carried out in a 384-well plate. As the positive control substance (CYP2C8: quercetin), a solution, which had been adjusted with DMSO to have 300 times higher concentration than the final concentration (CYP2C8: 22.5 and 225 µmol/L) and been 75-fold diluted with purified water containing 2.7% acetonitrile, was prepared (CYP2C8: 0.3 and 3 µmol/L). The test compounds were prepared to have a concentration of 0.3 and 3 mol/L with DMSO, and then 75-fold diluted with purified water containing 2.7% acetonitrile to be 4 and 40 µmol/L. Then, a reaction mixture solution was prepared by addition of a potassium phosphate buffer (pH 7.4), magnesium chloride (5 mol/L), substrate (CYP2C8: Luciferin-ME, 150 µmol/L), and $E.$ $coli$-expressed liver microsome CYP2C8 (Cypex, 30 µmol/L) (the numerical values are final concentrations). The reaction was started by addition of 8 µL of this reaction mixture, 4 µL each of the test compound and the positive control solution which had been prepared as described above, and 4 µL of NADPH production system solution (5.2 mM NADP, 13.2 mM glucose-6-phosphate, 1.6 U/mL glucose-6-phosphate dehydrogenase) and incubation was carried out at 37° C. for 30 min. Thereafter, 16 µL of luciferase solution was added to stop the reaction and to allow luciferin to emit light, and the luminescence intensity of the reaction solution was measured. The inhibition rate is a reduction rate (inhibition rate) of the luminescence intensity when compared with the control in which the reaction was carried out by the addition of DMSO in place of the test compound solution. The inhibition rate was calculated from the following mathematical formula.

$$\text{Inhibition rate (\%)}=100-\{(\text{luminescence intensity of test compound}-\text{background luminescence intensity})/(\text{luminescence intensity of control}-\text{background luminescence intensity})\times 100\} \quad [\text{Math. 3}]$$

The IC50 value was defined to be <1 µM when the inhibition rate at 1 µmol/L was not less than 50%; and >10 µM when the inhibition rate at 10 µmol/L was not more than 50%. The range between the above-mentioned range (not more than 50% at 1 µmol/L and not less than 50% at 10 µmol/L) was calculated using the following mathematical formula:

$$IC50=(50-b)/a \quad [\text{Math.4}]$$

wherein a and b are the slope and intercept of the linear regression line: y=ax+b that passes through the two points: the concentration and the inhibition rate at 1 µmol/L and the concentration and the inhibition rate at 10 µmol/L.

The IC50 values of the comparative compounds and compounds of the present invention were measured using the measurement method described above.

As a result, the IC50 value of CYP2C8 was 2.6 µM for the comparative compound E (Example 133 described in Patent Literature 4). On the other hand, for the compound of the present invention, the IC50 values of CYP2C8 were >10 µM in the compounds of, for example, Examples 5, 5(1), 17(2), and 23(2). Therefore, it was shown that the compound of the present invention had less CYP inhibition effect with respect to the comparative compound.

FORMULATION EXAMPLE

Formulation Example 1

The components indicated below were mixed by a standard method, followed by making the mixture into tablets to obtain 10,000 tablets each containing 10 mg of active ingredient.

| | |
|---|---|
| N-{5-[(6,7-dimethoxy-4-quinolinyl)oxy]-2-pyridinyl}-2,5-dioxo-1-phenyl-1,2,5,6,7,8-hexahydro-3-quinolinecarboxamide | 100 g |
| calcium carboxymethyl cellulose (disintegrant) | 20 g |
| magnesium stearate (lubricant) | 10 g |
| microcrystalline cellulose | 870 g |

Formulation Example 2

The components indicated below were mixed by a standard method, filtered through a dust-removing filter, filled into ampoules so that each ampule contains 5 ml, and thermally sterilized in an autoclave to obtain 10,000 ampoules each containing 20 mg active ingredient.

| | |
|---|---|
| N-{5-[(6,7-dimethoxy-4-quinolinyl)oxy]-2-pyridinyl}-7,7-dimethyl-2,5-dioxo-1-phenyl-1,2,5,6,7,8-hexahydro-3-quinolinecarboxamide | 200 g |
| mannitol | 20 g |
| distilled water | 50 L |

INDUSTRIAL APPLICABILITY

A compound of the present invention has a strong Axl inhibitory activity, and therefore, is useful for treatment for Axl-related diseases, for example, cancer, kidney diseases, immune system diseases, and circulatory system diseases.

The invention claimed is:
1. A method of preparing a compound represented by general formula (I-A):

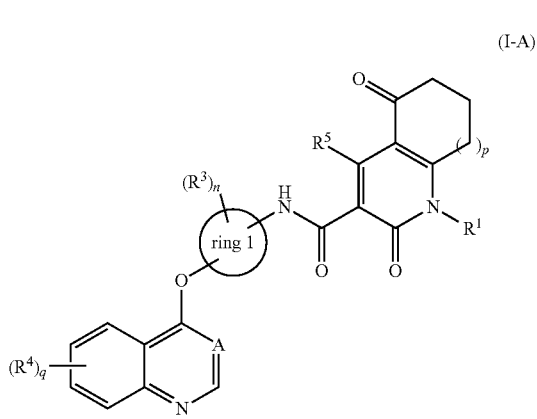

wherein
$R^1$ represents (1) a C1-8 alkyl group optionally substituted with one to five $R^{11}$, (2) a C3-7 carbon ring optionally substituted with one to five $R^{12}$, or (3) a 4- to 7-membered heterocycle optionally substituted with one to five $R^{13}$, wherein when the C1-8 alkyl group represented by $R^1$ is a branched alkyl group, the C1-3 alkyl group branched from the same carbon atom, together with the carbon atom bound thereto, optionally forms a saturated C3-7 carbon ring,
$R^3$ represents (1) a C1-4 alkyl group, (2) a halogen atom, or (3) a C1-4 haloalkyl group,
$R^4$ represents (1) a C1-4 alkoxy group, (2) a C1-4 haloalkyl group, (3) an —$OR^{41}$ group, (4) a C1-4 alkyl group, (5) a C2-4 alkenyloxy group, or (6) a C2-4 alkynyloxy group,
$R^5$ represents (1) a hydrogen atom, (2) a C1-4 alkyl group, (3) a halogen atom, (4) a C1-4 haloalkyl group, or (5) an —$OR^{21}$ group,
$R^{11}$ represents (1) an —$OR^{101}$ group, (2) an $SO_2R^{102}$ group, (3) an $NR^{103}R^{104}$ group, or (4) a C3-7 carbon ring optionally substituted with one to three halogen atoms,
$R^{12}$ represents (1) a C1-8 alkyl group optionally substituted with a hydroxyl group, or (2) a halogen atom,
$R^{13}$ represents (1) a C1-8 alkyl group optionally substituted with a hydroxyl group, or (2) a halogen atom,
$R^{21}$ represents (1) a hydrogen atom, or (2) a C1-4 alkyl group,
$R^{41}$ represents
(1) a hydrogen atom;
(2) a C1-8 alkyl group substituted with one to two substituents selected from the group consisting of (a) 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group;
(3) a C2-8 alkenyl group substituted with one to two substituents selected from the group consisting of (a) 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group; or (4) a C2-8 alkynyl group substituted with one to two substituents selected from the group consisting of (a) 5- to 7-membered cyclic group optionally substituted with one to two substituents selected from the group consisting of (i) a C1-4 alkyl group, (ii) a C1-4 haloalkyl group, and (iii) a halogen atom, (b) $NR^{401}R^{402}$, (c) a hydroxyl group, and (d) an $SO_2R^{403}$ group,
$R^{101}$ represents (1) a hydrogen atom, or (2) a C1-4 alkyl group,
$R^{102}$ represents (1) a hydrogen atom, or (2) a C1-4 alkyl group,
$R^{103}$ and $R^{104}$ each independently represents (1) a hydrogen atom, or (2) a C1-4 alkyl group,
$R^{401}$ and $R^{402}$ each independently represents (1) a hydrogen atom, or (2) a C1-4 alkyl group,
$R^{403}$ represents (1) a hydrogen atom, or (2) a C1-4 alkyl group,
A represents (1) CH, or (2) a nitrogen atom,
ring1 represents a 5- to 7-membered cyclic group,
n is an integer from 0 to 5,
p is an integer from 0 to 2,
q is an integer from 0 to 4,
when n is two or more, a plurality of $R^3$ may be the same as or different from each other, and when q is two or more, a plurality of $R^4$ may be the same as or different from each other, a salt thereof,
the method comprising the following steps (i) to (iii):
step (i): subjecting a compound presented by the general formula (d):

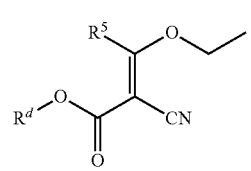

wherein $R^d$ represents a C1-4 alkyl group, and the other symbols have the same meanings as defined above or a salt thereof
and a compound represented by the general formula (III):

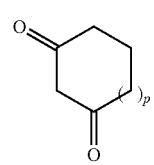

wherein all symbols have the same meanings as defined above or a salt thereof
to a cyclization reaction to produce a compound represented by the general formula (e):

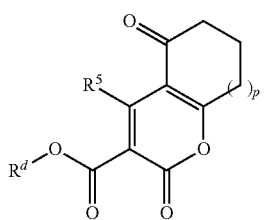

(e)

wherein all symbols have the same meanings as defined above or a salt thereof;

step (ii): subjecting the compound represented by the general formula (e) obtained in the step (i) and a compound represented by the general formula (IV):

$$H_2N-R^1 \quad (IV)$$

wherein all symbols have the same meanings as defined above or a salt thereof to an addition reaction to produce a compound represented by the general formula (f):

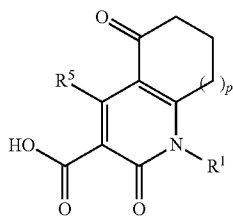

(f)

wherein all symbols have the same meanings as defined above or a salt thereof; and step (iii): subjecting the compound represented by the general formula (f) obtained in the step (ii) and a compound represented by the general formula (c):

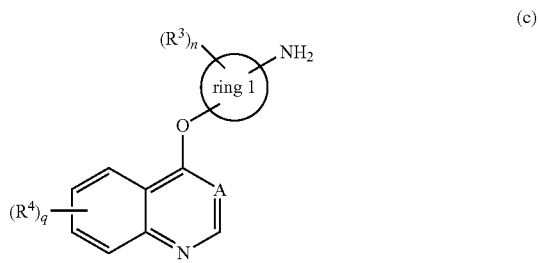

(c)

wherein all symbols have the same meanings as defined above or a salt thereof, to an amidation reaction to produce the compound represented by the general formula (I-A) or a salt thereof.

2. The method of preparing a compound according to claim 1, wherein the ring1 is benzene or pyridine.

3. The method of preparing a compound according to claim 1, wherein the compound represented by the general formula (I-A) is N-{5-[(6,7-dimethoxy-4-quinolinyl)oxy]-2-pyridinyl}-2,5-dioxo-1-phenyl-1,2,5,6,7,8-hexahydro-3-quinolinecarboxamide.

\* \* \* \* \*

UNITED STATES PATENT AND TRADEMARK OFFICE
CERTIFICATE OF CORRECTION

PATENT NO. : 10,676,462 B2
APPLICATION NO. : 16/540306
DATED : June 9, 2020
INVENTOR(S) : Inukai et al.

Page 1 of 1

It is certified that error appears in the above-identified patent and that said Letters Patent is hereby corrected as shown below:

In the Claims

In Claim 1, Column 86, Line 51, after "thereof", insert --,--;

In Claim 1, Column 86, Line 64, after "thereof", insert --,--;

In Claim 1, Column 87, Line 20, after "thereof", insert --,--.

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*